(12) United States Patent
Sasmal et al.

(10) Patent No.: US 9,303,027 B2
(45) Date of Patent: Apr. 5, 2016

(54) KAPPA OPIOID RECEPTOR AGONISTS

(75) Inventors: Pradip Kumar Sasmal, Hyderabad (IN); Vamsee Krishna Chintakunta, Hyderabad (IN); Vijay Potluri, Hyderabad (IN); Ish Kumar Khanna, Alpharetta, GA (US); Ashok Tehim, Ridgewood, NJ (US); Mahaboobi Jaleel, Hyderabad (IN); Thomas Hogberg, Akarp (SE); Oystein Rist, Ballerup (DK); Lisbeth Elster, Herlev (DK); Thomas Michael Frimurer, Copenhagen S. (DK); Lars-Ole Gerlach, Vedbaek (DK)

(73) Assignees: DR. REDDY'S LABORATORIES LTD., Hyderabad (IN); DR. REDDY'S LABORATORIES, INC., Bridgewater, NJ (US)

( * ) Notice: Subject to any disclaimer, the term of this patent is extended or adjusted under 35 U.S.C. 154(b) by 255 days.

(21) Appl. No.: 13/811,020

(22) PCT Filed: Jul. 19, 2011

(86) PCT No.: PCT/US2011/044513
§ 371 (c)(1),
(2), (4) Date: Jul. 24, 2013

(87) PCT Pub. No.: WO2012/012410
PCT Pub. Date: Jan. 26, 2012

(65) Prior Publication Data
US 2013/0303525 A1 Nov. 14, 2013

Related U.S. Application Data

(60) Provisional application No. 61/435,980, filed on Jan. 25, 2011.

(30) Foreign Application Priority Data

Jul. 19, 2010 (IN) .......................... 2045/CHE/2010

(51) Int. Cl.
C07D 419/12 (2006.01)
C07D 207/09 (2006.01)
C07D 401/12 (2006.01)
C07D 403/12 (2006.01)
C07D 413/12 (2006.01)
C07D 413/14 (2006.01)
C07D 417/12 (2006.01)
C07D 207/12 (2006.01)
C07D 209/34 (2006.01)
C07D 213/76 (2006.01)
C07D 215/12 (2006.01)
(Continued)

(52) U.S. Cl.
CPC ............ *C07D 419/12* (2013.01); *C07D 207/09* (2013.01); *C07D 207/12* (2013.01); *C07D 209/34* (2013.01); *C07D 213/76* (2013.01); *C07D 215/12* (2013.01); *C07D 215/227* (2013.01); *C07D 231/56* (2013.01); *C07D 249/18* (2013.01); *C07D 261/20* (2013.01); *C07D 263/56* (2013.01); *C07D 263/58* (2013.01); *C07D 275/06* (2013.01); *C07D 277/30* (2013.01); *C07D 279/02* (2013.01); *C07D 295/13* (2013.01); *C07D 401/12* (2013.01); *C07D 403/12* (2013.01); *C07D 413/12* (2013.01); *C07D 413/14* (2013.01); *C07D 417/12* (2013.01)

(58) Field of Classification Search
None
See application file for complete search history.

(56) References Cited

U.S. PATENT DOCUMENTS 5,681,830 A 10/1997 Chang et al.
7,112,598 B2 9/2006 Tokai et al.
(Continued)

FOREIGN PATENT DOCUMENTS

EP 0663401 A1 7/1995

OTHER PUBLICATIONS

International Search Report, dated Mar. 27, 2012 for corresponding International Patent Application No. PCT/US2011/044513.
(Continued)

*Primary Examiner* — James D Anderson
(74) *Attorney, Agent, or Firm* — Pergament & Cepeda LLP; Milagros A. Cepeda; Edward D. Pergament

(57) ABSTRACT

The present invention relates to a series of substituted compounds having the general formula (I), including their stereoisomers and/or their pharmaceutically acceptable salts. (I) Wherein A, m, R1s, R2, R3, R4 are as defined herein. This invention also relates to methods of making these compounds including intermediates. The compounds of this invention are effective at the kappa (κ) opioid receptor (KOR) site. Therefore, the compounds of this invention are useful as pharmaceutical agents, especially in the treatment and/or prevention of a variety of central nervous system disorders (CNS), including but not limited to acute and chronic pain, and associated disorders, particularly functioning peripherally at the CNS.

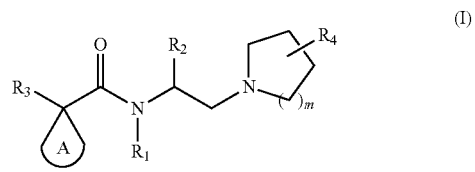

(I)

27 Claims, No Drawings

(51) Int. Cl.

| | |
|---|---|
| C07D 215/227 | (2006.01) |
| C07D 231/56 | (2006.01) |
| C07D 249/18 | (2006.01) |
| C07D 261/20 | (2006.01) |
| C07D 263/56 | (2006.01) |
| C07D 263/58 | (2006.01) |
| C07D 275/06 | (2006.01) |
| C07D 277/30 | (2006.01) |
| C07D 279/02 | (2006.01) |
| C07D 295/13 | (2006.01) |

(56) References Cited

U.S. PATENT DOCUMENTS

2005/0176746 A1  8/2005  Weber et al.
2008/0242720 A1  10/2008  Mangel

OTHER PUBLICATIONS

P. L. Wood, "Multiple Opiate Receptors: Support for Unique Mu, Delta and Kappa Sites", Neuropharmacology, 1982, pp. 487 to 497, vol. 21, Pergamon Press Ltd., Great Britain.
Eric J. Simon, "Opioid Receptors and Endogenous Opioid Peptides", Medicinal Research Reviews, 1991, pp. 357 to 374, vol. 11-issue No. 4, John Wiley & Sons, Inc.
Morley and Levine, "Involvement of Dynorphin and the Kappa Opioid Receptor in Feeding", Peptides, 1983, pp. 797 to 800, vol. 4, Ankho International Inc., USA.
Leander et al., "Diuresis and Suppression of Vasopressin by Kappa Oploids: Comparison with Mu and Delta Opioids and Clonidine", The Journal of Pharmacology and Experimental Therapeutics, 1985, pp. 463 to 469, vol. 234-issue No. 2, The American Society for Pharmacology and Experimental Therapeutics.
Neumeyer et al., "Kappa opioid agonists as targets for pharmacotherapies in cocaine abuse", Pharmaceutica Acta Helvetiae, 2000, pp. 337 to 344, vol. 74, Elsevier Science B.V.
Craft et al., "Kappa Opioid-Induced Diuresis in Female vs. Male Rats", Pharmacology Biochemistry and Behavior, 1999, pp. 53 to 59, vol. 65-issue No. 1, Elsevier Science Inc.
Richard D. Bodnar, "Endogenous opiates and behavior: 2007", Peptides, ScienceDirect, 2008, pp. 2292 to 2375, vol. 29, Elsevier Inc.
Walker et al., "Anti-Inflammatory Effects of Kappa-Opioids in Adjuvant Arthritis", Life Sciences, 1995, pp. 371 to 378, vol. 57-issue No. 4, Elsevier Science Inc.
Hudzik et al., "Antiparkinson potential of δ-opioid receptor agonists", European Journal of Pharmacology, 2000, pp. 101 to 107, vol. 396, Elsevier Science B.V.
Przewlochi and Przewlocha, "Opioids in chronic pain", European Journal of Pharmacology, 2001, pp. 79 to 91, vol. 429, Elsevier Science B.V.
Yamada et al., "The expression of mRNA for a kappa opioid receptor in the substantia nigra of Parkinson's disease brain", Molecular Brain Research, 1997, pp. 12 to 20, vol. 44, Elsevier Science B.V.
Bahrenberg et al., Pain Research, From Chemistry and Pharmacology to Clinical Application, 2002, Wiley-VCH Verlag GmbH & Co. KGaA, Weinheim, ISBN: 3-527-30403-7.
KK Jain, "A Guide to Drug Evaluation for Chronic Pain"; Emerging Drugs, 2000, pp. 241 to 257, vol. 5-issue No. 2, Ashley Publications, Inc.
Compound Summary for CID No. 16673831 cited in the ISR dated Mar. 27, 2012 for corresponding International Patent Application No. PCT/US2011/044513, PubChem, Aug. 17, 2007.
Compound Summary for CID No. 16672097, cited in the ISR dated Mar. 27, 2012 for corresponding International Patent Application No. PCT/US2011/044513, PubChem, Aug. 17, 2007.

KAPPA OPIOID RECEPTOR AGONISTS

This application is a National Stage Application under 35 U.S.C. 371 of PCT International Application No. PCT/US2011/044513, filed Jul. 19, 2011, which claims priority to Indian Provisional Applications 2045/CHE/2010, filed on Jul. 19, 2010; and U.S. Provisional Application No. 61/435,980, filed on Jan. 25, 2011; all of which are hereby incorporated by reference in their entirety.

FIELD OF THE INVENTION

The present invention relates to a series of heterocylic compounds of formula (I) as kappa (κ) opioid receptor (KOR) agonists. The present invention also relates to the preparation of compounds of formula (I). The present invention further relates to pharmaceutical compositions comprising compounds of formula (I).

BACKGROUND OF THE INVENTION

The endogenous opioid system comprises three principal opioid receptor sites in the central nervous system and in the periphery designated as μ (Mu), κ (Kappa) and δ (Delta). The pharmacological response is elicited by binding of a multitude of endogenous opioid ligands to these receptors, the principal ones being the enkephalins, endorphins, and dynorphins. The exogenous opioids/opiates exert their activity by mimicking and/or antagonizing the activity of the endogenous opioid ligands at these receptors. Since the anatomical location, distribution and function of the opioid receptors is wide and varied (Neuropharmacology, 21, 487-497; Med. Res. Rev., 11, 357-374), the pharmacological effects elicited by their agonism and antagonism are diverse as well.

The μ receptors which bind morphine and its derivatives are responsible for analgesia, respiratory and gastrointestinal functions, sedation, neuroendocrine functions and mediate opiate dependence. The δ receptors are abundant in the CNS and mediate analgesia, feeding and various hormonal functions. The κ receptors are widely distributed in the CNS, peripheral tissues, nerve endings, immune cells, etc., and are responsible for functions including analgesia, gastrointestinal functions like food intake, gut motility, water balance, thermoregulation and various neuroendocrine functions. (J. Pharmacol. Exp. Ther. 234, 463-469; Peptides 4, 797-800; Goodman and Gilman's The Pharmacological Basis of Therapeutics (11th Edition) Chapter 21, Pp 547-590). It should further be noted that the κ receptors are also widely distributed in peripheral tissues, nerve endings and immune cells, etc.

Pharmacologic studies with receptor selective ligands have shown that analgesia can be produced by selective activation of each of the three types of opioid receptors. Most clinically used opioid analgesics, such as morphine and codeine act as μ receptor agonists. These opioids are known to feature undesirable and potentially dangerous dependence forming side effects. The κ opioid receptors, on the other hand have attracted special attention because their selective activation can produce analgesia without causing dependence and respiratory depression that is typically associated with μ receptor activation by morphine (Pharmaceutica Acta Helvetiae, 74, 2-3, Pp 337-344).

The opioid receptors are members of the superfamily of G-protein-coupled receptors (GPCRs). An agonist binding to the κ receptor activates the intracellularly associated G protein, which decreases $Ca^{2+}$ channel conductance or inhibits adenylyl cyclase (AC). In addition to analgesia, potential applications of κ selective agonists include treating conditions, such as diuresis (Pharmacology Biochemistry and Behavior, 65, 1, Pp 53-59), eating disorders, motion sickness, and neuroprotection (Peptides 29, 12, Pp 2292-2375), among other disorders. Therefore, the κ receptors represent important therapeutic targets. Ligands selective for the κ receptors can serve as important pharmacologic tools. For example, such compounds can be used in competition assays to determine the relative specificity and selectivity of other compounds for the κ receptor, as well as for μ and δ receptors.

Various different classes of compounds featuring KOR agonist activity have been described in the art including the following:

U.S. Pat. No. 7,112,598 describes 2-phenylbenzothiazoline derivatives as KOR agonists.

U.S. Pat. No. 5,681,830 describes diarylmethyl piperazine compounds having utility as exogenous receptor combinant species for binding with opioid receptors such as kappa receptors.

European Patent No. 0 663 401 describes morphinan derivatives as selective KOR agonists and their application as an analgesic, diuretic, antitussive and brain cell protective agent.

The κ opioid receptor (also known as KOR) modulation has also been reported to be useful in the treatment of arthritis (Life Sciences, 57, 4, Pp 371-378), hypertension, pain, particularly pain which is inflammatory in origin and post-operative pain, (European Journal of Pharmacology, 429, 1-3, Pp 79-91) inflammation, migraine, inflammatory disorders of the gastrointestinal tract, psoriasis, and irritable bowel syndrome (IBS), Parkinsonism, (European Journal of Pharmacology, 396, 2-3, Pp 101-107, Molecular Brain Research, 44, 1, Pp 12-20) and stroke.

SUMMARY OF THE INVENTION

The present invention discloses compounds having the general formula (I) or a stereoisomer thereof or a pharmaceutically acceptable salt thereof:

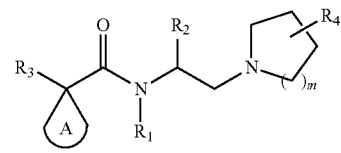

wherein,

A represents a 3-7 membered cycloalkyl ring;

$R_1$ represents hydrogen or alkyl;

$R_2$ represents hydroxyalkyl, haloalkyl, an optionally substituted group selected from alkyl, aryl, heteroaryl, cycloalkyl or heterocyclyl, wherein one or more substituents, independently, selected from —CN, hydroxyl, $NO_2$, —$NR_aR_b$, —$OR_c$, alkyl, aryl, aralkyl, heterocyclyl, heteroaryl, —$(CH_2)_nCOOR_d$ or —$(CH_2)_nCON(R_1)_2$;

$R_3$ represents an optionally substituted group selected from aryl, heterocyclyl, heteroaryl, wherein $R_3$ is optionally substituted one or more times with a substituent, independently selected from CN, hydroxyl, halogen, alkyl, haloalkyl, aryl, aralkyl, heterocyclyl, heteroaryl, —$(CH_2)_nNR_aR_b$, —$OR_c$, —$SO_2R^e$, —$SO_2N(R_1)_2$, —$COR_5$, —$C(R^e)$=N—OH, —$(CH_2)_qCOOR_d$ or

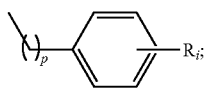

$R_4$ is selected from hydrogen, hydroxyl, halogen, hydroxyalkyl, —N(R$_1$)$_2$ or NR$_i$COOR$_c$;

$R_a$, in each occurrence, independently selected from hydrogen or alkyl;

$R_b$, in each occurrence, independently selected from alkyl, —COOR$_1$, —CO—R$_1$ or —SO$_2$—R$_e$; wherein R$_1$ is as defined above $R_e$, in each occurrence, independently selected from an optionally substituted group selected from alkyl, aryl, heteroaryl or heterocyclyl;

$R_c$, in each occurrence, independently selected from alkyl, aralkyl, —SO$_2$—R$_e$, —(CH$_2$)$_p$COOR$_d$, or

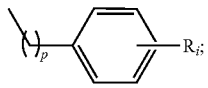

$R_i$, in each occurrence, independently selected from hydrogen, alkyl, alkoxy, haloalkyl, —CN, halogen, or —COOR$_d$;

$R_d$, in each occurrence, independently selected from hydrogen, an optionally substituted group selected from alkyl, aryl, heteroaryl or heterocyclyl;

$R_5$ represents alkyl or —N(R$_1$)$_2$;

m represents 0 or 1; and n, p and q, in each occurrence, independently selected from 0, 1, 2, 3 or 4.

The compounds of formula (I) may exist in the form of pharmaceutically acceptable salts. Such pharmaceutically acceptable salts are part of the invention.

The compounds of formula (I) may also exist in the form of stereoisomers and/or their pharmaceutically acceptable salts thereof. Such stereoisomers and/or their pharmaceutically acceptable salts are part of the invention.

DETAILED DESCRIPTION OF THE INVENTION

Reference will now be made in detail to the embodiments of the invention, one or more examples of which are set forth below. Each example is provided by way of explanation of the invention, and not by way of limitation of the invention. In fact, it will be apparent to those skilled in the art that various modification and variations can be made in the present invention without departing from the scope or spirit of the invention. For instance, features illustrated or described as part of one embodiment can be used on another embodiment to yield a still further embodiment. Thus it is intended that the present invention cover such modifications and variations as come within the scope of the appended claims and their equivalents. Other objects, features, and aspects of the present invention are disclosed in, or are obvious from, the following detailed description. It is to be understood by one of ordinary skill in the art that the present discussion is a description of exemplary embodiments only, and is not to be construed as limiting the broader aspects of the present invention.

The present invention relates to a series of heterocyclic compounds having the general formula (I):

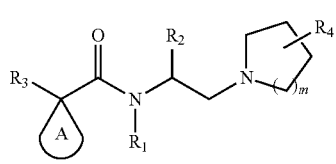

their stereoisomers and/or their pharmaceutically acceptable salts.

Wherein,

A represents a 3-7 membered cycloalkyl ring;

$R_1$, in each occurrence, independently represents hydrogen or alkyl;

$R_2$ represents hydroxyalkyl, haloalkyl, a optionally substituted group selected from alkyl, aryl, heteroaryl, cycloalkyl or heterocyclyl, wherein one or more substituents, independently, selected from —CN, hydroxyl, NO$_2$, —NR$_a$R$_b$, —OR$_c$, alkyl, aryl, aralkyl, heterocyclyl, heteroaryl, —CH$_2$)—COOR$_d$ or —(CH$_2$)$_n$CON(R$_1$)$_2$;

$R_3$ represents an optionally substituted group selected from aryl, heterocyclyl, heteroaryl; wherein one or more substituents, independently, selected from CN, hydroxyl, halogen, alkyl, haloalkyl, aryl, aralkyl, heterocyclyl, heteroaryl, —(CH$_2$)$_n$NR$_a$R$_b$, —OR$_c$, —SO$_2$R$^e$, —SO$_2$N(R$_1$)$_2$, —COR$_5$, —C(R$^e$)=N—OH, (CH$_2$)$_q$COOR$_d$ or

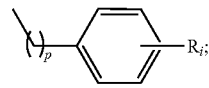

$R_4$, in each occurrence, independently selected from hydrogen, hydroxyl, halogen, hydroxyalkyl, —N(R$_1$)$_2$ or —NR$_1$COOR$_e$;

$R_a$, in each occurrence, independently selected from hydrogen or alkyl;

$R_b$, in each occurrence, independently selected from alkyl, —COOR$_1$, —CO—R$_1$ or —SO$_2$—R$_e$; wherein R$_1$ is as defined above;

$R_e$, in each occurrence, independently selected from an optionally substituted group selected from alkyl, aryl, heteroaryl or heterocyclyl;

$R_c$, in each occurrence, independently selected from alkyl, aralkyl, —SO$_2$—R$_e$, —(CH$_2$)$_p$COOR$_d$, or

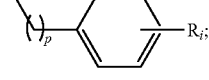

$R_i$, in each occurrence, independently selected from hydrogen, alkyl, alkoxy, haloalkyl, —CN, halogen, or —COOR$_d$;

$R_d$, in each occurrence, independently selected from hydrogen, an optionally substituted group selected from alkyl, aryl, heteroaryl or heterocyclyl;

$R_5$ represents alkyl or —N(R$_1$)$_2$;

m represents 0 or 1; and n, p and q, in each occurrence, independently selected from 0, 1, 2, 3 or 4.

In one embodiment, compounds of the invention are represented by the general formula (Ia):

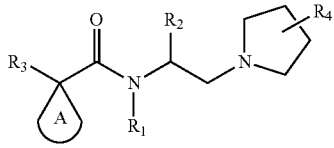

(Ia)

wherein $R_1$, $R_2$, $R_4$ and A are as defined above;
$R_3$ optionally substituted ring selected from:

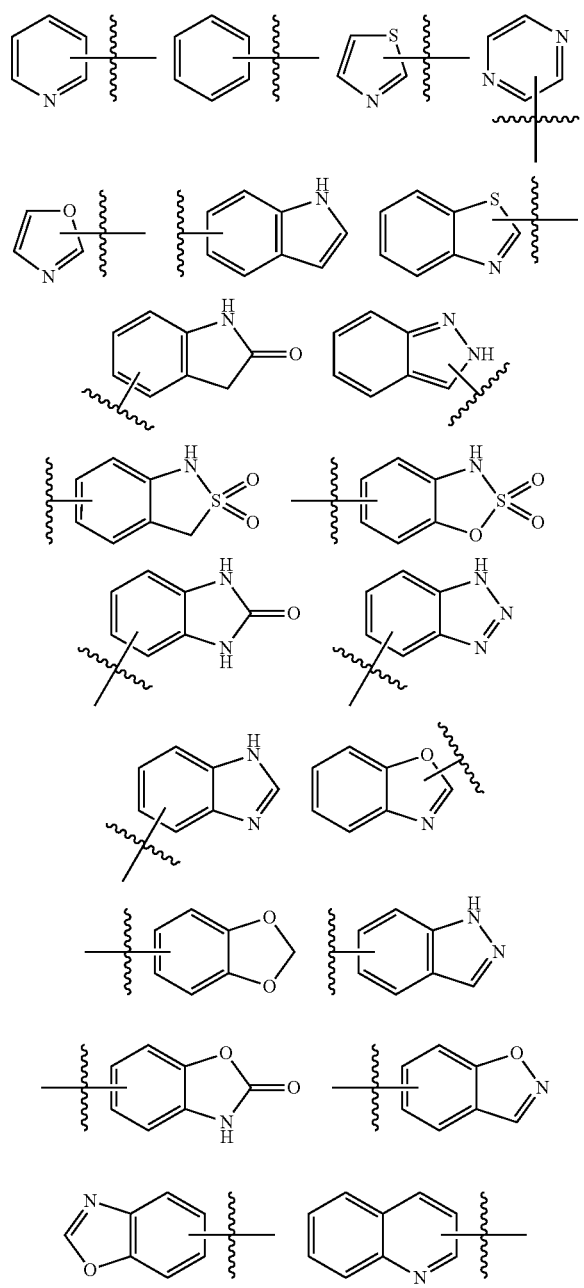

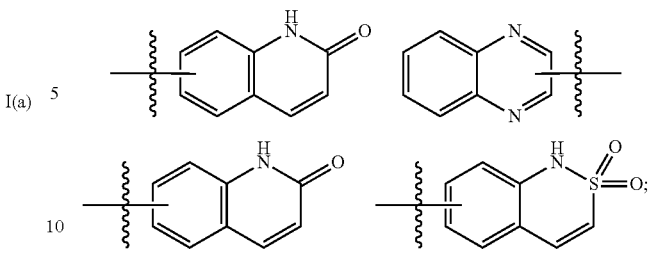

One or more substituents on $R_3$ are selected independently from CN, hydroxyl, halogen, alkyl, haloalkyl, aryl, aralkyl, heterocyclyl, heteroaryl, —$(CH_2)_nNR_aR_b$, —$OR_c$, —$SO_2R^e$, —$SO_2N(R_1)_2$, —$COR_5$, —$C(R^e)=N$—OH, $(CH_2)_qCOOR_d$ or

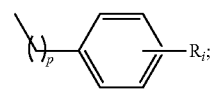

wherein $R_a$, $R_b$, $R_e$, $R_d$, $R_e$, $R_i$, $R_5$ and q are as defined in the description of formula (I) above.

In another embodiment, the compounds of the present invention are represented by the general formula (Ib):

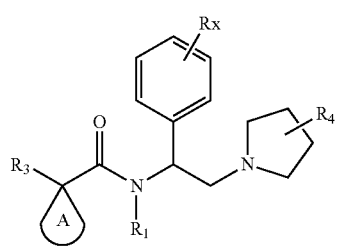

(Ib)

wherein A, $R_1$, $R_3$ & $R_4$ are as defined in the above description of formula (I);

$R_x$ represents —CN, hydroxyl, $NO_2$, —$NR_aR_b$, —$OR_c$, alkyl, aryl, aralkyl, heterocyclyl, heteroaryl, —$(CH_2)_nCOOR_d$ or —$(CH_2)_nCON(R_1)_2$; wherein $R_a$ represents hydrogen or alkyl;

$R_b$ represents alkyl, —$COOR_1$, CO—$R_1$ or —$SO_2$—$R_e$; wherein $R_1$ is as defined above and $R_e$ represents an optionally substituted group selected from alkyl, aryl, heteroaryl or heterocyclyl;

$R_c$ represents alkyl, aralkyl, —$SO_2$—$R_e$, —$(CH_2)_pCOOR_d$ or

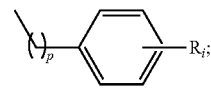

wherein $R_i$ is selected from hydrogen, —CN, halogen, alkyl, alkoxy, haloalkyl or —$COOR_d$; wherein $R_d$ represents hydrogen, an optionally substituted group selected from alkyl, aryl, heteroaryl or heterocyclyl;

n, p and q independently represent 0, 1, 2, 3 or 4;

R₃ is selected from optionally substituted

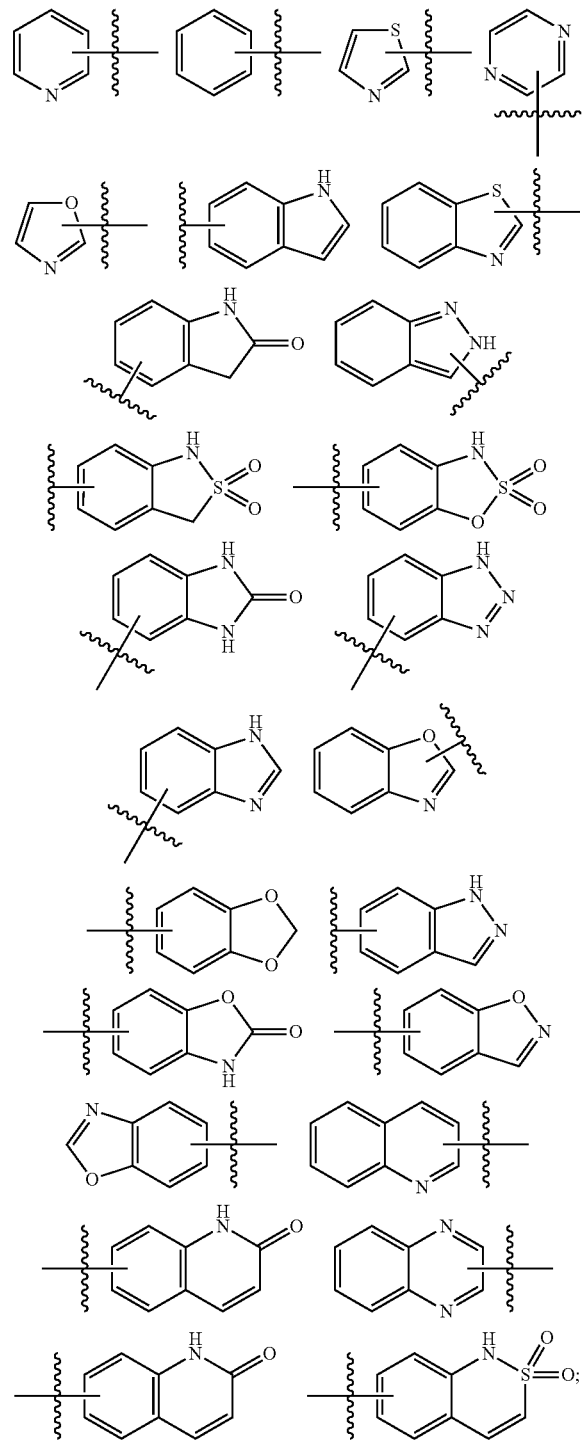

One or more substituents on R₃ are selected independently from CN, hydroxyl, halogen, alkyl, haloalkyl, aryl, aralkyl, heterocyclyl, heteroaryl, —(CH$_2$)$_n$NR$_a$R$_b$, —OR$_c$, —SO$_2$R$^e$, —SO$_2$N(R$_1$)$_2$, —COR$_5$, —C(R$^e$)=N—OH, (CH$_2$)$_q$COOR$_d$ or

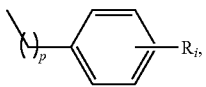

wherein R$_a$, R$_b$, R$_c$, R$_d$, R$_e$, R$_i$, and q are as above.

In one aspect of the above embodiment, R$_4$ represents hydrogen or hydroxyl.

In another embodiment, the compounds of formula (I) are those wherein

R$_2$ represents an optionally substituted alkyl, cycloalkyl, heteroaryl or heterocyclyl group, and wherein one or more optional substituents are selected from R$_x$;

R$_3$ is as defined in formula (Ib).

In one aspect of this embodiment, wherein R$_4$ represents hydrogen or hydroxyl.

In another aspect of formula (Ia) or (Ib), wherein R$_2$ represents an optionally substituted heteroaryl group.

In another aspect of formula (Ia) or (Ib), wherein R$_2$ represents an optionally substituted heterocyclyl group, In an embodiment, specific compounds of formula (I) without any limitation are enumerated as follows:

(S)-1-phenyl-N-(1-phenyl-2-(pyrrolidin-1-yl)ethyl)cyclopropanecarboxamide hydrochloride;

(S)—N-methyl-1-phenyl-N-(1-phenyl-2-(pyrrolidin-yl] ethyl]cyclopentanecarboxamide hydrochloride;

(S)—N-methyl-1-phenyl-N-(1-phenyl-2-(pyrrolidin-1-yl] ethyl]cyclohexane carboxamide hydrochloride;

(S)—N-methyl-1-phenyl-N-(1-phenyl-2-(pyrrolidin-1-yl] ethyl]cyclopropane carboxamide hydrochloride;

(S)—N-methyl-N-(1-phenyl-2-(pyrrolidin-1-yl)ethyl)-1-(quinolin-3-yl)cyclopropane carboxamide hydrochloride;

(S)-1-phenyl-N-(1-phenyl-2-(pyrrolidin-1-yl)ethyl)cyclohexane carboxamide hydrochloride;

(S)—N-(1-phenyl-2-(pyrrolidin-1-yl)ethyl)-1-(pyridin-3-yl)cyclopropane carboxamide hydrochloride;

(S)—N-(1-phenyl-2-(pyrrolidin-1-yl)ethyl)-1-(quinolin-3-yl)cyclopropane carboxamide hydrochloride;

(S)—N-(1-phenyl-2-(pyrrolidin-1-yl)ethyl)-1-(pyridin-2-yl)cyclopropane carboxamide hydrochloride;

N—((S)-2-((S)-3-hydroxypyrrolidin-1-yl)-1-phenylethyl)-1-(quinolin-3-yl)cyclopropane carboxamide hydrochloride;

(S)—N-(3-methyl-1-(pyrrolidin-1-yl) butan-2-yl)-1-(quinolin-3-yl)cyclopropane carboxamide hydrochloride;

(S)-1-(benzo[d]oxazol-2-yl)-N-(1-phenyl-2-(pyrrolidin-1-yl)ethyl)cyclopropane carboxamide;

(S)—N-(1-phenyl-2-(pyrrolidin-1-yl)ethyl)-1-(4-phenylthiazol-2-yl)cyclopropane carboxamide;

(S)-1-(benzo[d][1,3]dioxol-5-yl)-N-(1-phenyl-2-(pyrrolidin-1-yl)ethyl)cyclopropane carboxamide;

(S)-1-(benzo[d]thiazol-2-yl)-N-(1-phenyl-2-(pyrrolidin-1-yl)ethyl)cyclopropane carboxamide;

(S)-1-(3-cyanophenyl)-N-(1-phenyl-2-(pyrrolidin-1-yl) ethyl)cyclopropane carboxamide;

(S)—N-(2-(3-(hydroxymethyl) azetidin-1-yl)-1-phenylethyl)-1-(quinolin-3-yl)cyclopropane carboxamide;

(S)-1-(4-(methylsulfonamido)phenyl)-N-(1-phenyl-2-(pyrrolidin-1-yl)ethyl)cyclopropane carboxamide;

(S)-1-(3-(methylsulfonamido)phenyl)-N-(1-phenyl-2-(pyrrolidin-1-yl)ethyl)cyclopropane carboxamide;

(S)-1-(2-benzyl-2H-indazol-3-yl)-N-(1-phenyl-2-(pyrrolidin-1-yl)ethyl)cyclopropane carboxamide;

(S)—N-(1-phenyl-2-(pyrrolidin-1-yl)ethyl)-1-m-tolyl cyclopropane carboxamide hydrochloride;

(S)-1-(3-hydroxyphenyl)-N-(1-phenyl-2-(pyrrolidin-1-yl) ethyl)cyclopropane carboxamide hydrochloride;
(S)-1-(3-(benzyloxy)phenyl)-N-(1-phenyl-2-(pyrrolidin-1-yl)ethyl)cyclopropane carboxamide hydrochloride;
(S)—N-(2-(3-hydroxyazetidin-1-yl)-1-phenylethyl)-1-(quinolin-3-yl)cyclopropane carboxamide;
(S)-1-(3-(1H-tetrazol-5-yl)phenyl)-N-(1-phenyl-2-(pyrrolidin-1-yl)ethyl)cyclopropane carboxamide;
(S)-1-(3-cyanophenyl)-N-(3-methyl-1-(pyrrolidin-1-yl) butan-2-yl)cyclopropane carboxamide;
N—((S)-2-((S)-3-hydroxy pyrrolidin-1-yl)-1-phenyl ethyl)-1-(3-(methyl sulfonamido)phenyl)cyclopropane carboxamide;
(S)-4-(1-(1-phenyl-2-(pyrrolidin-1-yl)ethyl carbamoyl)cyclopropyl)phenyl methane sulfonate hydrochloride;
4-(1-((S)-2-((S)-3-hydroxypyrrolidin-1-yl)-1-phenylethylcarbamoyl)cyclopropyl)phenyl methanesulfonate hydrochloride;
(S)—N-(3-methyl-1-(pyrrolidin-1-yl) butan-2-yl)-1-(3-(methyl sulfonamido)phenyl)cyclopropane carboxamide;
3-(1-((S)-2-((S)-3-hydroxypyrrolidin-1-yl)-1-phenylethylcarbamoyl)cyclopropyl)phenyl methane sulfonate;
(S)-3-(1-(1-phenyl-2-(pyrrolidin-1-yl)ethyl carbamoyl)cyclopropyl)phenyl methane sulfonate;
N—((S)-2-((R)-3-fluoropyrrolidin-1-yl)-1-phenylethyl)-1-(quinolin-3-yl)cyclopropane carboxamide;
N—((S)-2-((R)-3-hydroxypyrrolidin-1-yl)-1-phenylethyl)-1-(quinolin-3-yl)cyclopropane carboxamide;
N—((S)-2-((R)-3-hydroxypyrrolidin-1-yl)-1-phenylethyl)-1-(3-(methyl sulfonamido)phenyl)cyclopropane carboxamide;
N—((S)-2-((S)-3-fluoro pyrrolidin-1-yl)-1-phenylethyl)-1-(quinolin-3-yl)cyclopropane carboxamide;
N—((S)-2-((S)-3-hydroxypyrrolidin-1-yl)-1-phenylethyl)-1-(3-isocyanophenyl)cyclopropane carboxamide;
N—((S)-2-((S)-3-hydroxy pyrrolidin-1-yl)-1-phenylethyl)-1-(quinoxalin-2-yl)cyclopropane carboxamide;
(S)—N-(1-phenyl-2-(pyrrolidin-1-yl)ethyl)-1-(quinoxalin-2-yl)cyclopropane carboxamide;
(S)—N-(1-phenyl-2-(pyrrolidin-1-yl)ethyl)-1-(pyridin-4-yl) cyclopropane carboxamide;
N—((S)-2-((S)-3-hydroxypyrrolidin-1-yl)-1-phenylethyl)-1-(pyridin-4-yl)cyclopropane carboxamide;
(S)-1-(4-(N,N-dimethylsulfamoyl)phenyl)-N-(1-phenyl-2-(pyrrolidin-1-yl)ethyl)cyclopropane carboxamide;
(S)-1-(4-(methylsulfonamidomethyl)phenyl)-N-(1-phenyl-2-(pyrrolidin-1-yl)ethyl)cyclopropane carboxamide;
N—((S)-2-((S)-3-hydroxypyrrolidin-1-yl)-1-phenyl ethyl)-1-(4-(methyl sulfonamide methyl)phenyl)cyclopropane carboxamide;
(S)-1-(3-(methylsulfonamidomethyl)phenyl)-N-(1-phenyl-2-(pyrrolidin-1-yl)ethyl)cyclopropane carboxamide;
N—((S)-2-((S)-3-hydroxypyrrolidin-1-yl)-1-phenyl ethyl)-1-(3-(methylsulfonamidomethyl)phenyl)cyclopropane carboxamide;
N—((S)-2-((S)-3-(dimethylamino)pyrrolidin-1-yl)-1-phenylethyl)-1-(3-(methylsulfonamido)phenyl)cyclopropanecarboxamide;
N—((S)-2-((S)-3-(dimethylamino)pyrrolidin-1-yl)-1-phenylethyl)-1-(quinolin-2-yl)cyclopropane carboxamide;
(S)-1-(4-(methylsulfonyl)phenyl)-N-(1-phenyl-2-(pyrrolidin-1-yl)ethyl)cyclopropane carboxamide;
(S)-1-(2-(N,N-dimethyl sulfamoyl)phenyl)-N-(1-phenyl-2-(pyrrolidin-1-yl)ethyl)cyclopropane carboxamide;
(S)-1-(3-(methylsulfonyl)phenyl)-N-(1-phenyl-2-(pyrrolidin-1-yl)ethyl)cyclopropane carboxamide hydrochloride;
(S)-1-(3-methoxyphenyl)-N-(1-phenyl-2-(pyrrolidin-1-yl) ethyl)cyclopropane carboxamide;
(S)-1-(2,2-dioxido-1,3-dihydrobenzo[c]isothiazol-5-yl)-N-(1-phenyl-2-(pyrrolidin-1-yl)ethyl)cyclopropane carboxamide;
(S)-1-(4-methoxyphenyl)-N-(1-phenyl-2-(pyrrolidin-1-yl) ethyl)cyclopropane carboxamide;
(S)-1-(2-oxo-1,2-dihydroquinolin-6-yl)-N-(1-phenyl-2-(pyrrolidin-1-yl)ethyl)cyclopropane carboxamide;
(S)-1-(4-chlorophenyl)-N-(1-phenyl-2-(pyrrolidin-1-yl) ethyl)cyclopropane carboxamide;
(S)-1-(4-chloro-3-(methyl sulfonamido)phenyl)-N-(1-phenyl-2-(pyrrolidin-1-yl)ethyl)cyclopropane carboxamide;
Tert-butyl (S)-1-((S)-2-(1-(3-(methylsulfonamido)phenyl) cyclopropane carboxamido)-2-phenylethyl)pyrrolidin-3-ylcarbamate;
N—((S)-2-((S)-3-(methyl amino)pyrrolidin-1-yl)-1-phenylethyl)-1-(3-(methylsulfonamido)phenyl)cyclopropane carboxamide;
N—((S)-2-((S)-3-amino pyrrolidin-1-yl)-1-phenyl ethyl)-1-(3-(methyl sulfonamido)phenyl)cyclopropane carboxamide 2,2,2-trifluoroacetate;
1-(2,2-Dioxo-2,3-dihydro-2-benzo[1,2,3]oxathiazol 5-yl)-cyclopropane carboxylic acid (1-phenyl-2-pyrrolidin-1-yl-ethyl)-amide;
1-(3-Dimethylsulfamoyl-phenyl)-cyclopropane carboxylic acid (1-phenyl-2-pyrrolidin-1-yl-ethyl)-amide;
1-(4-Sulfamoyl-phenyl)-cyclopropane carboxylic acid (1-phenyl-2-pyrrolidin-1-yl-ethyl)-amide;
1-(3-Acetyl-4-hydroxyphenyl)-cyclopropane carboxylic acid (1-phenyl-2-pyrrolidin-1-yl-ethyl)-amide;
1-(2-Oxo-2,3-dihydro-benzooxazol-5-yl)-cyclopropane carboxylic acid (1-phenyl-2-pyrrolidin-1-yl-ethyl)-amide;
1-(3-Methanesulfonylamino-phenyl)-cyclopropane carboxylic acid (1-benzyl-2-pyrrolidin-1-yl-ethyl)-amide;
1-(3-Methanesulfonylamino-phenyl)-cyclopropane carboxylic acid (1-pyridin-3-yl-2-pyrrolidin-1-yl-ethyl)-amide;
(S)—N-(1-cyclohexyl-2-(pyrrolidin-1-yl)ethyl)-1-(3-(methylsulfonamido)phenyl)cyclopropane carboxamide;
(S)—N-(4-methyl-1-(pyrrolidin-1-yl)pentan-2-yl)-1-(3-(methylsulfonamido)phenyl)cyclopropanecarboxamide;
(R)—N-(1-(3-(benzyloxy)phenyl)-2-(pyrrolidin-1-yl) ethyl)-1-(3-(methyl sulfonamido)phenyl)cyclopropanecarboxamide;
(R)—N-(1-(3-hydroxyphenyl)-2-(pyrrolidin-1-yl)ethyl)-1-(3-(methylsulfonamido)phenyl)cyclopropanecarboxamide;
(R)—N-(1-(3-methoxyphenyl)-2-(pyrrolidin-1-yl)ethyl)-1-(3-(methylsulfonamido)phenyl)cyclopropanecarboxamide;
1-(3-Methanesulfonylamino-4-methoxy-phenyl)-cyclopropane carboxylic acid (1-phenyl-2-pyrrolidin-1-yl-ethyl)-amide;
1-(3-Methyl-benzo[d]isoxazol-5-yl)-cyclopropane carboxylic acid (1-phenyl-2-pyrrolidin-1-yl-ethyl)-amide;
1-(6-Ethoxy-pyridin-2-yl)-cyclopropane carboxylic acid (1-phenyl-2-pyrrolidin-1-yl-ethyl)-amide;
1-(4-Methanesulfonylamino-3-methyl-phenyl)-cyclopropanecarboxylic acid (1-phenyl-2-pyrrolidin-1-yl-ethyl)-amide;
1-(3-Methanesulfonylamino-4-methyl-phenyl)-cyclopropane carboxylic acid (1-phenyl-2-pyrrolidin-1-yl-ethyl)-amide;
1-(3-Formylamino-4-hydroxy-phenyl)-cyclopropanecarboxylic acid (1-phenyl-2-pyrrolidin-1-yl-ethyl)-amide;

1-(4-Fluoro-3-methanesulfonylamino-phenyl)-cyclopropane carboxylic acid (1-phenyl-2-pyrrolidin-1-yl-ethyl)-amide;

1-(2,2-Dioxo-2,3-dihydro-1H-2-benzo[c]isothiazol-6-yl)-cyclopropane carboxylic acid (1-phenyl-2-pyrrolidin-1-yl-ethyl)-amide;

1-Benzooxazol-6-yl-cyclopropanecarboxylic acid (1-phenyl-2-pyrrolidin-1-yl-ethyl)-amide;

3-[1-(1-Phenyl-2-pyrrolidin-1-yl-ethylcarbamoyl)-cyclopropyl]-benzamide;

1-(2,4-Difluoro-5-methanesulfonylamino-phenyl)-cyclopropane carboxylic acid (1-phenyl-2-pyrrolidin-1-yl-ethyl)-amide;

1-[4-Hydroxy-3-(1-hydroxyimino-ethyl)-phenyl]-cyclopropane carboxylic acid (1-phenyl-2-pyrrolidin-1-yl-ethyl)-amide;

1-(2-Oxo-2,3-dihydro-1H-benzoimidazol-5-yl)-cyclopropane carboxylic acid (1-phenyl-2-pyrrolidin-1-yl-ethyl)-amide;

1-(1-Methyl-1H-benzotriazol-5-yl)cyclopropane carboxylic acid (1-phenyl-2-pyrrolidin-1-yl-ethyl)-amide;

1-(2-Oxo-1,2-dihydro-quinolin-7-yl)-cyclopropane carboxylic acid (1-phenyl-2-pyrrolidin-1-yl-ethyl)-amide;

{3-[1-(1-Phenyl-2-pyrrolidin-1-yl-ethylcarbamoyl)-cyclopropyl]-phenoxy}-acetic acid;

4-[1-(1-Phenyl-2-pyrrolidin-1-yl-ethylcarbamoyl)-cyclopropyl]-benzamide;

1-(2,2-Dioxo-1,2-dihydro-2,6-benzo[c][1,2]thiazin-7-yl)-cyclopropane carboxylic acid (1-phenyl-2-pyrrolidin-1-yl-ethyl)-amide;

1-(1H-Benzoimidazol-5-yl)-cyclopropanecarboxylic acid (1-phenyl-2-pyrrolidin-1-yl-ethyl)-amide;

1-(4-Fluoro-3-methanesulfonylamino-phenyl)-cyclopropane carboxylic acid (1-phenyl-2-pyrrolidin-1-yl-ethyl)-amide hydrochloride;

1-(4-Fluoro-3-methanesulfonylamino-phenyl)-cyclopropanecarboxylic acid [2-(3-hydroxy-pyrrolidin-1-yl)-1-phenyl-ethyl]-amide;

{4-[1-(1-Phenyl-2-pyrrolidin-1-yl-ethylcarbamoyl)-cyclopropyl]-phenoxy}-acetic acid;

(S)-1-(6-(methylsulfonamido)pyridin-3-yl)-N-(1-phenyl-2-(pyrrolidin-1-yl)ethyl)cyclopropanecarboxamide;

(S)-1-(2,2-dioxido-1H-benzo[c][1,2]thiazin-6-yl)-N-(1-phenyl-2-(pyrrolidin-1-yl)ethyl)cyclopropanecarboxamide;

(S)-1-(1H-indazol-5-yl)-N-(1-phenyl-2-(pyrrolidin-1-yl)ethyl)cyclopropanecarboxamide;

(S)-1-(benzo[d]isoxazol-5-yl)-N-(1-phenyl-2-(pyrrolidin-1-yl)ethyl)cyclopropane carboxamide;

(S)-3-(1-(1-phenyl-2-(pyrrolidin-1-yl)ethylcarbamoyl)cyclopropyl)benzoic acid;

(S)—N-(1-(3-methoxyphenyl)-2-(pyrrolidin-1-yl)ethyl)-1-(2-oxo-2,3-dihydrobenzo[d]oxazol-5-yl)cyclopropanecarboxamide;

N—((S)-2-((S)-3-hydroxypyrrolidin-1-yl)-1-phenylethyl)-1-(2-oxo-2,3-dihydrobenzo[d]oxazol-5-yl)cyclopropanecarboxamide;

(S)-tert-butyl 2-(2-oxo-5-(1-(1-phenyl-2-(pyrrolidin-1-yl)ethylcarbamoyl)cyclopropyl)benzo[d]oxazol-3 (2H)-yl)acetate;

(S)-2-(2-oxo-5-(1-(1-phenyl-2-(pyrrolidin-1-yl)ethylcarbamoyl)cyclopropyl)benzo[d]oxazol-3(2H)-yl)acetic acid hydrochloride;

(S)—N-(1-cyclohexyl-2-(pyrrolidin-1-yl)ethyl)-1-(2-oxo-2,3-dihydrobenzo[d]oxazol-5-yl)cyclopropanecarboxamide;

(S)-1-(3-methyl-1H-indazol-5-yl)-N-(1-phenyl-2-(pyrrolidin-1-yl)ethyl)cyclopropane carboxamide (S)—N-(1-(3-methoxyphenyl)-2-(pyrrolidin-1-yl)ethyl)-1-(3-methyl-1H-indazol-5-yl)cyclopropanecarboxamide;

(S)-4-(1-(1-phenyl-2-(pyrrolidin-1-yl)ethyl carbamoyl)cyclopropyl)benzoic acid;

(S)-1-(3-methyl-2-oxo-2,3-dihydrobenzo[d]oxazol-5-yl)-N-(1-phenyl-2-(pyrrolidin-1-yl)ethyl)cyclopropanecarboxamide;

N—((S)-1-cyclohexyl-2-((S)-3-hydroxypyrrolidin-1-yl)ethyl)-1-(2-oxo-2,3-dihydrobenzo[d]oxazol-5-yl)cyclopropanecarboxamide;

(S)—N-(1-(3-cyanophenyl)-2-(pyrrolidin-1-yl)ethyl)-1-(2-oxo-2,3-dihydrobenzo[d]oxazol-5-yl)cyclopropanecarboxamide;

(S)-3-(1-(1-(2-oxo-2,3-dihydrobenzo[d]oxazol-5-yl)cyclopropanecarboxamido)-2-(pyrrolidin-1-yl)ethyl)benzamide;

(S)-2-(3-(1-(1-(3-(methylsulfonamido)phenyl)cyclopropanecarboxamido)-2-(pyrrolidin-1-yl)ethyl)phenoxy)acetic acid;

(S)—N-(1-(3-(benzyloxy)phenyl)-2-(pyrrolidin-1-yl)ethyl)-1-(2-oxo-2,3-dihydrobenzo[d]oxazol-5-yl)cyclopropanecarboxamide;

(S)—N-(1-(3-hydroxyphenyl)-2-(pyrrolidin-1-yl)ethyl)-1-(2-oxo-2,3-dihydrobenzo[d]oxazol-5-yl)cyclopropanecarboxamide;

(S)-1-(4-cyanophenyl)-N-(1-phenyl-2-(pyrrolidin-1-yl)ethyl)cyclopropanecarboxamide;

(S)-3-(1-(1-(2-oxo-2,3-dihydrobenzo[d]oxazol-5-yl)cyclopropanecarboxamido)-2-(pyrrolidin-1-yl)ethyl)phenyl methanesulfonate 2,2,2-trifluoroacetate;

(S)—N-(1-(3-(2H-tetrazol-5-yl)phenyl)-2-(pyrrolidin-1-yl)ethyl)-1-(2-oxo-2,3-dihydrobenzo[d]oxazol-5-yl)cyclopropanecarboxamide;

N—((S)-2-((S)-3-hydroxypyrrolidin-1-yl)-1-(3-methoxyphenyl)ethyl)-1-(2-oxo-2,3-dihydrobenzo[d]oxazol-5-yl)cyclopropanecarboxamide;

(S)-methyl 4-((5-(1-(1-(3-hydroxyphenyl)-2-(pyrrolidin-1-yl)ethylcarbamoyl)cyclopropyl)-2-oxobenzo[d]oxazol-3 (2H)-yl)methyl)benzoate;

(S)-methyl 3-((5-(1-(1-(3-hydroxyphenyl)-2-(pyrrolidin-1-yl)ethylcarbamoyl)cyclopropyl)-2-oxobenzo[d]oxazol-3 (2H)-yl)methyl)benzoate;

N—((S)-1-(3-hydroxyphenyl)-2-(S)-3-hydroxypyrrolidin-1-yl)ethyl)-1-(2-oxo-2,3-dihydrobenzo[d]oxazol-5-yl)cyclopropanecarboxamide;

N—((S)-2-((S)-3-hydroxypyrrolidin-1-yl)-1-(3-nitrophenyl)ethyl)-1-(2-oxo-2,3-dihydrobenzo[d]oxazol-5-yl)cyclopropanecarboxamide;

(S)—N-(1-(3-aminophenyl)-2-(pyrrolidin-1-yl)ethyl)-1-(2-oxo-2,3-dihydrobenzo[d]oxazol-5-yl)cyclopropanecarboxamide;

(S)-1-(2-oxoindolin-6-yl)-N-(1-phenyl-2-(pyrrolidin-1-yl)ethyl)cyclopropanecarboxamide;

(S)—N-(1-(3-(3-cyanobenzyloxy)phenyl)-2-(pyrrolidin-1-yl)ethyl)-1-(2-oxo-2,3-dihydrobenzo[d]oxazol-5-yl)cyclopropanecarboxamide;

(S)—N-(1-(3-(4-cyanobenzyloxy)phenyl)-2-(pyrrolidin-1-yl)ethyl)-1-(2-oxo-2,3-dihydrobenzo[d]oxazol-5-yl)cyclopropanecarboxamide;

1-(2-Oxo-2,3-dihydrobenzo[d]oxazol-5-yl)-N-(2-(pyrrolidin-1-yl)-1-(tetrahydro-2H-pyran-4-yl)ethyl)cyclopropanecarboxamide;

N-(1-(1-benzyl-1H-pyrazol-4-yl)-2-(pyrrolidin-1-yl)ethyl)-1-(2-oxo-2,3-dihydrobenzo[d]oxazol-5-yl)cyclopropane carboxamide;

(S)-methyl-3-(2-oxo-5-(1-(1-phenyl-2-(pyrrolidin-1-yl)ethylcarbamoyl)cyclopropyl)benzo[d]oxazol-3(2H)-yl)methyl)benzoate;

(S)—N-(1-(3-(methylsulfonamido)phenyl)-2-(pyrrolidin-1-yl)ethyl)-1-(2-oxo-2,3-dihydrobenzo[d]oxazol-5-yl)cyclopropanecarboxamide, and (S)—N-methyl-1-phenyl-N-(1-phenyl-2-(pyrrolidin-1-yl)ethyl]cyclobutane carboxamide hydrochloride; and stereoisomers thereof and/or pharmaceutically acceptable salts thereof.

The compounds of formula (I) may exist in the form of pharmaceutically acceptable salts. Such pharmaceutically acceptable salts are also a part of the invention.

The compounds of formula (I) may also exist in the form of stereoisomers and/or their pharmaceutically acceptable salts. Such stereoisomers and/or their pharmaceutically acceptable salts are part of the invention.

In another embodiment, the invention is directed to pharmaceutical compositions comprising a pharmaceutically acceptable carrier and a therapeutically effective amount of one or more compounds of formula (I) or a stereoisomer thereof or a pharmaceutically acceptable salt thereof.

In another embodiment, the invention provides pharmaceutical compositions comprising a compound of formula (I) or any one or more of the specific compounds as enumerated hereinabove or a stereoisomer thereof or a pharmaceutically acceptable salt thereof.

In one embodiment, the present invention provides compounds of formula (I) as is opioid receptor (KOR) agonists or any one or more of the specific compounds as enumerated hereinabove or a stereoisomer thereof or a pharmaceutically acceptable salt thereof.

In another embodiment, the invention is directed to a method of administering KOR agonists in a subject (i.e., a patient), which comprises administering to said subject (i.e., a patient) a composition comprising a therapeutically effective amount of a compound of formula (I). As used herein the term "subject" and "patient" can be the same and can be used interchangeably.

In another embodiment, the invention is directed to a method of administering KOR agonists in a subject peripherally to the central nervous system, which comprises administering to said subject a composition comprising an effective amount of a compound of formula (I) or any one or more of the specific compounds as enumerated hereinabove or a stereoisomer thereof or a pharmaceutically acceptable salt thereof.

In another embodiment, the invention is directed to a method for binding opioid receptors in a patient in need thereof, comprising administering to said patient a composition comprising an effective amount of a compound of formula (I) or any one or more of the specific compounds as enumerated hereinabove or a stereoisomer thereof or a pharmaceutically acceptable salt thereof.

In other embodiments, the invention is directed to methods of treating or preventing gastrointestinal dysfunction, in a patient in need thereof, comprising administering to said patent a composition comprising an effective amount of a compound of formula (I) or any one or more of the specific compounds as enumerated hereinabove or a stereoisomer thereof or a pharmaceutically acceptable salt thereof.

In yet other embodiment, the invention is directed to methods of treating or preventing pain, to a patient in need thereof, comprising administering to said patent a composition comprising an effective amount of a compound of formula (I) or any one or more of the specific compounds as enumerated hereinabove or a stereoisomer thereof or a pharmaceutically acceptable salt thereof.

In another embodiment, the pain is selected from chronic pain or acute pain.

In yet another embodiment, the pain is selected from the group consisting of nociceptive pain, inflammatory pain, visceral pain, somatic pain, neuralgia, neuropathic pain, pain caused by autoimmune disorders (AIDS), pain due to cancer, phantom pain, psychogenic pain, pain resulting from hyperalgesia, pain caused by rheumatoid arthritis, migraine and allodynia.

In yet other embodiment, the invention is directed to methods of treating or preventing ileus in a patient in need thereof, comprising administering to said patent a composition comprising an effective amount of a compound of formula (I) or any one or more of the specific compounds as enumerated hereinabove or a stereoisomer thereof or a pharmaceutically acceptable salt thereof.

In yet another embodiment, the compounds of formula (I) are directed to the use in treating or preventing diseases or disorders that may be associated with and/or modulated by opioid receptors.

Another embodiment provides a method, wherein the compound of formula (I) binds κ opioid receptors.

Another embodiment provides a method, wherein the κ opioid receptors are located in the central nervous system.

Another embodiment provides a method, wherein the κ opioid receptors are located peripherally.

In an embodiment, the compounds of the present invention act peripherally to the central nervous system.

In another embodiment, the invention is directed to methods of treating or preventing arthritis, hypertension, post-operative pain, inflammation, migraine, disorders of gastrointestinal tract, psoriasis, Parkinsonism and stroke, comprising administering to a patient in need thereof, a composition comprising an effective amount of a compound of formula (I).

In another embodiment, the compounds of the present invention do not substantially cross the blood-brain barrier.

In certain of the embodiments, the compounds of the invention may be used in methods for preventing or treating post-operative or opioid-induced ileus.

As used herein and in the appended claims, the singular forms "a", "an", and "the" include plural reference unless the context clearly indicates otherwise. Thus, for example, reference to a "compound" is a reference to one or more such compounds and includes equivalents thereof known to those skilled in the art, and so forth.

Unless defined otherwise, all technical and scientific terms used herein have the same meaning as commonly understood to one of ordinary skill in the art at the time this invention was made.

'Halogen' represents fluorine, chlorine, bromine, or iodine.

'Alkyl' group refers to linear or branched alkyl groups. Exemplary alkyl groups include one or more of, but are not limited to, methyl, ethyl, n-propyl, iso-propyl, n-butyl, iso-butyl, t-butyl, n-pentyl, iso-pentyl, hexyl, heptyl, octyl and the like. Unless otherwise specified, an alkyl group typically contains from 1 to 10 carbon atoms.

"Alkoxy" group refers to an —O(alkyl) group, wherein alkyl is as defined herein. Exemplary alkoxy groups include methoxy, ethoxy, n-propoxy, iso-propoxy, n-butoxy, iso-butoxy, t-butoxy, and the like. Unless otherwise specified, an alkoxy group has from 1 to 10 carbon atoms.

'Hydroxyalkyl' refers to a group in which at least one hydrogen atom of an alkyl group is replaced by a hydroxyl group. Alkyl group is as defined above. Representative examples of hydroxyalkyl groups include, but are not limited to hydroxymethyl, hydroxyethyl and the like. Unless otherwise specified, a hydroxyalkyl group typically has from 1 to 10 carbon atoms.

'Haloalkyl' refers to a group in which at least one halogen atom is substituted on an alkyl group. Both halogen and alkyl are as defined above. Representative examples of haloalkyl groups include, but are not limited to, fluoromethyl, chloromethyl, fluoroethyl, chloroethyl, difluoromethyl, trifluoromethyl, dichloroethyl, trichloroethyl and the like. Unless otherwise specified, a haloalkyl group typically has from 1 to 10 carbon atoms.

'Cycloalkyl' group refers to a cyclic alkyl group, which may be mono, bicyclic, polycyclic, or a fused/bridged ring system. Exemplary cycloalkyl groups include, but are not limited to, cyclopropyl, cyclobutyl, cyclopentyl, cyclohexyl, cycloheptyl, cyclooctyl, and the like. Unless otherwise specified, a cycloalkyl group typically has from 3 to about 10 carbon atoms. Typical bridged cycloalkyls include, but are not limited to, adamantyl, noradamantyl, bicyclo[1.1.0]butanyl, norbornyl(bicyclo[2.2.1]heptanyl), norbornenyl (bicyclo[2.2.1]heptanyl), norbornadienyl(bicyclo[2.2.1]heptadienyl), bicyclo[2.2.1]heptanyl, bicyclo[3.2.1]octanyl, bicyclo[3.2.1]octadienyl, bicyclo[2.2.2]octanyl, bicyclo[2.2.2]octenyl, bicyclo[2.2.2]octadienyl, bicyclo[5.2.0]nonanyl, bicyclo[4.3.2]undecanyl, tricyclo[5.3.1.1]dodecanyl and the like.

'3-7 membered cycloalkyl ring' refers to a monocyclic alkyl group with 3-7 ring. Exemplary '3- to 7-membered cycloalkyl' ring include, but are not limited to, cyclohexyl, cyclobutyl, cyclopropyl, cyclopentyl and the like.

'Aryl' refers to a monocyclic or polycyclic aromatic ring system. Exemplary aryl groups include, but are not limited to, phenyl, naphthyl and the like. Unless otherwise specified, an aryl group typically has from 6 to 14 carbon atoms.

'Aralkyl' or 'arylalkyl' means an aryl-alkyl-group in which the aryl and alkyl are as previously described. Preferred aralkyls comprise a lower alkyl group. Non-limiting examples of suitable aralkyl groups include benzyl, 2-phenethyl and naphthalenylmethyl. The bond to the parent moiety is through the alkyl.

'Heterocyclyl' refers to a saturated monocyclic or polycyclic ring system of 3 to 10 members having at least one heteroatom or heterogroup selected from one or more of —O—, —N—, —S—, —SO$_2$, or —CO. Exemplary heterocyclyl groups include, but not limited to, azetidinyl, pyrrolidinyl, piperidinyl, piperazinyl, morpholinyl, thiomorpholinyl, thiomorpholine-1,1-dioxide, thiazolidinyl, 1,3-dioxolanyl, 1,4-dioxanyl, and the like. Unless otherwise specified, a heterocyclyl group typically has from 3 to about 10 carbon atoms.

'Heteroaryl' is an unsaturated, aromatic or non-aromatic, monocyclic or polycyclic ring system of 3 to 10 members having at least one heteroatom or heterogroup selected from one or more of —O—, —N—, —S—, —SO$_2$, or —CO where R$_a$ is H, alkyl or a bond. Exemplary heteroaryl groups include, but not limited to, oxazolyl, thiazolyl, pyridinyl, thiazinyl, pyrazinyl, pyrazolyl, tetrazolyl, imidazothiazolyl, indolizidinyl, indolyl, oxoindolyl, quinolinyl, quinoxalinyl, benzoxazolyl, benzo[d]isoxazolyl, benzo[d]thiazolyl, benzo[d][1,3]dioxolyl, 1H-benzo[d][1,2,3]triazolyl, 2-H-indazolyl, 1-H-indazolyl, quinoxalin-2-yl, benzo[d]oxazol-2(3H)-one, 1H-benzo[d]imidazolyl, quinolin-2(1H)-one, 1,3-dihydrobenzo[c]isothiazole-2,2-dioxide, 1H-benzo[d][1,2,3]triazole, 2-oxo-1,2-dihydroquinolin-6-yl, 3H-benzo[d][1,2,3]oxathiazole-2,2-dioxide, 1H-benzo[d]imidazol-2(3H)-one, 1H-benzo[c][1,2]thiazine-2,2-dioxide, 3,3a-dihydro-1H-indol-2(7aH)-one, 2-oxo-2,3-dihydrobenzo[d]oxazol-5-yl, and the like. Unless otherwise specified, a heteroaryl group typically has from 3 to about 10 carbon atoms.

The KOR may be an animal or a mammalian or non-mammalian receptor, such as a human receptor.

'Optionally substituted' means that substitution is optional and therefore it is possible for the designated atom or molecule to be unsubstituted. In the event a substitution is desired, then such substitution means that any number of hydrogens on the designated atom is replaced with a selection from the indicated group, provided that the normal valence of the designated atom is not exceeded, and that the substitution results in a stable compound. For example, in formula (I) when a substituent is keto (i.e., =O), then 2 hydrogens on the atom are replaced and when the substitution is fluoro, then 1 hydrogen on the atom is replaced and the like.

'Salts' refer to any acid or base salt, pharmaceutically acceptable solvates, or any complex of the compound that, when administered to a recipient, is capable of providing (directly or indirectly) a compound as described herein. It should be appreciated, however, that salts that are not pharmaceutically acceptable also lie within the scope of the invention. The preparation of salts can be carried out using known methods.

For example, pharmaceutically acceptable salts of compounds contemplated herein may be synthesized by conventional chemical methods using a parent compound containing an acid residue. Generally, such salts may be prepared, for example, by making free acid of the compounds and reacting with a stoichiometric quantity of the appropriate base or acid in water or in an organic solvent, or in a mixture of the two. Generally, non-aqueous media such as one or more of ether, ethyl acetate, ethanol, isopropanol or acetonitrile may be utilized. Examples of acid addition salts include one or more of, but are not limited to, acid addition salts such as hydrochloride, hydrobromide, hydroiodide, sulfate, nitrate, phosphate, trifluoroacetate, and organic acid addition salts such as acetate, maleate, fumarate, citrate, oxalate, succinate, tartarate, malate, mandelate, methanesulfonate and p-toluenesulfonate. Also included in present invention are the isomeric forms and tautomers and the pharmaceutically-acceptable salts of compounds of formula (I). Illustrative pharmaceutically acceptable salts are prepared from formic, acetic, propionic, succinic, glycolic, gluconic, lactic, malic, tartaric, citric, ascorbic, glucuronic, maleic, fumaric, pyruvic, aspartic, glutamic, benzoic, anthranilic, mesylic, stearic, salicylic, p-hydroxybenzoic, phenylacetic, mandelic, embonic (pamoic), methanesulfonic, ethanesulfonic, benzenesulfonic, pantothenic, toluenesulfonic, 2-hydroxyethanesulfonic, sulfanilic, cyclohexylaminosulfonic, algenic, β-hydroxybutyric, galactaric, and galacturonic acids.

For any particular compound disclosed herein, any general structure presented also encompasses all conformational isomers, regioisomers, stereoisomers and tautomers that may arise from a particular set of substituents.

Compounds of the invention, such as a compound of formula (I) and salts thereof, also include other forms, such as their stereoisomers (except where specifically indicated), prodrugs, hydrates, solvates, acid salt hydrates, or any isomorphic crystalline forms thereof.

Compounds employed in the methods and compositions of the present invention may exist in prodrug form. As used herein, "prodrug" is intended to include any covalently bonded carriers which release the active parent drug, for example, the compound of Formula (I), or other formulas or compounds employed in the present methods and compositions in vivo when such prodrug is administered to a mammalian subject. The term "prodrug" also includes compounds which may be specifically designed to maximize the amount of active species that reaches the desired site of reaction and which themselves may be inactive or minimally active for the activity desired, but through biotransformation are converted into biologically active metabolites. Since prodrugs are known to enhance numerous desirable qualities of pharmaceuticals (e.g., solubility, bioavailability, manufacturing, etc.) the compounds employed in the present methods may, if desired, be delivered in prodrug form. Thus, the present invention contemplates methods of delivering prodrugs. Prodrugs of the compounds employed in the present invention, for example a compound of Formula (I), may be prepared by modifying functional groups present in the compound in such a way that the modifications are cleaved, either in routine manipulation or in vivo, to the parent compound.

Accordingly, prodrugs include, for example, compounds described herein in which a hydroxy, amino, or carboxy group is bonded to any group that, when the prodrug is administered to a mammalian subject, cleaves to form a free hydroxyl, free amino, or carboxylic acid, respectively. Examples include, but are not limited to, acetate, formate and benzoate derivatives of alcohol and amine functional groups; and alkyl, carbocyclic, aryl, and alkylaryl esters such as methyl, ethyl, propyl, iso-propyl, butyl, isobutyl, sec-butyl, tert-butyl, cyclopropyl, phenyl, benzyl, and phenethyl esters, and the like.

Compound of formula (I) contains one or more asymmetric carbons. It is to be understood accordingly that the stereoisomers arising from such asymmetry (e.g., all enantiomers and diastereomers) are included within the scope of this invention, unless explicitly indicated otherwise. Such isomers can be obtained in substantially pure form by classical separation techniques and by stereochemically controlled synthesis.

As used herein, the term 'subject' or 'patient' means mammals, such as humans and other animals, including horses, dogs, cats, rats, mice, sheep, pigs, etc. In exemplary embodiments, the subject may include subjects for which treatment and/or prevention of the conditions described herein would be beneficial.

For ease of reference, the present invention will be described in terms of administration to human subjects. It will be understood, however, that such descriptions are not limited to administration to humans, but will also include administration to other animals unless explicitly stated otherwise.

The phrase "side effect" refers to a consequence other than the one(s) for which an agent or measure is used, as the adverse effects produced by a drug, especially on a tissue or organ system other than the one sought to be benefited by its administration. In the case, for example, of opioids, the term "side effect" may refer to such conditions as, for example, constipation, nausea and/or vomiting.

The phrase "therapeutically effective amount" refers to an amount of a compound as described herein that may be therapeutically effective to inhibit, prevent or treat the symptoms of particular disease, disorder or side effect. Such diseases, disorders and side effects include, but are not limited to, those pathological conditions associated with the administration of opioids (for example, in connection with the treatment and/or prevention of pain), wherein the treatment or prevention comprises, for example, inhibiting the activity thereof by contacting cells, tissues or receptors with compounds of the present invention. Thus, for example, the term "therapeutically effective amount", when used in connection with opioids, for example, for the treatment of pain, refers to the treatment and/or prevention of the painful condition. The term "therapeutically effective amount", when used in connection with opioid antagonist compounds, refers to the treatment and/or prevention of side effects typically associated with opioids including, for example, such side effects as constipation, nausea and/or vomiting, as well as other side effects, discussed in further detail below.

The terms 'treating' or 'to treat' means to alleviate symptoms, eliminate the causation either on a temporary or permanent basis, or to prevent or slow the appearance of symptoms. The term 'treatment' includes alleviation, elimination of causation of or prevention of any of the diseases or disorders described above. Besides being useful for human treatment, these combinations are also useful for treatment of other mammals, including horses, dogs, cats, rats, mice, sheep, pigs, etc.

"Pain" refers to the perception or condition of unpleasant sensory or emotional experience, associated with actual or potential tissue damage or described in terms of such damage. "Pain" includes, but is not limited to, two broad categories of pain: acute and chronic pain. Buschmann, H.; Christoph, T; Friderichs, E.; Maul, C.; Sundermann, B; eds.; Analgesics, Wiley-VCH, Verlag GMbH & Co. KgaA, Weinheim; 2002; Jain, K. K., "A Guide to Drug Evaluation for Chronic Pain"; Emerging Drugs, 5(2), 241-257 (2000), the disclosures of which are hereby incorporated herein by reference in their entireties. Non-limiting examples of pain include, for example, nociceptive pain, inflammatory pain, visceral pain, somatic pain, neuralgias, neuropathic pain, AIDS pain, cancer pain, phantom pain, and psychogenic pain, and pain resulting from hyperalgesia, pain caused by rheumatoid arthritis, migraine, allodynia and the like.

The term "gastrointestinal dysfunction", as used herein, refers collectively to maladies of the gastrointestinal system, particularly the stomach and small and large intestines. Non-limiting examples of gastrointestinal dysfunction include, for example, diarrhea, nausea, emesis, post-operative emesis, opioid-induced emesis, irritable bowel syndrome, opioid-bowel dysfunction, opioid induced constipation, ileus, including post-operative ileus, post-partum ileus and opioid-induced ileus, colitis, decreased gastric motility, decreased gastric emptying, inhibition of small intestinal propulsion, inhibition of large intestinal propulsion, increased amplitude of non-propulsive segmental contractions, constriction of sphincter of Oddi, increased anal sphincter tone, impaired reflex relaxation with rectal distention, diminished gastric, biliary, pancreatic or intestinal secretions, increased absorption of water from bowel contents, gastro-esophageal reflux, gastroparesis, cramping, bloating, distension, abdominal or epigastric pain and discomfort, non-ulcerogenic dyspepsia, gastritis, constipation, or delayed absorption of orally administered medications or nutritive substances.

The term "peripheral" designates that the compound acts primarily on physiological systems and components external to the central nervous system (CNS). In preferred form, the peripheral opioid antagonist compounds employed in the methods of the present invention exhibit high levels of activity with respect to peripheral tissue, such as, gastrointestinal tissue, while exhibiting reduced, and substantially no CNS activity at therapeutically relevant doses.

The phrase "substantially no CNS activity," as used herein, means that less than about 20% of the pharmacological activity of the compounds employed in the present methods is exhibited in the CNS, less than about 15%, less than about 10%, less than about 5% and non-detectable, de minimus, or even 0% of the pharmacological activity of the compounds employed in the present methods is exhibited in the CNS.

The phrase "does not substantially cross," as used herein, means that less than about 20% by weight of the compound employed in the present methods crosses the blood-brain barrier, preferably less than about 15% by weight, more preferably less than about 10% by weight, even more preferably less than about 5% by weight and still more preferably a non-detectable, de minimus, or even 0% by weight of the compound crosses the blood-brain barrier at therapeutically relevant doses. Selected compounds can be evaluated for CNS penetration by determining plasma and brain levels following i.v., oral, subcutaneous or intraperitoneal administration.

The compounds described herein are typically administered in admixture with one or more pharmaceutically acceptable excipients or carriers in the form of a pharmaceutical composition. A 'composition' may contain one compound or a mixture of compounds. A 'pharmaceutical composition' is any composition useful or potentially useful in producing at least one physiological response in a subject to which such pharmaceutical composition is administered.

The pharmaceutical compositions of compounds of formula (I) may be administered enterally and/or parenterally. Parenteral administration includes subcutaneous, intramuscular, intradermal, intramammary, intravenous, and other administrative methods known in the art. Enteral administration includes solution, tablets, sustained release capsules, enteric coated capsules, syrups, beverages, foods, and other nutritional supplements. When administered, the present pharmaceutical compositions may be at or near body temperature. In some embodiments, the present pharmaceutical compositions may be below body temperatures. In other embodiments, the present pharmaceutical compositions may be above body temperatures.

The compounds of the present invention may be administered in a wide variety of different dosage forms. For example, they may be combined with various pharmaceutically acceptable inert carriers in the form of one or more of, but not limited to, tablets, capsules, lozenges, troches, hard candies, powders, sprays, creams, salves, suppositories, jellies, gels, pastes, lotions, ointments, aqueous suspensions, injectable solutions, elixirs, syrups, and the like. Such carriers may include one or more of solid diluents or fillers, sterile aqueous media, and various nontoxic organic solvents, etc. Moreover, oral pharmaceutical compositions may be sweetened and/or flavored. In general, the compounds of the invention may be present in such dosage forms at concentration levels ranging from about 0.1% to about 90% by weight.

For oral administration, tablets may contain various excipients such as one or more of microcrystalline cellulose, sodium citrate, calcium carbonate, dicalcium phosphate, and glycine, along with various disintegrants such as starch (such as corn, potato or tapioca starch), alginic acid and certain complex silicates, together with granulation binders like polyvinylpyrrolidone, sucrose, gelatin and acacia. Additionally, lubricating agents such as magnesium stearate, sodium lauryl sulfate and talc may be employed. Solid compositions of a similar type may also be employed as fillers in gelatin capsules; exemplary materials in this connection may also include lactose or milk sugar as well as high molecular weight polyethylene glycols. When aqueous suspensions and/or elixirs are desired for oral administration, the active ingredient may be combined with various sweetening or flavoring agents, coloring matter or dyes, and, if so desired, emulsifying and/or suspending agents, together with diluents such as water, ethanol, propylene glycol, glycerin, and various combinations thereof.

For parenteral administration (including intraperitoneal, subcutaneous, intravenous, intradermal or intramuscular injection), solutions of compounds of the present invention in, for example, either sesame or peanut oil or in aqueous propylene glycol may be employed. The aqueous solutions may be buffered, if necessary or desirable, and the liquid diluent first rendered isotonic. These aqueous solutions may be suitable for intravenous injection purposes. The oily solutions may be suitable for intraarticular, intramuscular, and/or subcutaneous injection purposes.

The preparation of such solutions under sterile conditions may be accomplished by standard pharmaceutical techniques known to those having ordinary skill in the art. For parenteral administration, examples of suitable preparations may include solutions, such as oily or aqueous or non-aqueous solutions, as well as suspensions, emulsions, and/or implants, including suppositories. Compounds of the present invention may be formulated in sterile form in multiple or single dose formats. For example, the compounds of the present invention may be dispersed in a fluid carrier such as sterile saline and/or 5% saline dextrose solutions commonly used with injectables.

In another embodiment, the compounds of the present invention may be administered topically. For example, it may be desirable to administer the compounds of the present invention topically when treating inflammatory conditions of the skin. Non-limiting examples of methods of topical administration include transdermal, buccal, or sublingual application. For topical applications, therapeutic compounds may be suitably admixed in a pharmacologically inert topical carrier such as a gel, an ointment, a lotion, and/or a cream. Such topical carriers may include water, glycerol, alcohol, propylene glycol, fatty alcohols, triglycerides, fatty acid esters, and/or mineral oils. Other possible topical carriers may include liquid petrolatum, isopropylpalmitate, polyethylene glycol, ethanol 95%, polyoxyethylene monolaurate 5% in water, sodium lauryl sulfate 5% in water, and the like, and combinations thereof. In addition, materials such as surfactants, anti-oxidants, humectants, viscosity stabilizers, and the like, and combinations thereof, also may be added if desired.

It will be appreciated by those having ordinary skill in the art that the exemplary amounts of active compounds used in a given therapy will vary according to the specific compound being utilized, the particular compositions formulated, the mode of application, the particular site of administration, etc. Optimal administration rates for a given protocol of administration may be ascertained by those having ordinary skill in the art using conventional dosage determination tests conducted with regard to the foregoing guidelines.

In general, compounds of the present invention for treatment may be administered to a subject in a suitable effective dose of one or more compounds of the present invention may be in the range of from about 0.01 to about 100 milligrams per kilogram of body weight of recipient per day, in some embodiments, in the range of from about 0.5 to about 50 milligrams per kilogram body weight of recipient per day, in still other embodiments, in the range of from about 0.1 to about 20 milligrams per kilogram body weight of recipient per day. The exemplary dose may be suitably administered once daily, or several sub-doses, e.g. 2 to 5 sub-doses, may be administered at appropriate intervals through the day, or on other appropriate schedules.

An embodiment of the present invention provides preparation of the novel compounds of formula (I) according to the procedures of the following examples, using appropriate materials. Those skilled in the art will understand that known variations of the conditions and processes of the following preparative procedures can be used to prepare these compounds. Moreover, by utilizing the procedures described in detail, one of ordinary skill in the art can prepare additional compounds of the present invention claimed herein. All temperatures are in degrees Celsius unless otherwise noted.

EXAMPLES

The following acronyms, abbreviations, terms and definitions have been used throughout the reaction schemes and experimental section.
Al$_2$O$_3$ (Aluminum oxide), BOP (Benzotriazole-1-yl-oxy-tris-(dimethylamino)-phosphonium hexafluorophosphate), DCC (N,N'-Dicyclohexylcarbodiimide), DIPEA [(N,N-diisopropylethylamine) (Hünig's base)], DMF (N,N-dimethylformamide), DMSO (dimethyl sulfoxide), DCM (Dichloromethane), DMAP (Dimethyl amino pyridine), Ether (diethyl ether), EDCl (1-ethyl-3-(3-dimethylaminopropyl) carbodiimide hydrochloride, HOBt (1-hydroxybenzotriazole), HCl (hydrochloric acid), HATU [0-(–7-azabenzotriazol-1-yl)-N,N,N',N'-tetramethyluronium hexafluorophosphate], KOH (Potassium hydroxide), LiAlH$_4$ (Lithium aluminum hydride), NaBH$_4$ (Sodium Borohydride), Na$_2$CO$_3$ (Sodium Carbonate), NaHCO$_3$ (Sodium bicarbonate), NaH (Sodium hydride), NaOH (Sodium Hydroxide), Na$_2$SO$_4$ (Sodium Sulfate), Pd/C (Palladium/Carbon), PyBOP (Benzotriazol-1-yl-oxytripyrrolidinophosphonium hexafluorophosphate), TBAB (Tetrabutyl ammonium bromide), THF (Tetrahydrofuran), h (hour), min (minute), TLC (thin layer chromatography), MS (mass spectroscopy), NMR (nuclear magnetic resonance), IR (Infrared Spectroscopy), Mp/mp (melting point), aq (aqueous).

$^1$H NMR abbreviations: MHz (Megahertz), br (broad), apt (apparent), s (singlet), d (doublet), t (triplet), q (quartet), dd (doublet of doublets), m (multiplet).

The following general schemes describe various embodiments of the present invention. Other embodiments within the scope of the claims herein will be apparent to one skilled in the art from consideration of the specification or practice of the invention as disclosed herein. It is intended that the specification, together with the examples, be considered to be exemplary only, with the scope and spirit of the invention being indicated by the claims which follow the examples. The compound of formula (I) can be synthesized by following the processes explained in following General Scheme A to C, wherein all symbols/variables are as defined earlier unless otherwise stated:

Scheme A for the preparation of the Amine intermediates

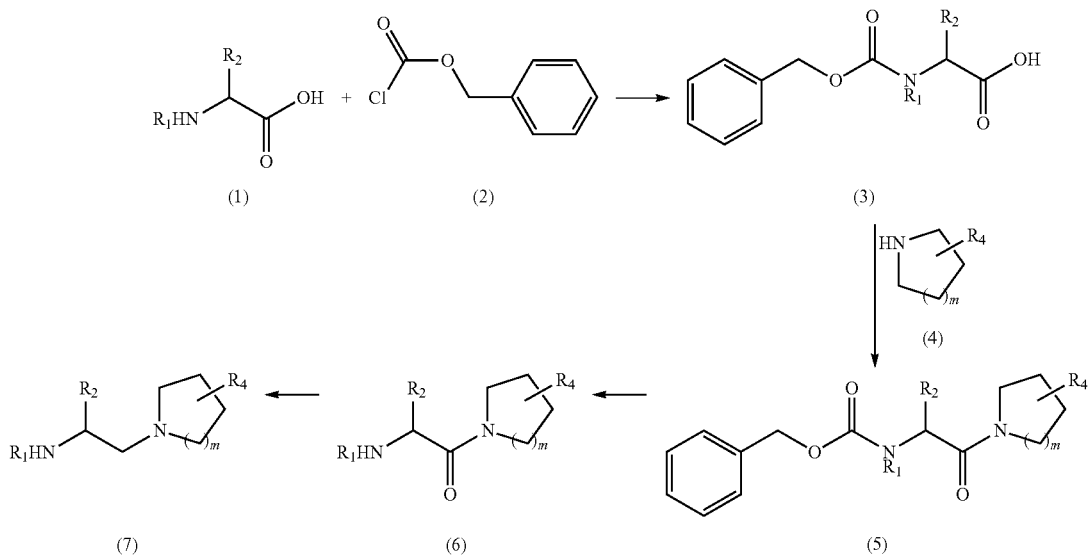

Step 1:
The protection of nitrogen in the compound of general formula (I), wherein R$_1$ and R$_2$ are as described in the compound of general formula (I) in the specification, can be effected by reacting with a protecting agent such as benzyl chloroformate (2) in presence of a mild base such as sodium bicarbonate under suitable conditions of solvent and temperature, to yield a compound of general formula (3).

Step 2:
Condensation of the compound (3) obtained in step (1) with a compound of general formula (4) which represents a nitrogen containing saturated heterocycle substituted with R$_4$ using suitable coupling agents such as EDCI/HOBt, HATU, BOP, PyBOP, DCC/HOBt, and the like in a suitable solvent like DCM, DMF and the like in the presence or absence of base like DMAP, DIPEA and the like can yield a compound of general formula (5). Values of R$_4$ are as defined in the general formula I.

Step 3:
Deprotection of the nitrogen, i.e., removal of the benzyloxy group can be effected under hydrogenolytic conditions by treating the compound of general formula (5) with hydrogen in presence of a suitable catalyst such as Pd/C under suitable conditions of solvent and temperature.

Step 4:
A compound of general formula (7) can be obtained by reduction of the compound of formula (5 or 6) using suitable reducing agents such as LiAlH$_4$, NaBH$_4$ and the like under suitable conditions of solvent and temperature.

Following are the Non-Limiting Examples of the Amine Intermediate of the Formula (7):

| Amine intermediate of formula (7) | Analytical data |
|---|---|
| (structure: (S)-N-methyl-1-phenyl-2-(pyrrolidin-1-yl)ethanamine) | $^1$H NMR (d$_6$-DMSO, 400 MHz): δ 7.36-7.28 (m, 4H), 7.24-7.22 (m, 1H), 3.55-3.51 (m, 1H), 2.66-2.61 (m, 1H). |
| (structure: (S)-1-phenyl-2-(pyrrolidin-1-yl)ethanamine) | $^1$H NMR (d$_6$-DMSO, 400 MHz): δ 7.46-7.35 (m, 2H), 7.30-7.24 (m, 2H), 7.21-7.18 (m, 1H), 3.98-3.37 (m, 1H), 2.58-2.45 (m, 3H), 2.42-2.40 (m, 2H), 2.29 (dd, J = 4.6 & 11.5 Hz, 1H), 2.31-2.27 (m, 1H), 2.00 (bs, 2H), 1.77-1.59 (m, 4H). <br> MS (ES): m/z 191.4 (M$^+$ + 1). |
| (structure with (S)-pyrrolidin-3-ol substituent) | $^1$H NMR (d$_6$-DMSO, 400 MHz): δ 7.37-7.30 (m, 2H), 7.29-7.24 (m, 2H), 7.23-7.19 (m, 1H), 4.19-4.14 (m, 1H), 3.96-3.92 (m, 1H), 3.32 (bs, 2H), 2.80-2.76 (m, 1H), 2.69-2.65 (m, 1H), 2.43-2.38 (m, 1H), 2.32-2.26 (m, 2H), 2.00-1.91 (m, 2H), 1.56-1.49 (m, 1H). |
| (isopropyl analog, HCl salt) | $^1$H NMR (d$_6$-DMSO, 400 MHz): δ 4.01-3.98 (m, 1H), 3.41-3.36 (m, 1H), 2.59-2.50 (m, 1H), 2.48-2.46 (m, 3H), 2.34-2.28 (m, 2H), 2.19-2.18 (m, 1H), 1.68-1.61 (m, 4H), 1.24 (bs, 2H), 0.85 (d, J = 67.9 Hz, 3H), 0.80 (d, J = 6.9 Hz, 3H).; <br> MS (ES): m/z 157.3 (M$^+$ + 1). |
| (azetidin-3-ol analog) | $^1$H NMR (d$_6$-DMSO, 400 MHz): δ 7.54-7.50 (m, 2H), 7.49-7.43 (m, 2H), 7.42-7.41 (m, 1H), 4.63-4.59 (m, 1H), 4.32-4.28 (m, 1H), 4.23-4.18 (m, 1H), 3.99-3.97 (m, 1H), 3.86-3.82 (m, 1H), 3.67 (t, J = 5.8 Hz, 1H), 2.75 (bs, 2H). <br> MS (ES): m/z 193 (M$^+$ + 1). |
| ((R)-pyrrolidin-3-ol analog) | MS(ES): m/z 207.1 (M$^+$ + 1). |
| (dimethylamino pyrrolidine analog) | $^1$H NMR (400 MHz, CDCl$_3$): δ 7.38-7.30 (m, 5H), 4.08-4.05 (m, 1H), 2.93-2.89 (m, 1H), 2.79-2.71 (m, 1H), 2.69-2.64 (m, 2H), 2.42-2.34 (m, 2H), 2.24 (s, 2H), 2.21 (s, 6H), 1.98-1.95 (m, 1H). <br> MS (ES): m/z 234.2 (M$^+$ + 1). |
| (methylamino pyrrolidine analog) | $^1$H NMR (400 MHz, CDCl$_3$) δ 7.39-7.30 (m, 5H), 4.09-4.06 (m, 1H), 3.18-3.17 (m, 1H), 2.80-2.71 (m, 3H), 2.45-2.40 (m, 4H), 2.39 (s, 3H), 2.12-2.10 (m, 1H), 1.61-1.59 (m, 1H). <br> MS (ES): m/z 220.3 (M$^+$ + 1). |

-continued

| Amine intermediate of formula (7) | Analytical data |
|---|---|
| 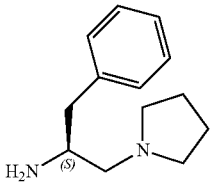 | ¹H NMR (d₆-DMSO, 400 MHz): δ 7.29-7.25 (m, 2H), 7.20-7.16 (m, 3H), 3.02-2.96 (m, 1H), 2.69-2.65 (m, 1H), 2.47-2.29 (m, 6H), 2.22-2.18 (m, 1H), 1.68-1.65 (m, 4H), 1.43 (bs, 2H). MS (ES): m/z 205.3 (M$^+$ + 1) |
| 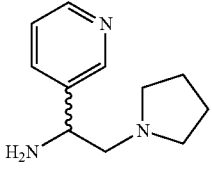 | ¹H NMR (d₆-DMSO, 400 MHz): δ 8.54-8.53 (m, 1H), 8.42-8.4 (m, 1H), 7.77 (d, J = 7.9 Hz, 1H), 7.30-7.29 (m, 1H), 4.01-3.97 (m, 1H), 2.59-2.35 (m, 6H), 1.66-1.43 (m, 4H). MS (ES): m/z 192.3 (M$^+$ + 1). |
| 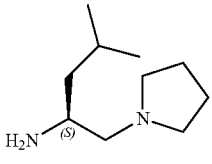 | ¹H NMR (400 MHz, CDCl₃ + d₆-DMSO): δ 3.46 (s, 2H), 2.95-2.90 (m, 1H), 2.59-2.56 (m, 2H), 2.22-2.18 (m, 1H), 1.87-1.77 (m, 4H), 1.76-1.70 (m, 4H), 1.19-1.15 (m, 2H), 0.92-0.89 (m, 6H). MS (ES): m/z 171 (M$^+$ + 1). |
| 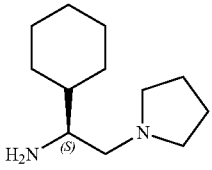 | ¹H NMR (400 MHz, CDCl₃ + d₆-DMSO): δ 3.32 (bs, 2H), 2.60-2.57 (m, 1H), 2.56-2.47 (m, 5H), 2.35-2.30 (m, 2H), 2.21-2.11 (m, 1H), 1.58-1.76 (m, 4H), 1.19-1.00 (m, 6H). MS (ES): m/z 197.3 (M$^+$ + 1). |
| 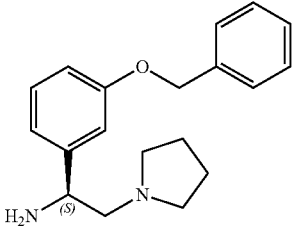 | ¹H NMR (d₆-DMSO, 400 MHz): δ 7.44-7.31 (m, 5H), 7.24-7.19 (m, 1H), 6.92-6.86 (m, 2H), 6.77 (d, J = 7.3 Hz, 1H), 5.08 (s, 2H), 4.62-4.58 (m, 1H), 2.38-2.29 (m, 2H), 1.65-1.59 (m, 4H), 1.34-1.24 (m, 4H). MS (ES): m/z 298.3 (M$^+$ + 1). |
| 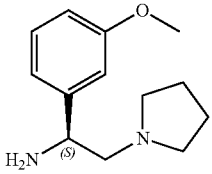 | ¹H NMR (d₆-DMSO, 400 MHz): δ 7.19 (t, J = 7.9 Hz, 1H), 6.96-6.91 (m, 2H), 6.77-6.75 (m, 1H), 3.95-3.92 (m, 1H), 3.73 (s, 3H), 2.45-2.40 (m, 2H), 2.33-2.36 (m, 2H), 1.93-1.81 (m, 2H). MS (ES): m/z 221.2 (M$^+$ + 1). |
| 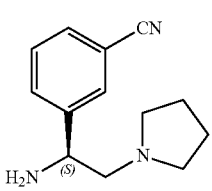 | ¹H NMR (d₆-DMSO, 400 MHz): δ 7.82-7.62 (m, 3H), 7.59-7.54 (m, 1H), 4.74 (t, J = 7.3 Hz, 1H), 2.50-2.49 (m, 4H), 2.33-2.18 (m, 2H), 1.83-1.56 (m, 4H). MS (ES): m/z 216.2 (M$^+$ + 1). |

-continued

| Amine intermediate of formula (7) | Analytical data |
|---|---|
| 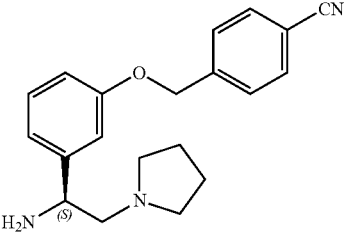 | ¹H NMR (d₆-DMSO, 400 MHz): δ 7.86 (d, J = 8.5 Hz, 2H), 7.65 (d, J = 7.9 Hz, 2H), 7.24-7.20 (m, 1H), 7.00 (s, 1H), 6.99-6.92 (m, 1H), 6.89-6.85 (m, 1H), 5.21 (s, 2H), 4.60-4.44 (m, 1H), 2.60-2.4 (m, 6H), 1.67-1.60 (m, 4H) |
| 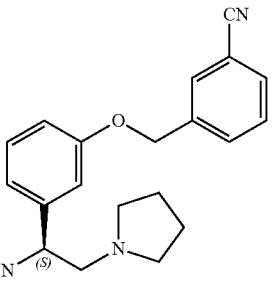 | ¹H NMR (d₆-DMSO, 400 MHz): δ 7.98-7.91 (m, 1H), 7.80 (d, J = 7.6 Hz, 2H), 7.64-7.59 (m, 1H), 7.28-7.19 (m, 1H), 7.02-7.00 (m, 1H), 6.94-6.92 (m, 1H), 6.89-6.86 (m, 1H), 5.16 (s, 2H), 4.59 (dd, J = 7.6 & 5.2 Hz, 1H), 3.55-3.42 (m, 2H), 3.34-3.18 (m, 2H), 2.61-2.42 (m, 4H), 1.86-1.61 (m, 4H) |
| 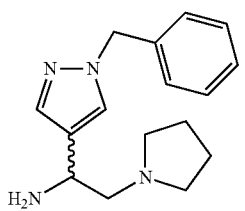 [SMILES: NC(CN1CCCC1)c1cnn(Cc2ccccc2)c1] | ¹H NMR (d₆-DMSO, 400 MHz): δ 7.64 (s, 1H), 7.39 (s, 1H), 7.32-7.27 (m, 3H), 7.21-7.20 (m, 2H), 5.24 (s, 2H), 3.91-3.87 (m, 1H), 2.40-2.38 (m, 4H), 1.89-1.80 (m, 2H), 1.67-1.62 (m, 4H). MS (ES): m/z 271 (M⁺ + 1). |
| 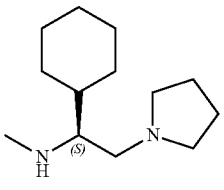 | MS(ES): m/z 227 (M⁺ + 1). |
| 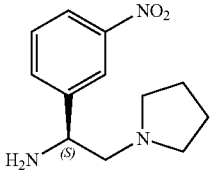 | ¹H NMR (d₆-DMSO, 400 MHz): δ 8.26 (s, 1H), 8.06 (dd, J₁ = 1.5 Hz, J₂ = 8.4 Hz, 1H), 7.81 (d, J = 7.9 Hz, 1H), 7.61-7.55 (m, 1H), 4.12-4.07 (m, 1H), 2.60 (d, J = 2.3 Hz, 2H), 2.56-2.36 (m, 6H), 1.65 (s, 4H). MS (ES): m/z 236 (M⁺ + 1). |
| 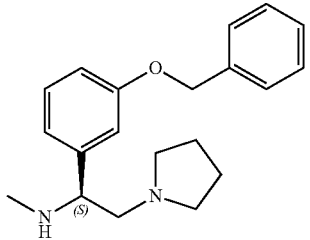 | ¹H NMR (d₆-DMSO, 400 MHz): δ 7.46-7.30 (m, 5H), 7.22 (t, J = 7.9 Hz, 1H), 7.0 (s, 1H), 6.87 (dd, J₁ = 2.6 Hz, J₂ = 8.0 Hz, 2H), 5.07 (s, 2H), 3.57-3.53 (m, 1H), 2.66 (t, J = 10.8 Hz, 1H), 2.57 (d, J = 5.2 Hz, 3H), 2.43-2.24 (m, 4H), 2.14 (s, 2H), 1.68 (s, 4H). MS (ES): m/z 311 (M⁺ + 1) |

| Amine intermediate of formula (7) | Analytical data |
|---|---|
| 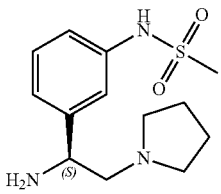 | MS(ES): m/z 284.9 (M⁺ + 1). |
| 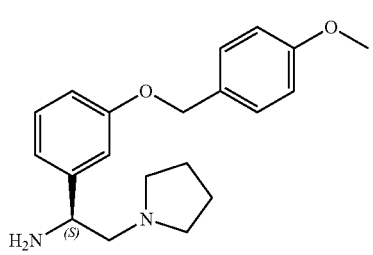 | ¹H NMR (d₆-DMSO, 400 MHz): δ 7.37 (d, J = 8.3 Hz, 2H), 7.18 (t, J = 7.9 Hz, 1H), 7.03 (s, 1H), 6.95-6.84 (m, 4H), 6.82 (d, J = 1.9 Hz, 1H), 4.98 (s, 2H), 3.95-3.92 (m, 1H), 3.75 (s, 3H), 3.31 (s, 2H), 2.66-2.50 (m, 2H), 2.41 (d, J = 6.7 Hz, 3H), 2.32-2.28 (m, 1H), 1.67 (s, 4H).<br>MS(ES): m/z 327.1 (M⁺ + 1). |
| 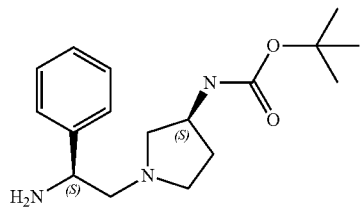 | MS(ES): m/z 306.5 (M⁺ + 1). |

Following two amines were also prepared by the similar procedure as set forth above:

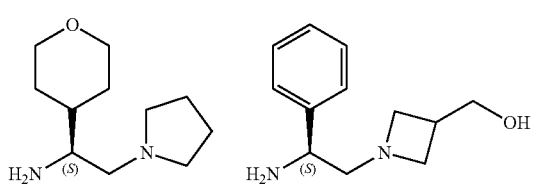

Scheme B for the preparation of the Acid Reactant

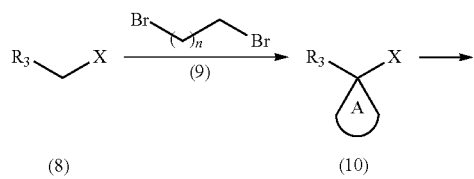

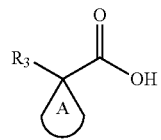

X = CN, CO2Me

Step 1:

A compound of formula (10) can be obtained by the reaction of a compound of general formula (8) wherein $R_3$ is the same as in compound of general formula (I) and a dibromoalkane of formula (9) wherein n has a value of 1-5, in the presence of a base such as NaH, KOH or NaOH with TBAB as a catalyst, and the like under suitable conditions of solvent and temperature.

Step 2:

Hydrolysis of compound of formula (10) to form the corresponding acid of formula (II) can be brought about under either acidic conditions like using sulfuric acid, hydrochloric acid or basic conditions like $K_2CO_3$, $Na_2CO_3$, KOH, NaOH, LiOH under suitable conditions of solvent and temperature.

Following are the Non-Limiting Examples of the Acid of the Formula (II):

| Acid Intermediate of formula (11) | Analytical Data |
|---|---|
| 1-phenylcyclobutanecarboxylic acid | $^1$H NMR (d$_6$-DMSO, 400 MHz): δ 12.20 (bs, 1H), 7.30-7.20 (m, 5H), 2.72-2.70 (m, 2H), 2.60-2.50 (m, 2H), 1.96-1.93 (m, 2H). |
| 1-phenylcyclopentanecarboxylic acid | $^1$H NMR (d$_6$-DMSO, 400 MHz): δ 12.22 (bs, 1H), 7.35-7.20 (m, 5H), 2.6-2.50 (m, 4H), 1.82-1.59 (m, 4H) <br> MS (ES): m/z 189.2 (M$^+$ + 1). |
| 1-phenylcyclopropanecarboxylic acid | $^1$H NMR (d$_6$-DMSO, 400 MHz): δ 12.26 (s, 1H), 7.33-7.20 (m, 5H), 1.46-1.40 (m, 2H), 1.15-1.11 (m, 2H) <br> MS (ES): m/z 161.4 (M$^+$ + 1). |
| 1-(quinolin-3-yl)cyclopropanecarboxylic acid | $^1$H NMR (d$_6$-DMSO, 400 MHz): δ 12.56 (bs, 1H), 8.89 (s, 1H), 8.24 (s, 1H), 8.0-7.9 (m, 2H), 7.75-7.71 (m, 1H), 7.62-7.58 (m, 1H), 1.58-1.55 (m, 2H), 1.34-1.32 (m, 2H). <br> MS (ES): m/z 214.3 (M$^+$ + 1). |
| 1-(pyridin-3-yl)cyclopropanecarboxylic acid | $^1$H NMR (400 MHz, d$_6$-DMSO- + CDCl$_3$): δ 12.35 (bs, 1H), 8.58 (s, 1H), 8.45-8.44 (m, 1H), 7.70-7.68 (m, 1H), 7.27-7.24 (m, 1H), 1.65-1.62 (m, 2H), 1.20-1.17 (m, 2H). <br> MS (ES): m/z 164.3 (M$^+$ + 1). |
| 1-phenylcyclopropanecarboxylic acid | $^1$H NMR (d$_6$-DMSO, 400 MHz): δ 12.26 (s, 1H), 7.33-7.20 (m, 5H), 1.46-1.40 (m, 2H), 1.15-1.11 (m, 2H) <br> MS (ES): m/z 161.4 (M$^+$ + 1). |
| 1-(quinolin-3-yl)cyclopropanecarboxylic acid | $^1$H NMR (d$_6$-DMSO, 400 MHz): δ .92 (bs, 1H), 8.26-8.25 (bs, 1H), 8.03-7.01 (m, 4H), 1.64-1.54 (m, 2H), 1.39-1.34 (m, 2H) <br> MS (ES): m/z 214.0 (M$^+$ + 1). |
| 1-(benzo[d]oxazol-2-yl)cyclopropanecarboxylic acid | $^1$H NMR (d$_6$-DMSO, 400 MHz): δ 7.69-7.34 (m, 4H), 2.09-2.02 (m, 2H), 1.97-1.87 (m, 2H) <br> MS (ES): m/z 204.1 (M$^+$ + 1). |

| Acid Intermediate of formula (11) | Analytical Data |
|---|---|
| (4-phenylthiazol-2-yl cyclopropane carboxylic acid) | $^1$H NMR (d$_6$-DMSO, 400 MHz): δ 13.1 (bs, 1H), 7.90-7.80 (m, 3H), 7.4-7.2 (m, 3H), 1.80-1.79 (m, 4H); MS (ES): m/z 246 (M$^+$ + 1). |
| (benzo[d][1,3]dioxol-5-yl cyclopropane carboxylic acid) | $^1$H NMR (d$_6$-DMSO, 400 MHz): δ 12.22 (bs, 1H), 6.87-6.75 (m, 3H), 5.97 (s, 2H), 1.40-1.37 (m, 2H), 1.09-1.07 (m, 2H) MS (ES): m/z 206.0 (M$^+$ + 1). |
| (benzo[d]thiazol-2-yl cyclopropane carboxylic acid) | $^1$H NMR (d$_6$-DMSO, 400 MHz): δ 13.20 (bs, 1H), 8.0-7.8 (m, 2H), 7.47-7.39 (m, 2H), 1.80 (s, 4H). MS (ES): m/z 220 (M$^+$ + 1). |
| (3-cyanophenyl cyclopropane carboxylic acid) | $^1$H NMR (d$_6$-DMSO, 400 MHz): δ 12.49 (bs, 1H), 7.79-7.47 (m, 4H), 1.49-1.43 (m, 2H), 1.28-1.12 (m, 2H) MS (ES): m/z 186.3 (M$^+$ + 1). |
| (quinolin-3-yl cyclopropane carboxylic acid) | $^1$H NMR (d$_6$-DMSO, 400 MHz): δ 8.92 (bs, 1H), 8.26-8.25 (bs, 1H), 8.03-7.01 (m, 4H), 1.64-1.54 (m, 2H), 1.39-1.34 (m, 2H) MS (ES): m/z 214.0 (M$^+$ + 1). |
| (3-methanesulfonamidophenyl cyclopropane carboxylic acid) | $^1$H NMR (d$_6$-DMSO, 400 MHz): δ 7.33-7.11 (m, 5H), 3.0 (s, 2H), 1.69-1.61 (m, 2H), 1.29-1.24 (m, 2H) MS (ES): m/z 278.3 (M$^+$ + Na). |
| (2-benzyl-2H-indazol-3-yl cyclopropane carboxylic acid) | $^1$H NMR (d$_6$-DMSO, 400 MHz): δ 12.42 (bs, 1H), 7.69-7.60 (m, 2H), 7.36-7.10 (m, 2H), 5.57 (s, 2H), 1.57-1.54 (m, 2H), 1.34-1.32 (m, 2H). MS (ES): m/z 293.4 (M$^+$ + 1). |
| (m-tolyl cyclopropane carboxylic acid) | $^1$H NMR (d$_6$-DMSO, 400 MHz): δ 12.23 (bs, 1H), 7.18-7.02 (m, 4H) 2.28 (s, 3H), 1.41 (s, 2H), 1.10 (s, 2H). MS (ES): m/z 177.4 (M$^+$ + 1). |

-continued

| Acid Intermediate of formula (11) | Analytical Data |
|---|---|
| 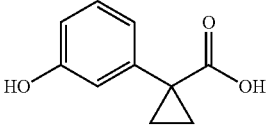 [SMILES: N#Cc1cccc(C2(C(=O)O)CC2)c1] | $^1$H NMR (d$_6$-DMSO, 400 MHz): δ 12.20 (bs, 1H), 9.33 (s, 1H), 7.11-7.04 (m, 1H), 6.72-6.70 (m, 2H), 6.69-6.60 (m, 1H), 1.40-1.37 (m, 2H), 1.08-1.05 (m, 2H). MS (ES): m/z 177 (M$^+$ + 1). |
| 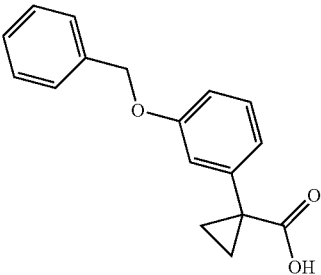 [SMILES: O=C(O)C1(c2cccc(OCc3ccccc3)c2)CC1] | $^1$H NMR (d$_6$-DMSO, 400 MHz): δ 12.27 (bs, 1H), 7.46-7.31 (m, 6H), 7.20 (t, J = 7.9 Hz, 1H), 6.95-6.87 (m, 3H), 5.07 (s, 2H), 1.42 (d, J = 2.6 Hz, 2H), 1.12 (d, J = 2.2 Hz, 2H). |
| 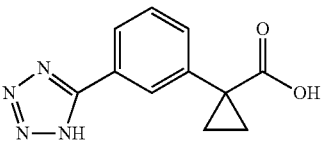 [SMILES: O=C(O)C1(c2cccc(-c3nnn[nH]3)c2)CC1] | $^1$H NMR (d$_6$-DMSO, 400 MHz): δ 8.34-7.60 (m, 4H), 1.57-1.52 (m, 2H), 1.32-1.24 (m, 2H) MS (ES): m/z 231.3 (M$^+$ + 1). |
| 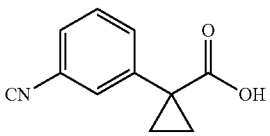 | $^1$H NMR (d$_6$-DMSO, 400 MHz): δ 12.49 (bs, 1H), 7.79-7.47 (m, 4H), 1.49-1.43 (m, 2H), 1.28-1.12 (m, 2H) MS (ES): m/z 186.3 (M$^+$ + 1). |
| 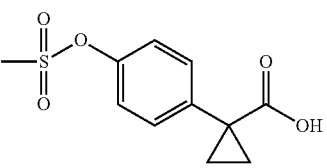 [SMILES: CS(=O)(=O)Oc1ccc(C2(C(=O)O)CC2)cc1] | $^1$H NMR (d$_6$-DMSO, 400 MHz): δ 12.39 (bs, 1H), 7.44-7.41 (m, 2H), 7.27-7.25 (m, 2H), 3.37 (s, 3H), 1.47-1.45 (m, 2H), 1.17-1.14 (m, 2H). MS (ES): m/z 255.2 (M$^+$ + Na). |
| 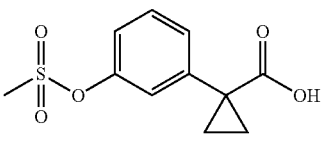 | $^1$H NMR (d$_6$-DMSO, 400 MHz): δ 12.41 (bs, 1H), 7.43-7.41 (m, 1H), 7.39-7.36 (m, 1H), 7.34-7.30 (m, 1H), 7.24-7.21 (m, 1H), 3.36 (s, 3H), 1.49-1.46 (m, 2H), 1.21-1.18 (m, 2H). MS (ES): m/z 278 (M$^+$ + Na). |
| 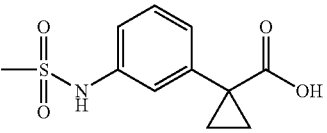 [SMILES: CS(=O)(=O)Nc1cccc(C2(C(=O)O)CC2)c1] | $^1$H NMR (d$_6$-DMSO, 400 MHz): δ 7.33-7.11 (m, 5H), 3.00 (s, 2H), 1.69-1.61 (m, 2H), 1.29-1.24 (m, 2H) MS (ES): m/z 278.3 (M$^+$ + Na). |
| 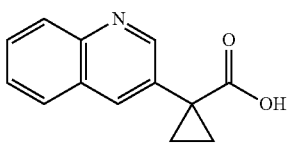 [SMILES: O=C(O)C1(c2cnc3ccccc3c2)CC1] | $^1$H NMR (d$_6$-DMSO, 400 MHz): 8.92 (bs, 1H), 8.26-8.25 (bs, 1H), 8.03-7.01 (m, 4H), 1.64-1.54 (m, 2H), 1.39-1.34 (m, 2H) MS (ES): m/z 214.0 (M$^+$ + 1). |
| 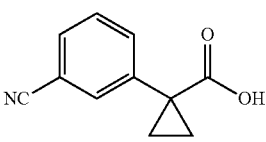 | $^1$H NMR (d$_6$-DMSO, 400 MHz): δ 12.49 (bs, 1H), 7.79-7.47 (m, 4H), 1.49-1.43 (m, 2H), 1.28-1.12 (m, 2H) MS (ES): m/z 186.3 (M$^+$ + 1). |

| Acid Intermediate of formula (11) | Analytical Data |
|---|---|
| 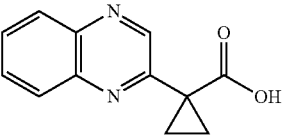 [SMILES: O=C(O)C1(c2cnc3ccccc3n2)CC1] | $^1$H NMR (d$_6$-DMSO, 400 MHz): δ 12.95 (bs, 1H), 9.12 (s, 1H), 8.09-8.06 (m, 1H), 8.03-8.00 (m, 1H), 7.84-7.80 (m, 2H), 1.60 (s, 4H). MS (ES): m/z 215.3 (M$^+$ + 1). |
| 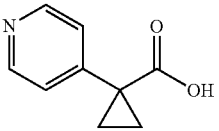 [SMILES: O=C(O)C1(c2ccncc2)CC1] | $^1$H NMR (d$_6$-DMSO, 400 MHz): δ 7.34-7.33 (m, 2H), 1.53-1.43 (m, 4H), 1.39-1.11 (m, 2H). MS (ES): m/z 164.4 (M$^+$ + 1). |
| 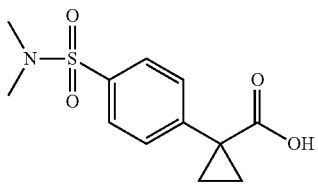 [SMILES: CN(C)S(=O)(=O)c1ccc(C2(C(=O)O)CC2)cc1] | $^1$H NMR (d$_6$-DMSO, 400 MHz): δ 7.68-7.57 (m, 4H), 2.61 (s, 6H), 1.55-1.48 (m, 2H), 1.25-1.19 (m, 2H). MS (ES): m/z 270.3 (M$^+$ + 1). |
| 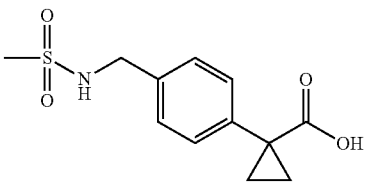 [SMILES: CS(=O)(=O)NCc1ccc(C2(C(=O)O)CC2)cc1] | $^1$H NMR (400 MHz, DMSO-d$_6$): δ 12.27(bs, 1H), 7.53-7.50 (m, 1H), 7.36-7.24 (m, 4H), 4.12 (s, 2H), 2.86 (s, 3H), 1.45-1.42 (m, 2H), 1.14-1.09 (m, 2H) MS (ES): m/z 287.4 (M$^+$ + NH$_4$) |
| 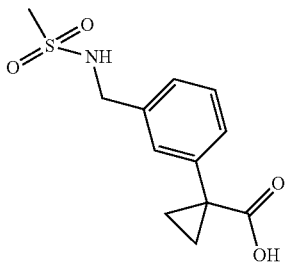 | $^1$H NMR (d$_6$-DMSO, 400 MHz): δ 12.29 (bs, 1H) 7.54-7.19 (m, 5H), 4.14 (s, 2H), 2.82 (s, 3H), 1.46-1.43 (m, 2H), 1.19-1.10 (m, 2H). MS (ES): m/z 177.4 (M$^+$ + 1). |
| 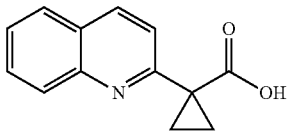 [SMILES: O=C(O)C1(c2ccc3ccccc3n2)CC1] | $^1$H NMR (d$_6$-DMSO, 400 MHz): δ 12.56 (bs, 1H), 8.89 (s, 1H), 8.24 (s, 1H), 8.01-7.93 (m, 2H), 7.75-7.58 (m, 2H), 1.57 (s, 2H), 1.33 (s, 2H). MS (ES): m/z 214.3 (M$^+$ + 1). |
| 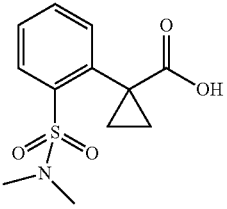 [SMILES: CN(C)S(=O)(=O)c1ccccc1C1(C(=O)O)CC1] | $^1$H NMR (d$_6$-DMSO, 400 MHz): δ 12.08 (bs, 1H), 7.75-7.73 (m, 1H), 7.62-7.47 (m, 3H), 2.76 (s, 6H), 1.70 (bs, 1H), 1.35 (bs, 3H). MS (ES): m/z 270.2 (M$^+$ + 1). |
| 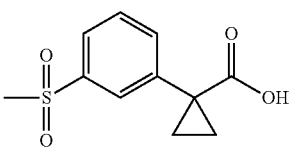 [SMILES: CS(=O)(=O)c1cccc(C2(C(=O)O)CC2)c1] | $^1$H NMR (d$_6$-DMSO, 400 MHz): δ 12.54 (bs, 1H), 7.86-7.84 (m, 2H), 7.61 (m, 2H), 3.20 (s, 2H), 1.52-1.49 (m, 2H), 1.22-1.19 (m, 2H). MS (ES): m/z 258.4 (M$^+$ + NH$_3$) |

-continued

| Acid Intermediate of formula (11) | Analytical Data |
|---|---|
| (1,1-dioxo-2,3-dihydro-1,2-benzothiazol-5-yl)cyclopropane-1-carboxylic acid | $^1$H NMR (d$_6$-DMSO, 400 MHz): δ 11.58 (bs, 1H), 11.47 (bs, 1H), 7.19 (s, 1H), 7.15 (d, J = 8.06 Hz, 1H), 6.69 (d, J = 8.43 Hz, 1H), 4.41 (s, 2H), 1.41-1.40 (m, 2H), 1.07-1.06 (m, 2H). MS (ES): m/z 252 (M$^+$ + 1). |
| 1-(2-oxo-1,2-dihydroquinolin-6-yl)cyclopropane-1-carboxylic acid | $^1$H NMR (d$_6$-DMSO, 400 MHz): δ 12.32 (bs, 1H), 11.70 (bs, 1H), 7.86 (d, J = 9.5 Hz, 1H), 7.58 (s, 1H), 7.46 (d, J = 8.4 Hz, 1H), 7.22 (d, J = 8.4 Hz, 1H), 6.47 (d, J = 9.5 Hz, 1H), 1.46 (d, J = 2.2 Hz, 2H), 1.23-1.01 (m, 2H). MS (ES): m/z 230.3 (M$^+$ + 1). |
| 1-(4-chlorophenyl)cyclopropane-1-carboxylic acid | $^1$H NMR (d$_6$-DMSO, 400 MHz): δ 12.37 (bs, 1H), 7.34 (s, 4H), 1.46-1.40 (m, 2H), 1.23-1.11 (m, 2H) MS (ES): m/z 195.2 (M$^+$ + 1). |
| 1-(2,2-dioxo-1,3-dihydro-2,1,3-benzoxathiazol-6-yl)cyclopropane-1-carboxylic acid | $^1$H NMR (d$_6$-DMSO, 400 MHz): δ 12.20-11.60 (bs, 2H), 7.19 (d, J = 8.8 Hz, 1H), 6.99-6.97 (m, 2H), 1.45-1.42 (m, 2H), 1.19-1.13 (m, 2H). MS (ES): m/z 254.2 (M$^+$ + 1). |
| 1-[3-(methanesulfonamido)phenyl]cyclopropane-1-carboxylic acid | $^1$H NMR (d$_6$-DMSO, 400 MHz): δ 7.33-7.11 (m, 5H), 3.0 (s, 2H), 1.69-1.61 (m, 2H), 1.29-1.24 (m, 2H). MS (ES): m/z 278.3 (M$^+$ + Na). |
| 1-[3-(dimethylsulfamoyl)phenyl]cyclopropane-1-carboxylic acid | $^1$H NMR (d$_6$-DMSO, 400 MHz): δ 7.65 (s, 1H), 7.64 (d, J = 1.5 Hz, 2H), 7.62-7.55 (m, 1H), 2.58 (s, 6H), 1.52-1.49 (m, 2H), 1.22-1.19 (m, 2H) MS (ES): m/z 270.0 (M$^+$ + 1). |

| Acid Intermediate of formula (11) | Analytical Data |
|---|---|
| 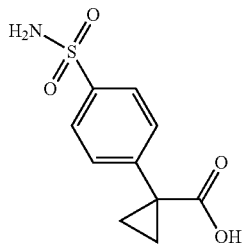 [SMILES: NS(=O)(=O)c1ccc(C2(C(=O)O)CC2)cc1] | $^1$H NMR (d$_6$-DMSO, 400 MHz): δ 7.73 (d, J = 4.5 Hz, 2H), 7.49 (d, J = 1.8 Hz, 2H), 7.31 (bs, 2H), 1.47-1.45 (m, 2H), 1.16-1.13 (m, 2H) MS (ES): m/z 240.0 (M$^+$ + 1). |
| 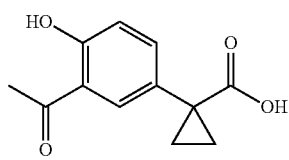 [SMILES: CC(=O)c1cc(C2(C(=O)O)CC2)ccc1O] | $^1$H NMR (d$_6$-DMSO, 400 MHz): δ 12.29 (b, 1H), 11.90 (bs, 1H), 7.51-7.48 (m, 1H), 6.90-6.88 (m, 1H), 2.6 (s, 3H), 1.45 (s, 2H), 1.16 (s, 2H). MS (ES): m/z 221 (M$^+$ + 1). |
| 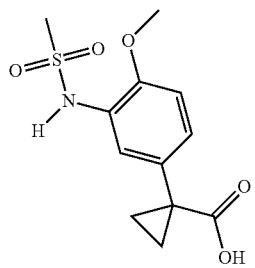 [SMILES: COc1ccc(C2(C(=O)O)CC2)cc1NS(C)(=O)=O] | $^1$H NMR (d$_6$-DMSO, 400 MHz): δ 12.24 (bs, 1H), 8.83 (bs, 1H), 7.31-7.01 (m, 3H), 3.80 (s, 3H), 2.93 (s, 3H), 1.43-1.40 (m, 2H), 1.19-1.10 (m, 2H). MS (ES): m/z 284.1. (M$^+$ + 1). |
| 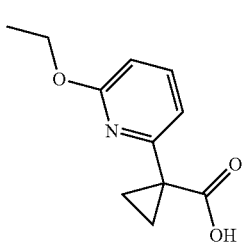 | $^1$H NMR (d$_6$-DMSO, 400 MHz): δ 12.56 (bs, 1H), 7.64 (t, J = 7.8 Hz, 1H), 7.12 (d, J = 7.3 Hz, 1H), 6.63 (d, J = 7.9 Hz, 1H), 4.25 (q, J = 7.0 Hz, 2H), 1.48-1.42 (m, 3H), 1.37-1.33 (m, 2H), 1.28-1.15 (m, 2H). MS (ES): m/z 206.1 (M$^+$ + 1). |
| 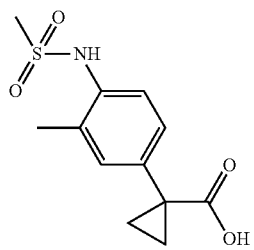 [SMILES: Cc1cc(C2(C(=O)O)CC2)ccc1NS(C)(=O)=O] | $^1$H NMR (d$_6$-DMSO, 400 MHz): δ 12.28 (bs, 1H), 8.99 (bs, 1H), 7.19-7.12 (m, 3H), 2.96 (s, 3H), 2.27 (s, 3H), 1.43-1.40 (m, 2H), 1.12-1.09 (m, 2H) MS (ES): m/z 287.3. (M$^+$ + NH$_4$). |
| 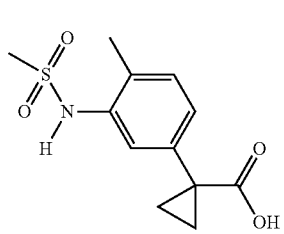 [SMILES: Cc1ccc(C2(C(=O)O)CC2)cc1NS(C)(=O)=O] | $^1$H NMR (d$_6$-DMSO, 400 MHz): δ 12.30 (bs, 1H), 8.99 (bs, 1H), 7.20-7.09 (m, 3H), 2.95 (s, 3H), 2.27 (s, 3H), 1.44-1.42 (m, 2H), 1.15-1.10 (m, 2H) MS (ES): m/z 268. (M$^+$ + 1). |

-continued

| Acid Intermediate of formula (11) | Analytical Data |
|---|---|
| 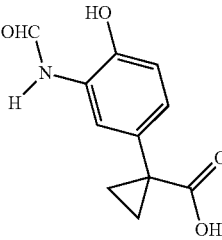 | $^1$H NMR (d$_6$-DMSO, 400 MHz): δ 12.14 (bs, 1H), 9.88 (bs, 1H), 9.53 (s, 1H), 8.26 (s, 1H), 8.03 (s, 1H), 6.87-6.84 (m, 1H) 6.80-6.75 (m, 1H) 1.42-1.38 (m, 2H), 1.08-1.02 (m, 2H). MS (ES): m/z 222 (M$^+$ + 1). |
| 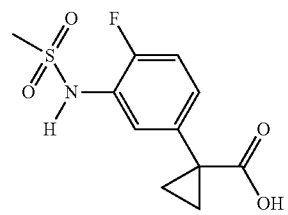 [SMILES: CS(=O)(=O)Nc1cc(C2(C(=O)O)CC2)ccc1F] | $^1$H NMR (d$_6$-DMSO, 400 MHz): δ 12.37 (bs, 1H), 9.54 (bs, 1H), 7.32-7.30 (d, j = 8.0 Hz, 1H), 7.20-7.18 (m, 2H), 3.01 (s, 3H), 1.46-1.43 (m, 2H), 1.14-1.11 (m, 2H) MS (ES): m/z 271.9 (M$^+$ + 1). |
| 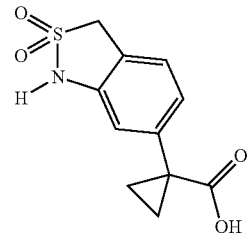 [SMILES: O=C(O)C1(c2ccc3c(c2)NS(=O)(=O)C3)CC1] | $^1$H NMR (d$_6$-DMSO, 400 MHz): δ 11.50 (bs, 1H), 11.40 (bs, 1H), 7.18 (d, J = 7.94 Hz, 1H), 6.91(d, J = 7.63 Hz, 1H), 6.75 (s, 1H), 4.47 (s, 2H), 1.43-1.42 (m, 2H), 1.11-1.10 (m, 2H). MS (ES): m/z 252 (M$^+$ + 1). |
| 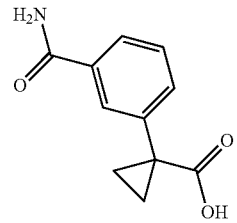 | $^1$H NMR (d$_6$-DMSO, 400 MHz): δ 7.97 (s, 1H), 7.82 (s, 1H), 7.74 (d, J = 7.6 Hz, 1H), 7.47 (d, J = 7.6 Hz, 1H), 7.34 (d, J = 7.0 Hz, 2H), 1.48-1.42 (m, 2H), 1.19-1.01 (m, 2H). |
| 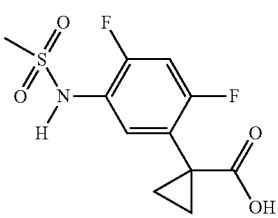 [SMILES: CS(=O)(=O)Nc1cc(C2(C(=O)O)CC2)c(F)cc1F] | $^1$H NMR (d$_6$-DMSO, 400 MHz): δ 12.50 (bs, 1H), 9.50 (s, 1H), 7.34-7.26 (m, 2H), 3.0 (s, 3H), 1.50-1.47 (m, 2H), 1.17-1.14 (m, 2H). MS (ES): m/z 314 (M$^+$ + Na). |
| 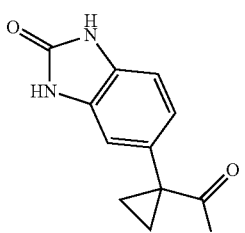 | $^1$H NMR (d$_6$-DMSO, 400 MHz): δ 12.17 (s, 1H), 10.52 (s, 2H), 6.88-6.80 (m, 3H), 1.40 (s, 2H), 1.09 (s, 2H). MS (ES): m/z 219.5 (M$^+$ + 1). |
| 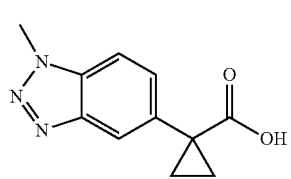 [SMILES: Cn1nnc2cc(C3(C(=O)O)CC3)ccc21] | $^1$H NMR (d$_6$-DMSO, 400 MHz): δ 12.35 (bs, 1H), 7.90 (s, 1H), 7.75 (d, J = 8.4 Hz, 1H), 7.55 (d, J = 7.3 Hz, 1H), 4.28 (s, 3H), 1.50-1.42 (m, 2H), 1.26-1.20 (m, 2H). MS (ES): m/z 218.2 (M$^+$ + 1). |

-continued

| Acid Intermediate of formula (11) | Analytical Data |
|---|---|
| 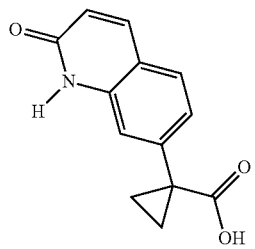 [SMILES: O=C(O)C1(c2ccc3ccc(=O)[nH]c3c2)CC1] | $^1$H NMR (d$_6$-DMSO, 400 MHz): δ 12.14 (bs, 2H), 8.19 (s, 1H), 7.51 (d, J = 7.7 Hz, 1H), 7.25 (s, 1H), 7.13 (d, J = 8.0 Hz, 1H), 6.44 (d, J = 9.5 Hz, 1H), 1.52-1.43 (m, 2H), 1.24-1.10 (m, 2H).<br>MS (ES): m/z 230.2 (M$^+$ + 1). |
| 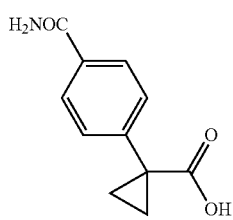 [SMILES: NC(=O)c1ccc(C2(C(=O)O)CC2)cc1] | $^1$H NMR (d$_6$-DMSO, 400 MHz): δ 11.2 (bs, 1H), 8.03 (d, J = 8.06 Hz, 1H), 7.90 (s, 1H), 7.8 (d, J = 8.4 Hz, 1H), 7.2 (d, J = 8.4 Hz, 2H), 7.3 (d, J = 8.42 Hz, 1H), 1.5-1.4 (m, 2H), 1.20-1.10 (m, 2H).<br>MS (ES): m/z 206.0 (M$^+$ + 1). |
| 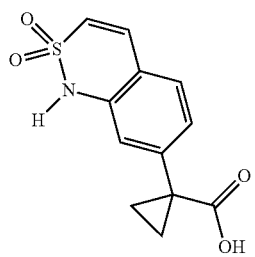 [SMILES: O=C(O)C1(c2ccc3c(c2)NS(=O)(=O)C=C3)CC1] | $^1$H NMR (d$_6$-DMSO, 400 MHz): δ 12.41 (bs, 1H), 11.49 (bs, 1H), 7.48-7.45 (m, 2H), 7.09-7.07 (m, 2H), 7.0 (d, J = 1.46 Hz, 1H), 1.48-1.45 (m, 2H), 1.17-1.14 (m, 2H).<br>MS (ES): m/z 264 (M$^+$ + 1). |
| 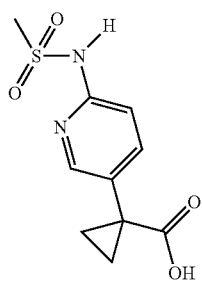 [SMILES: CS(=O)(=O)Nc1ccc(C2(C(=O)O)CC2)cn1] | $^1$H NMR (d$_6$-DMSO, 400 MHz): δ 11.71 (bs, 1H), 8.16 (s, 1H), 7.69 (m, 1H), 6.94-6.91 (m, 1H), 3.52 (s, 3H), 1.44 (s, 2H), 1.15 (s, 2H).<br>MS (ES): m/z 257.1 (M$^+$ + 1). |
| 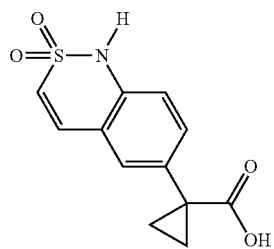 [SMILES: O=C(O)C1(c2ccc3c(c2)C=CS(=O)(=O)N3)CC1] | $^1$H NMR (d$_6$-DMSO, 400 MHz): δ 12.27 (bs, 1H), 11.55 (bs, 1H), 7.43 (s, 1H), 7.38-7.30 (m, 2H), 6.96-6.91 (m, 2H), 1.43 (s, 2H), 1.12 (s, 2H).<br>MS (ES): m/z 264 (M$^+$ + 1). |
| 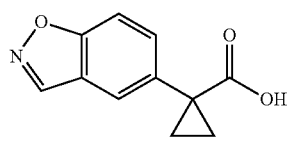 [SMILES: O=C(O)C1(c2ccc3oncc3c2)CC1] | $^1$H NMR (d$_6$-DMSO, 400 MHz): δ 12.34 (bs, 1H), 10.99 (bs, 1H), 7.51-7.50 (m, 1H), 7.46-7.44 (m, 1H), 6.93 (d, J = 8.4 Hz, 1H), 1.42-1.39 (m, 2H), 1.12-1.10 (m, 2H).<br>MS (ES): m/z 203.0 (M$^+$ + 1). |

-continued

| Acid Intermediate of formula (11) | Analytical Data |
|---|---|
| (2-oxo-2,3-dihydro-1H-benzo[d]oxazol-5-yl)cyclopropanecarboxylic acid structure | $^1$H NMR (d$_6$-DMSO, 400 MHz): δ 12.30 (bs, 1H), 11.6 (bs, 1H), 7.18-7.16 (m, 2H), 7.03-7.01 (m, 2H), 1.44 (s, 2H), 1.13 (s, 2H). MS (ES): m/z 218.0 (M$^+$ + 1). |
| (3-methyl-1H-indazol-5-yl)cyclopropanecarboxylic acid structure | $^1$H NMR (d$_6$-DMSO, 400 MHz): δ 12.38 (bs, 2H), 7.57 (s, 1H), 7.36-7.28 (m, 2H), 2.50 (s, 3H), 1.48 (s, 2H), 1.18 (s, 2H). MS (ES): m/z 217 (M$^+$ + 1). |
| (3-methyl-2-oxo-2,3-dihydro-1,3-benzoxazol-5-yl)cyclopropanecarboxylic acid structure | $^1$H NMR (d$_6$-DMSO, 400 MHz): δ 12.32 (s, 1H), 7.25-7.22 (m, 2H), 7.10-7.07 (m, 1H), 3.34 (s, 3H), 1.49-1.46 (m, 2H), 1.19-1.16 (m, 2H). MS (ES): m/z 234 (M$^+$ + 1). |
| 1-(4-cyanophenyl)cyclopropanecarboxylic acid structure | $^1$H NMR (d$_6$-DMSO, 400 MHz): δ 12.51 (bs, 1H), 7.76 (d, J = 4.7 Hz, 2H), 7.53 (d, J = 4.7 Hz, 2H), 1.51-1.44 (m, 2H), 1.26-1.19 (m, 2H) |
| 1-(4-methylsulfonylphenyl)cyclopropanecarboxylic acid structure | $^1$H NMR (d$_6$-DMSO, 400 MHz): δ 12.54 (bs, 1H), 7.86-7.84 (m, 2H), 7.61 (m, 2H), 3.20 (s, 2H), 1.52-1.49 (m, 2H), 1.22-1.19 (m, 2H). MS (ES): m/z 258.4 (M$^+$ + NH$_3$) |
| 1-(1H-benzimidazol-5-yl)cyclopropanecarboxylic acid structure | $^1$H NMR (d$_6$-DMSO, 400 MHz): δ 12.34 (bs, 1H), 12.18 (bs, 1H), 8.17 (s, 1H), 7.53 (s, 1H), 7.43 (s, 1H), 7.16 (s, 1H), 1.48-1.46 (bs, 2H), 1.18-1.16 (bs, 2H). MS (ES): m/z 203 (M$^+$ + 1). |
| 1-(2-oxoindolin-6-yl)cyclopropanecarboxylic acid structure | $^1$H NMR (d$_6$-DMSO, 400 MHz): δ 12.25 (bs, 1H), 10.32 (bs, 1H), 7.09 (d, J = 7.4 Hz, 1H), 6.86 (d, J = 7.7 Hz, 1H), 6.75 (s, 1H), 3.42 (s, 2H) 1.43-1.37 (bs, 2H), 1.10-1.08 (bs, 2H). MS (ES): m/z 218 (M$^+$ + 1). |
| 1-(4-hydroxyphenyl)cyclopropanecarboxylic acid structure | $^1$H NMR (d$_6$-DMSO, 400 MHz): δ 12.11 (bs, 1H), 9.27 (s, 1H), 7.10 (d, J = 8.8 Hz, 2H), 6.67 (d, J = 8.5 Hz, 2H), 1.38-1.36 (m, 2H), 1.04-1.01 (m, 2H). MS (ES): m/z 177 (M$^+$ + 1). |

-continued

| Acid Intermediate of formula (11) | Analytical Data |
|---|---|
| 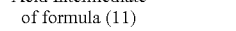 | $^1$H NMR (d$_6$-DMSO, 400 MHz): δ 12.20 (bs, 1H), 9.33 (s, 1H), 7.22-7.18 (m, 1H), 6.88 (d, J = 7.7 Hz, 1H), 6.85-6.79 (m, 2H), 3.73 (s, 3H), 1.43-1.40 (m, 2H), 1.13-1.11 (m, 2H). MS (ES): m/z 193 (M$^+$ + 1). |

Following acids were also prepared using similar procedures as set forth above:

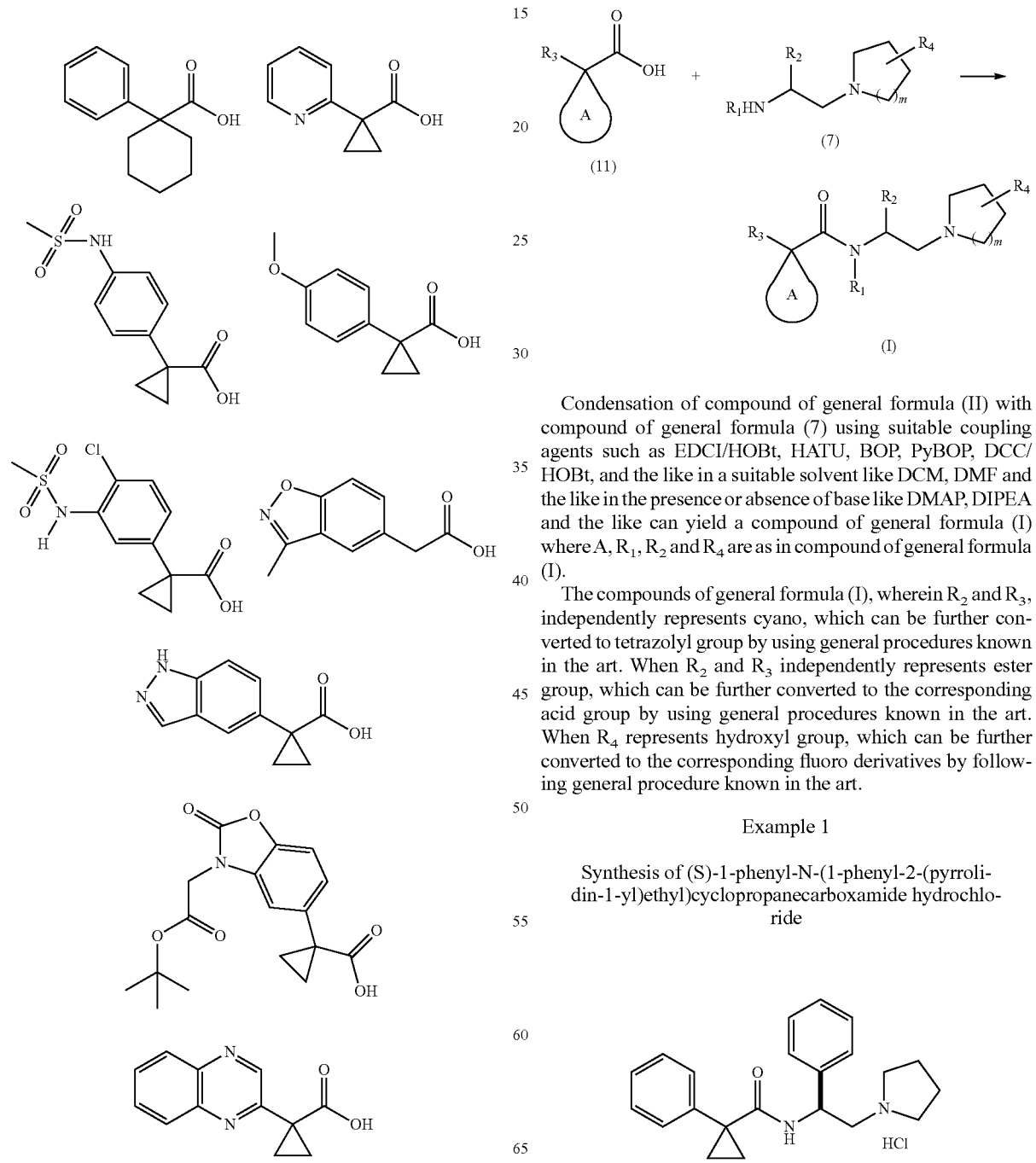

Condensation of compound of general formula (II) with compound of general formula (7) using suitable coupling agents such as EDCI/HOBt, HATU, BOP, PyBOP, DCC/HOBt, and the like in a suitable solvent like DCM, DMF and the like in the presence or absence of base like DMAP, DIPEA and the like can yield a compound of general formula (I) where A, $R_1$, $R_2$ and $R_4$ are as in compound of general formula (I).

The compounds of general formula (I), wherein $R_2$ and $R_3$, independently represents cyano, which can be further converted to tetrazolyl group by using general procedures known in the art. When $R_2$ and $R_3$ independently represents ester group, which can be further converted to the corresponding acid group by using general procedures known in the art. When $R_4$ represents hydroxyl group, which can be further converted to the corresponding fluoro derivatives by following general procedure known in the art.

Example 1

Synthesis of (S)-1-phenyl-N-(1-phenyl-2-(pyrrolidin-1-yl)ethyl)cyclopropanecarboxamide hydrochloride

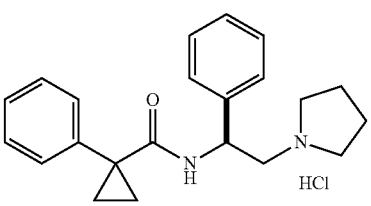 [SMILES: O=C(N[C@H](CN1CCCC1)c1ccccc1)C1(c2ccccc2)CC1 ; Cl]

Step (i)

Synthesis of (S)-2-(benzyloxycarbonylamino)-2-phenylacetic acid

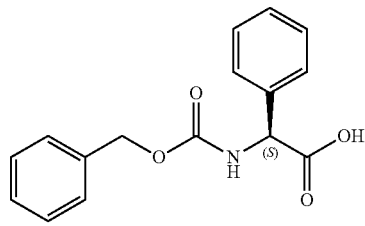

Experimental Procedure:

To a solution of L-phenyl glycine (50 g, 0.33 mol), in aqueous NaHCO$_3$ solution (66 g, 0.8 mol, 330 mL) was added benzyl chloroformate (101 g, 0.6 mol), and the reaction mixture was allowed to stir for 2 h at about 20-35° C. Then another portion of aqueous NaHCO$_3$ solution (33 g, 0.4 mol, 170 mL), benzyl chloroformate (101 g, 0.6 mol) was added to the reaction mixture and the mixture was allowed to stir at about 20-35° C. for 16 h. The reaction mixture was filtered and the filtrate was washed with diethyl ether (250 mL). The aqueous layer was acidified with 6N HCl to pH ~4.0 and the obtained solid (benzyloxymethyl-amino)-phenyl-acetic acid was filtered and dried (45 g, 47%).

$^1$H NMR (400 MHz, DMSO-d$_6$): δ 12.8 (bs, 1H), 8.03 (d, J=8.06 Hz, 1H), 7.46-7.23 (m, 10H), 5.13 (d, J=4.7 Hz, 1H), 5.05 (s, 2H); IR (KBr, cm$^{-1}$): 3400, 3034, 1734, 1672, 1531, 1247; MS (ES) m/z 286.6 (M$^+$+1)

Step (ii)

Synthesis of benzyl (S)-2-((S)-3-hydroxypyrrolidin-1-yl)-2-oxo-1-phenylethylcarbamate

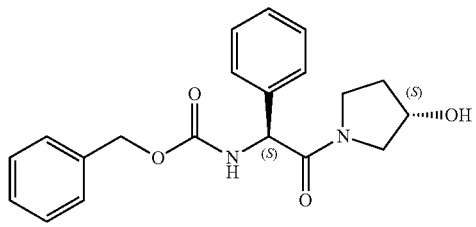

Experimental Procedure:

To a solution of (S)-2-(benzyloxycarbonylamino)-2-phenylacetic acid (8.2 g, 28.7 mmoles) in dichloromethane were added at about 20-35° C., dicyclohexane-carbodiimide (6 g, 28.7 mmoles) in DCM (50 mL) and 1-hydroxy benzo triazole (3.9 g, 28.7 mmoles) and the mixture was stirred at about 20-35° C. for 10 min. To this mixture was added S— pyrrolidinol (2.5 g, 28.7 mmoles) and the contents were allowed to stir for 12 h at about 20-35° C. The reaction mixture was filtered and the filtrate was diluted with DCM (100 mL). The organic layer was washed with saturated NaHCO$_3$ solution (100 mL), brine solution (2×100 mL), dried over Na$_2$SO$_4$ and concentrated under reduced pressure to give the crude product which was taken to the next step without further purification (7.5 g, 73.6%).

MS (ES) m/z 355.5 (M$^+$+1)

Step (iii)

Synthesis of 2-amino-1-((S)-3-hydroxypyrrolidin-1-yl)-2-phenylethanone

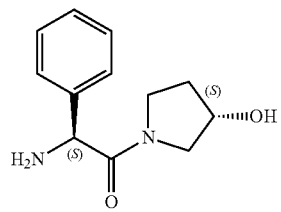

Experimental Procedure:

A mixture of benzyl (S)-2-(S)-3-hydroxypyrrolidin-1-yl)-2-oxo-1-phenylethyl carbamate (1 g) and 10% PD/C (100 mg) in methanol (10 mL) was hydrogenated over 2 h at room temperature. The reaction mixture was filtered through Celite bed and washed with methanol (20 mL) The combined organic layers were concentrated under reduced pressure to give the desired product as pale yellow mass (620 mg, %) which was used directly in the next step without further purification.

MS (ES) m/z 221.3 (M$^+$+1)

Step (iv)

Synthesis of (S)-1-((R)-2-amino-2-phenylethyl)pyrrolidin-3-ol

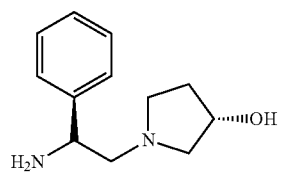

Experimental Procedure:

To lithium aluminum hydride (0.518 g, 13.6 mmoles) was added dry THF (10 mL) at 0° C. followed by 2-amino-14(S)-3-hydroxypyrrolidin-1-yl)-2-phenylethanone (0.6 g, 2.72 mmoles) dissolved in THF (10 mL). The reaction mixture was warmed to room temperature and then refluxed for 30 min. The reaction mixture was quenched with saturated Na$_2$CO$_3$ solution (2.5 mL) at 0° C. and triturated with ethyl acetate. The reaction mixture was filtered through celite bed and organic layer was concentrated under reduced pressure to give crude product. The crude product was purified by flash column chromatography over neutral Al$_2$O$_3$ to give the desired product as a yellow gummy mass (0.2 g, 35.6%).

Step (v)

Synthesis of 1-phenylcyclopropanecarbonitrile

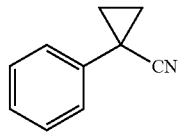 [SMILES: N#CC1(c2ccccc2)CC1]

Experimental Procedure

To a solution of NaH (12.6 g, 525 mmoles) in DMSO (300 mL) was added phenylacetonitrile (20 g, 170.9 mmoles) in DMSO at 0° C. and the mixture was stirred for 5 min. 1,2 dibromoethane (16.29 mL 86.6 mmoles) in DMSO was added to the reaction mixture and the contents were stirred for 2 h at about 20-35° C. The reaction mixture was treated with isopropanol (10 mL), ice cold water (150 mL) and extracted with ethyl acetate (200 mL). The organic layer was washed with brine solution (2×100 mL), dried over Na$_2$SO$_4$ and concentrated under reduced pressure to give the crude product. The crude was purified by flash chromatography over silica gel (230-400 mesh). Elution with 2% ethyl acetate in hexane, gave the desired product as a yellow liquid (10 g, 41%).

$^1$H NMR (400 MHz, DMSO-d$_6$): δ 7.42-7.29 (m, 5H), 1.80-1.69 (m, 2H), 1.55-1.44 (m, 2H)

Step (vi)

Synthesis of 1-phenylcyclopropanecarboxylic acid

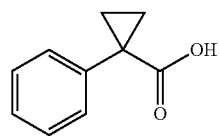 [SMILES: O=C(O)C1(c2ccccc2)CC1]

Experimental Procedure:

To a solution of 1-phenylcyclopropanecarbonitrile (7 g, mmoles) was added water (15 mL), acetic acid (15 mL) and sulfuric acid (15 mL). The contents were then refluxed at 110° C. over night. The reaction mixture was extracted with ethyl acetate and the organic layer was washed with brine solution (2×50 mL), dried over Na$_2$SO$_4$ and concentrated under reduced pressure to give the crude product. The crude was purified by flash column chromatography over silica gel (230-400 mesh) and elution with 5% ethyl acetate in hexane, gave the desired product as a colorless solid (4.35 g, 50%).

Step (vii)

Synthesis of (S)-1-phenyl-N-(1-phenyl-2-(pyrrolidin-1-yl)ethyl)cyclopropane carboxamide hydrochloride

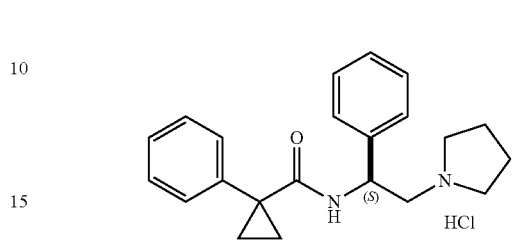

Experimental Procedure:

To a solution of 1-phenylcyclopropanecarboxylic acid (1 eq.), were added at about 20-35° C., DCC (1 eq) in DCM and 1-Hydroxybenzotriazole (1 eq.). The mixture was stirred for 10 min and to this mixture was added (S)-1-((R)-2-amino-2-phenylethyl)pyrrolidin-3-ol (1 eq) and the contents were allowed to stir at about 20-35° C. for 12 h. The reaction mixture was filtered, the filtrate was diluted with DCM and the organic layer was washed with sat.NaHCO$_3$ solution, brine and dried over Na$_2$SO$_4$ and concentrated under reduced pressure to give the crude product. The crude was purified by flash chromatography using silica gel (230-400 mesh) to give the desired product as a pale yellow gum. The resultant product is treated with hydrochloric acid to form the corresponding hydrochloric acid salt by following standard salt forming procedures known in the art.

$^1$H NMR (400 MHz, DMSO-d$_6$): δ 9.94 (s, 1H), 7.66 (d, J=8.7 Hz, 1H), 7.35-7.28 (m, 10H), 5.32 (t, J=8.1 Hz, 1H), 3.61-3.60 (m, 1H), 3.58-3.54 (m, 3H), 3.28-2.98 (m, 2H), 2.98-1.87 (m, 4H), 1.41 (t, J=6.9 Hz, 2H), 1.27-0.94 (m, 2H); IR (KBr, cm$^{-1}$): 3419, 2958, 2588, 2476, 1726, 1656, 1516, 1192, 1039;

MS: m/z (ES) 335.3 (M$^+$+1).

Examples 2-131 are prepared by employing appropriate starting materials and substantially following the procedures as set forth in Example 1:

Example 2

Synthesis of (S)—N-methyl-1-phenyl-N-(1-phenyl-2-(pyrrolidin-yl]ethyl]cyclopentane carboxamide hydrochloride

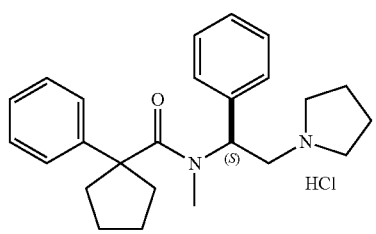

M.P: 220-221° C.

¹H NMR (400 MHz, DMSO-d₆): δ 10.0 (s, 1H), 7.38-7.14 (m, 10H), 6.20-6.17 (m, 1H), 3.95-3.90 (m, 1H), 3.89-3.71 (m, 1H), 3.5-3.3 (m, 2H), 3.1-3.0 (m, 2H), 2.5-2.4 (m, 2H), 2.24 (s, 3H), 2.3-2.2 (m, 1H), 2.1-1.8 (m, 4H), 1.8-1.4 (m, 5H)

IR (Neat, cm⁻¹): 3402, 2958, 2872, 2601, 1629, 1494, 1452, 1381

MS (ES): m/z 377.4 (M⁺+1)

Example 3

Synthesis of (S)—N-methyl-1-phenyl-N-(1-phenyl-2-(pyrrolidin-1-yl]ethyl]cyclohexane carboxamide hydrochloride

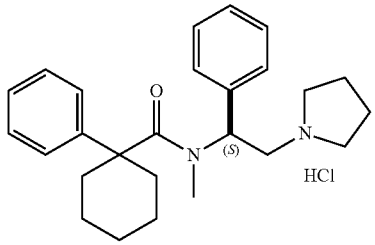

M.P: 232-233° C.

¹H NMR (400 MHz, DMSO-d₆): δ 10.2 (s, 1H), 7.39-7.16 (m, 10H), 6.15 (s, 1H), 3.85-3.80 (m, 2H), 3.62-3.56 (m, 1H), 3.43 (bs, 1H), 3.12-3.05 (m, 2H), 2.45 (m, 2H), 2.38-2.01 (s, 3H), 2.0-1.23 (m, 12H)

IR (KBr, cm⁻¹): 3466, 2937, 1624, 1496, 1452, 1371, 1085

MS (ES): m/z 391.4 (M⁺+1)

Example 4

Synthesis of (S)—N-methyl-1-phenyl-N-(1-phenyl-2-(pyrrolidin-1-yl]ethyl]cyclopropane carboxamide hydrochloride

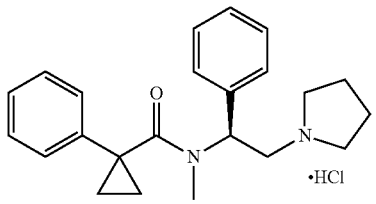 [SMILES: CN(C(=O)C1(c2ccccc2)CC1)[C@H](CN1CCCC1)c1ccccc1 ; Cl]

M.P: 216-217° C.

¹H NMR (400 MHz, DMSO-d₆): δ 9.9 (s, 1H), 7.39-7.08 (m, 10H), 6.1-6.09 (m, 1H), 4.02-4.0 (m, 1H), 3.68-3.65 (m, 1H), 3.64-3.54 (m, 2H), 3.27-3.0 (m, 2H), 2.5 (s, 3H), 1.99-1.92 (m, 4H), 1.90-1.61 (m, 1H), 1.48-1.40 (m, 2H), 0.86-0.81 (m, 1H)

IR (Neat, cm⁻¹): 3057, 2981, 2951, 2818, 2779, 2594, 2468, 1635, 1444, 1382, 1083

MS (ES): m/z 349.4 (M⁺+1)

Example 5

Synthesis of (S)—N-methyl-N-(1-phenyl-2-(pyrrolidin-1-yl)ethyl)-1-(quinolin-3-yl)cyclopropane carboxamide hydrochloride

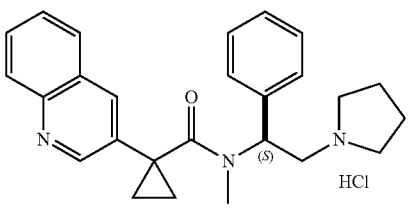

M.P: 223-225° C.

¹H NMR (400 MHz, DMSO-d₆): δ 10.40 (s, 1H), 8.77 (s, 1H), 8.19 (s, 1H), 8.04 (d, 8.3 Hz, 1H), 7.87 (d, J=7.8 Hz, 1H), 7.78 (d, J=7.7 Hz, 1H), 7.65 (t, J=7.7 Hz, 1H), 7.35 (m, 5H), 6.15 (t, J=5.4 Hz, 1H), 4.16 (t, J=10.7 Hz, 1H), 3.59 (m, 3H), 3.20 (t, J=9.3 Hz, 1H), 3.04 (t, J=8.8 Hz, 1H), 2.60 (s, 3H), 2.01 (m, 5H), 1.74 (t, J=10.7 Hz, 1H), 1.55 (m, 1H), 1.10 (m, 1H)

IR (KBr, cm⁻¹): 3321, 3064, 2966, 2580, 2040, 1627, 1585, 1573, 1454, 1392, 1334, 1303, 1255, 1211, 1155, 1105, 1083

MS (CI): m/z 400.5 (M⁺+1)

Example 6

Synthesis of (S)-1-phenyl-N-(1-phenyl-2-(pyrrolidin-1-yl)ethyl)cyclohexane carboxamide hydrochloride

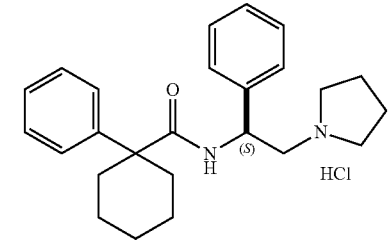

M.P: 204-205° C.

¹H NMR (400 MHz, DMSO-d₆): δ 10.15 (s, 1H), 8.13 (d, J=8.8 Hz, 1H), 7.38-7.17 (m, 10H), 5.25 (bs, 1H), 3.5-3.3 (m, 3H), 2.9 (m, 2H), 2.67-2.50 (m, 1H), 2.35 (m, 3H), 1.85-1.22 (m, 11H)

IR (KBr, cm⁻¹): 3286, 2924, 2852, 2673, 2571, 2470, 1712, 1664, 1523, 1232

MS (ES): m/z 377.3 (M⁺+1), 306.3 (M⁺−71)

Example 7

Synthesis of (S)—N-(1-phenyl-2-(pyrrolidin-1-yl) ethyl)-1-(pyridin-3-yl)cyclopropane carboxamide hydrochloride

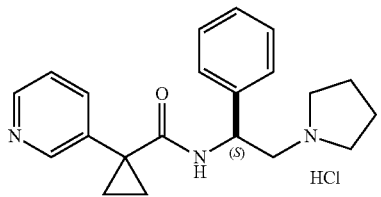

M.P: 150-152° C.
$^1$H NMR (400 MHz, DMSO-d$_6$): δ 9.03 (s, 1H), 8.77 (d, J=4.6 Hz, 1H), 8.44 (d, J=8.1 Hz, 1H), 8.06 (d, J=8.6 Hz, 1H), 7.90 (d, J=5.6 Hz, 1H), 7.31 (m, 5H), 5.35 (bs, 1H), 3.62-3.39 (m, 4H), 3.21-3.00 (m, 2H), 1.94 (m, 4H), 1.68 (bs, 1H), 1.54 (bs, 1H), 1.33-1.22 (m, 2H)
MS (ES) m/z 336.3 (M$^+$+1)

Example 8

Synthesis of (S)—N-(1-phenyl-2-(pyrrolidin-1-yl) ethyl)-1-(quinolin-3-yl)cyclopropane carboxamide hydrochloride

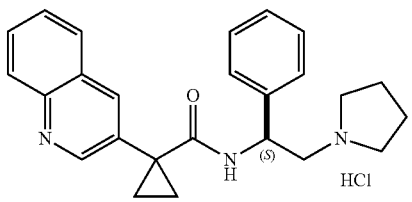

M.P: 176-178° C.
$^1$H NMR (400 MHz, DMSO-d$_6$): δ 10.39 (bs, 1H), 9.27 (bs, 1H), 8.74 (bs, 1H), 8.2 (d, J=8.6 Hz, 1H), 8.13 (d, J=8.1 Hz, 1H), 7.95 (m, 2H), 7.22 (m, 1H), 7.32 (m, 5H), 5.39 (t, J=8.4 Hz, 1H), 3.58-3.39 (m, 4H), 3.12-2.72 (m, 2H), 1.96-1.89 (m, 4H), 1.59-1.54 (m, 2H), 1.37-1.23 (m, 2H)
IR (Neat, cm$^{-1}$): 3410, 3253, 2956, 2594, 1656, 1647, 1525, 1452, 1365, 1300, 1215
MS (ES): m/z 386.3 (M$^+$+1)

Example 9

Synthesis of (S)—N-(1-phenyl-2-(pyrrolidin-1-yl) ethyl)-1-(pyridin-2-yl)cyclopropane carboxamide hydrochloride

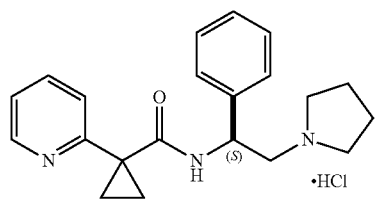

M.P: 107.1-107.3° C.
$^1$H NMR (400 MHz, DMSO-d$_6$): δ 8.40 (d, J=5.07 Hz, 1H), 7.73-7.71 (m, 1H), 7.57-7.52 (m, 1H), 7.48-7.45 (m, 1H), 7.31 (d, J=8.1 Hz, 1H), 7.25-7.16 (m, 4H), 5.09 (d, J=4.5 Hz, 1H), 3.21 (bs, 1H), 3.20-3.06 (m, 1H), 2.89-2.87 (m, 1H), 2.75 (bs, 3H), 1.77 (bs, 2H), 1.53-1.50 (m, 2H), 1.18 (bs, 4H)
IR (KBr, cm$^{-1}$): 2956, 2924, 2852, 1726, 1658, 1589, 1462, 1379, 1271, 1120, 1070
MS (ES): m/z 336.4 (M$^+$+1), 265.3 (M$^+$−70)

Example 10

Synthesis of N—((S)-2-((S)-3-hydroxypyrrolidin-1-yl)-1-phenylethyl)-1-(quinolin-3-yl)cyclopropane carboxamide hydrochloride

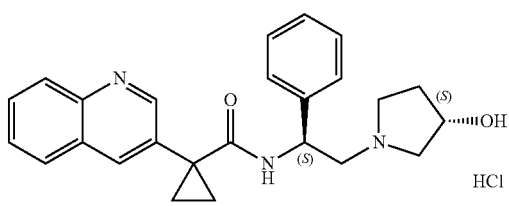

$^1$H NMR (400 MHz, DMSO-d$_6$): δ 10.3 (bs, 1H), 9.2 (bs, 1H), 8.68 (bs, 1H), 8.19-8.10 (m, 2H), 7.92 (t, J=7.9 Hz, 2H), 7.77 (t, J=7.9 Hz, 1H), 7.38-7.29 (m, 5H), 5.41 (bs, 1H), 4.4 (bs, 1H), 3.3-3.0 (m, 6H), 2.32-1.83 (m, 3H), 1.58 (bs, 2H), 1.34 (d, J=6.0 Hz, 1H), 1.23 (s, 1H)
IR (KBr, cm$^{-1}$): 3261, 3026, 2947, 2684, 2044, 1658, 1527, 1494, 1390, 1300, 1211, 1103
MS (ES): m/z 402 (M$^+$+1), 424 (M$^+$+Na)

Example 11

Synthesis of (S)—N-(3-methyl-1-(pyrrolidin-1-yl) butan-2-yl)-1-(quinolin-3-yl)cyclopropane carboxamide hydrochloride

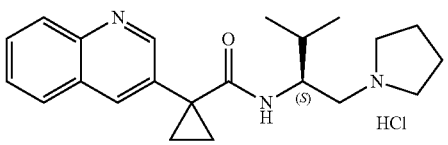

$^1$H NMR (400 MHz, DMSO-d$_6$): δ 10.26 (bs, 1H), 9.54 (s, 1H), 8.97 (s, 1H), 8.29 (d, J=8.5 Hz, 1H), 8.23 (d, J=8.2 Hz, 1H), 8.03 (t, J=7.6 Hz, 1H), 7.86 (t, J=7.6 Hz, 1H), 7.14 (d, J=9.1 Hz, 1H), 3.98-3.91 (m, 1H), 3.6 (t, J=6.4 Hz, 1H), 3.46 (d, J=5.5 Hz, 1H), 3.18 (d, J=5.7 Hz, 2H), 2.96 (t, J=7.3 Hz, 2H), 1.96-1.86 (m, 2H), 1.77-1.74 (m, 2H), 1.7-1.64 (m, 2H), 1.56-1.51 (m, 1H), 1.4-1.35 (m, 1H), 1.24-1.2 (m, 1H), 0.83 (d, J=6.7 Hz, 3H), 0.76 (d, J=6.7 Hz, 3H)
IR (Neat, cm$^{-1}$): 3414, 2962, 2607, 2054, 1647, 1523, 1207
MS (ES): m/z 351.9 (M$^+$+1)

Example 12

Synthesis of (S)-1-(benzo[d]oxazol-2-yl)-N-(1-phenyl-2-(pyrrolidin-1-yl)ethyl)cyclopropane carboxamide

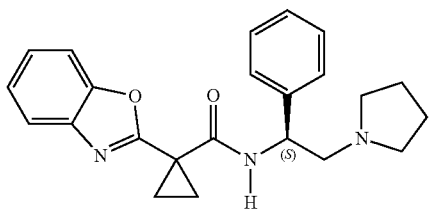

$^1$H NMR (400 MHz, DMSO-d$_6$): δ 9.43 (d, J=7.3 Hz, 1H), 7.72-7.66 (m, 2H), 7.41-7.22 (m, 7H), 4.98 (m, 1H), 2.86-2.69 (m, 2H), 2.50 (bs, 4H), 1.66 (m, 8H)

IR (Neat, cm$^{-1}$): 3288, 2960, 2792, 1666, 1562, 1456, 1367, 1244, 1118, 1093

MS (ES): m/z 376.1 (M$^+$+1)

Example 13

Synthesis of (S)—N-(1-phenyl-2-(pyrrolidin-1-yl)ethyl)-1-(4-phenylthiazol-2-yl)cyclopropane carboxamide

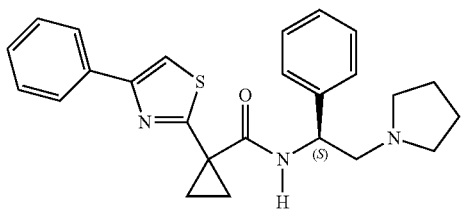

$^1$H NMR (400 MHz, DMSO-d$_6$): δ 8.99 (d, J=7.0 Hz, 1H), 8.02 (s, 1H), 7.94 (d, J=7.3 Hz, 2H), 7.21-7.46 (m, 8H), 4.96 (q, J=6.9 Hz, 1H), 3.39-2.96 (m, 1H), 2.96-2.83 (m, 2H), 2.67-2.60 (m, 1H), 2.50-2.45 (m, 2H), 1.90-1.46 (m, 8H)

IR (Neat, cm$^{-1}$): 3261, 3061, 3028, 2958, 2926, 2794, 1658, 1529, 1492, 1444, 1292, 1211, 1136, 1072

MS (ES): m/z 418.4 (M$^+$+1)

Example 14

Synthesis of (S)-1-(benzo[d][1,3]dioxol-5-yl)-N-(1-phenyl-2-(pyrrolidin-1-yl)ethyl)cyclopropane carboxamide

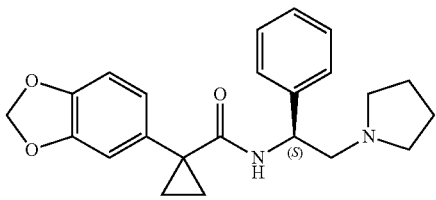

$^1$H NMR (400 MHz, DMSO-d$_6$): δ 7.29-7.18 (m, 5H), 7.18-7.00 (m, 4H), 6.0 (d, J=6.7 Hz, 2H), 4.70 (bs, 1H), 2.57 (m, 2H), 2.2 (bs, 4H), 1.57 (bs, 4H), 1.33-1.23 (m, 2H), 1.22-0.91 (m, 2H)

IR (KBr, cm$^{-1}$): 3348, 2960, 2927, 2792, 1666, 1489, 1438, 1350, 1292, 1230, 1035

MS (ES): m/z 379 (M$^+$+1)

Example 15

Synthesis of (S)-1-(benzo[d]thiazol-2-yl)-N-(1-phenyl-2-(pyrrolidin-1-yl)ethyl)cyclopropane carboxamide

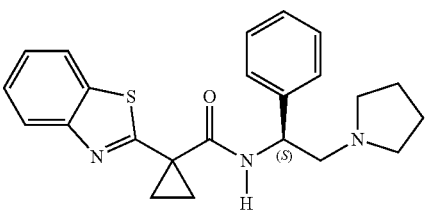

M.P: 97-99° C.

$^1$H NMR (400 MHz, CDCl$_3$): δ 9.81 (bs, 1H), 7.96 (d, J=7.9 Hz, 1H), 7.83 (d, J=7.93 Hz, 1H), 7.80-7.40 (m, 1H), 7.39-7.32 (m, 5H), 7.30-7.21 (m, 1H), 5.0 (bs, 1H), 3.52 (bs, 1H), 2.94 (bs, 1H), 2.78-2.74 (m, 1H), 2.58-2.31 (m, 3H), 2.07-1.95 (m, 2H), 1.94-1.69 (m, 4H), 1.45-1.36 (m, 2H)

MS (ES): m/z 392.3 (M$^+$+1)

Example 16

Synthesis of (S)-1-(3-cyanophenyl)-N-(1-phenyl-2-(pyrrolidin-1-yl)ethyl)cyclopropane carboxamide

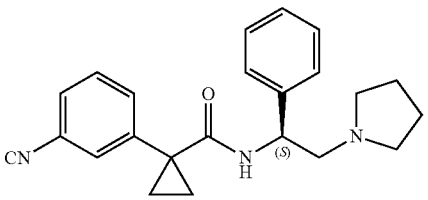

$^1$H NMR (400 MHz, CDCl$_3$): δ 7.77 (s, 1H), 7.72 (d, J=7.6 Hz, 1H), 7.64 (d, J=7.6 Hz, 1H), 7.54-7.46 (m, 1H), 7.33-7.14 (m, 5H), 6.49 (bs, 1H), 4.71-4.66 (m, 1H), 2.63-2.51 (m, 1H), 2.49-2.48 (m, 1H), 2.36 (bs, 2H), 2.24 (bs, 2H), 1.69-1.54 (m, 2H), 1.25 (bs, 4H), 1.12-1.07 (m, 1H), 1.03-0.86 (m, 1H)

MS (ES): m/z 360.3 (M$^+$+1)

Example 17

Synthesis of (S)—N-(2-(3-(hydroxymethyl)azetidin-1-yl)-1-phenylethyl)-1-(quinolin-3-yl)cyclopropane carboxamide

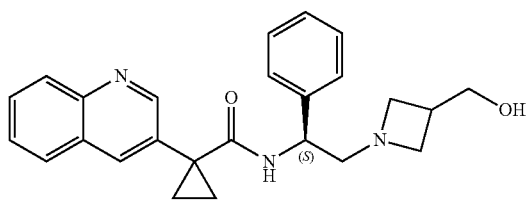

$^1$H NMR (400 MHz, DMSO-$d_6$): δ 8.88 (s, 1H), 8.31 (s, 1H), 8.04 (d, J=8.4 Hz, 1H), 7.97 (d, J=8.4 Hz, 1H), 7.77-7.73 (m, 1H), 7.62 (t, J=6.9 Hz, 1H), 7.39 (d, J=7.6 Hz, 1H), 7.29-7.17 (m, 5H), 4.76 (bs, 1H), 4.49 (bs, 1H), 3.36-3.32 (m, 2H), 3.03 (bs, 2H), 2.73-2.59 (m, 3H), 2.31 (bs, 1H), 1.49-1.40 (m, 2H), 1.23-1.17 (m, 3H)

IR (KBr, cm$^{-1}$): 3304, 2927, 2850, 1658, 1494, 1300, 1193, 1043

MS (ES): m/z 402.4 (M$^+$+1)

Example 18

Synthesis of (S)-1-(4-(methylsulfonamido)phenyl)-N-(1-phenyl-2-(pyrrolidin-1-yl)ethyl)cyclopropane carboxamide

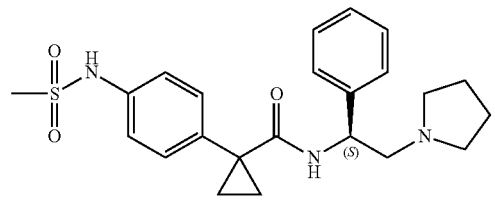

M.P: 165-168° C.
$^1$H NMR (400 MHz, DMSO-$d_6$): δ 9.80 (s, 1H), 7.37 (d, J=8.4 Hz, 2H), 7.29-7.18 (m, 7H), 6.99 (d, J=6.3 Hz, 1H), 4.72-4.71 (m, 1H), 2.98 (s, 3H), 2.97-2.55 (m, 2H), 2.31-2.26 (m, 4H), 1.57 (bs, 4H), 1.35-1.32 (m, Hi), 1.31-1.21 (m, 1H), 1.04-1.00 (m, 1H), 0.95-0.91 (m, 1H)

IR (KBr, cm$^{-1}$): 3329, 3124, 3032, 2931, 2872, 2800, 1631, 1612, 1514, 1402, 1338, 1153

MS (ES): m/z 428.4 (M$^+$+1)

Example 19

Synthesis of (S)-1-(3-(methylsulfonamido)phenyl)-N-(1-phenyl-2-(pyrrolidin-1-yl)ethyl)cyclopropane carboxamide

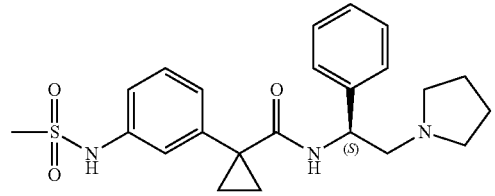

M.P: 146-148° C.
$^1$H NMR (400 MHz, DMSO-$d_6$): δ 9.77 (bs, 1H), 7.60-7.00 (m, 9H), 6.97 (d, J=6.6 Hz, 1H) 4.76-4.71 (m, 1H), 2.98 (s, 3H), 2.59-2.56 (m, 2H), 2.27-2.22 (m, 4H), 1.54 (bs, 4H), 1.36-1.26 (m, 2H), 1.02-0.96 (m, 2H)

IR (KBr, cm$^{-1}$): 3304, 3197, 3143, 3088, 3028, 3007, 2970, 2927, 2804, 1651, 1585, 1504, 1454, 1408, 1382, 1357, 1338, 1307, 1155

MS (ES): m/z 428.5 (M$^+$+1)

Example 20

Synthesis of (S)-1-(2-benzyl-2H-indazol-3-yl)-N-(1-phenyl-2-(pyrrolidin-1-yl)ethyl)cyclopropane carboxamide

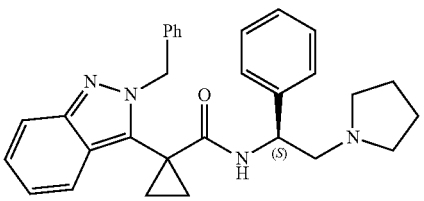

$^1$H NMR (400 MHz, DMSO-$d_6$): δ 7.70 (d, J=8.4 Hz, 2H), 7.40 (t, J=7.7 Hz, 1H), 7.31-7.13 (m, 12H), 5.71-5.61 (m, 2H), 4.96-4.79 (bs, 1H), 2.12 (bs, 4H), 1.49-1.23 (m, 10H)

IR (KBr, cm$^{-1}$): 3350, 2924, 2794, 1666, 1614, 1496, 1454, 1165

MS (ES): m/z 465.6 (M$^+$+1)

Example 21

Synthesis of (S)—N-(1-phenyl-2-(pyrrolidin-1-yl)ethyl)-1-m-tolylcyclopropanecarboxamide hydrochloride

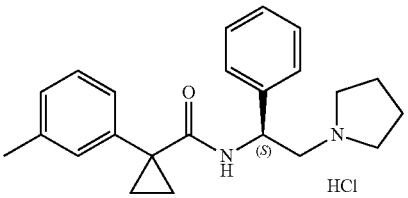

$^1$H NMR (400 MHz, DMSO-$d_6$): δ 9.90 (bs, 1H), 7.69 (d, J=8.7 Hz, 1H), 7.38-7.21 (m, 6H), 7.14-7.09 (m, 3H), 5.36-5.30 (m, 1H), 3.60 (bs, 1H), 3.58-3.38 (m, 3H), 3.09 (bs, 1H), 3.01 (bs, 1H), 2.2 (s, 3H), 1.97-1.82 (m, 4H), 1.39 (bs, 2H), 1.12-1.08 (m, 1H), 0.95-0.92 (m, 1H)

IR (KBr, cm$^{-1}$): 3267, 3032, 2954, 2584, 2472, 1712, 1687, 1658, 1494, 1452, 1265, 1224, 1047

MS (ES) m/z 349.1 (M$^+$+1)

Example 22

Synthesis of (S)-1-(3-hydroxyphenyl)-N-(1-phenyl-2-(pyrrolidin-1-yl)ethyl)cyclopropane carboxamide hydrochloride

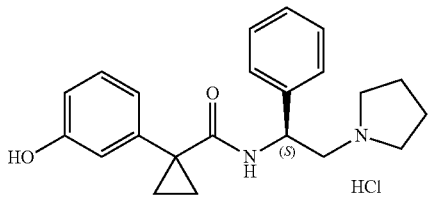

M.P: 80-82° C.
$^1$H NMR (400 MHz, DMSO-$d_6$): δ 10.01 (bs, 1H), 9.45 (bs, 1H), 7.62-7.60 (d, J=8.7 Hz, 1H), 7.37-7.26 (m, 5H), 7.14 (t, J=8.06 Hz, 1H), 6.78-6.68 (m, 3H), 5.36-5.30 (m, 1H), 3.63-3.55 (m, 1H), 3.44-3.37 (m, 3H), 3.08-3.04 (m, 1H), 2.99-2.95 (m, 1H), 1.96-1.80 (m, 4H), 1.35 (bs, 2H), 1.06-1.03 (m, 1H), 0.93-0.89 (m, 1H)
IR (KBr, cm$^{-1}$): 3240, 2956, 2681, 2600, 2474, 1658, 1583, 1494, 1446, 1327, 1217
MS (ES): m/z 351.4 (M$^+$+1)

Example 23

Synthesis of (S)-1-(3-(benzyloxy)phenyl)-N-(1-phenyl-2-(pyrrolidin-1-yl)ethyl)cyclopropane carboxamide hydrochloride

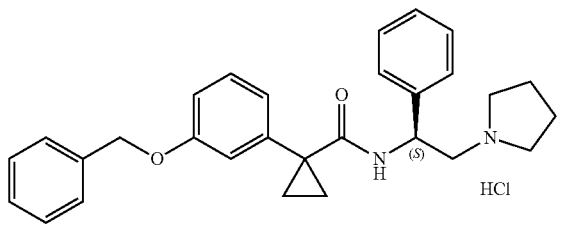

M.P: 118-120° C.
$^1$H NMR (400 MHz, DMSO-$d_6$): δ 9.74 (bs, 1H), 7.46-7.38 (m, 4H), 7.35-7.26 (m, 5H), 7.20-7.17 (m, 2H), 7.04-6.96 (m, 4H), 5.10 (s, 2H), 4.72 (q, J=6.5 Hz, 1H), 2.62-2.54 (m, 2H), 2.26 (bs, 4H), 1.53 (s, 4H), 1.35-1.30 (m, 2H), 1.07-1.04 (m, 1H), 1.03-0.97 (m, 1H)
IR (KBr, cm$^{-1}$): 3269, 2951, 2594, 1687, 1658, 1598, 1494, 1452, 1265, 1226
MS (ES): m/z 441.5 (M$^+$+1)

Example 24

Synthesis of (S)—N-(2-(3-hydroxyazetidin-1-yl)-1-phenylethyl)-1-(quinolin-3-yl)cyclopropane carboxamide

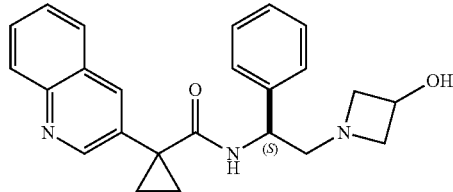

$^1$H NMR (400 MHz, DMSO-$d_6$): δ 8.85 (d, J=2.2 Hz, 1H), 8.30 (d, J=1.8 Hz, 1H), 8.03 (d, J=8.4 Hz, 1H), 7.97 (d, J=8.06 Hz, 1H), 7.75 (t, J=6.9 Hz, 1H), 7.62 (t, J=6.9 Hz, 1H), 7.43 (d, J=7.7 Hz, 1H), 7.29-7.17 (m, 5H), 5.20 (d, J=6.2 Hz, 1H), 4.77 (q, J=7.69 Hz, 1H), 4.00 (q, J=6.2 Hz, 1H), 2.65-2.53 (m, 4H), 1.48-1.42 (m, 2H), 1.23-1.14 (m, 4H)
MS (ES): m/z 388.3 (M$^+$+1)

Example 25

Synthesis of (S)-1-(3-(1H-tetrazol-5-yl)phenyl)-N-(1-phenyl-2-(pyrrolidin-1-yl)ethyl)cyclopropane carboxamide

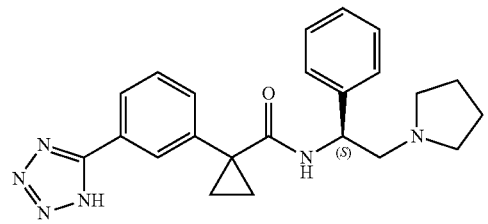

M.P: 137-139° C.
$^1$H NMR (400 MHz, DMSO-$d_6$): δ 8.04-7.93 (m, 2H), 7.39-7.12 (m, 9H), 4.81 (bs, 1H), 2.67 (bs, 2H), 2.37 (bs, 4H), 1.49 (bs, 4H), 1.38-1.23 (m, 2H), 1.04 (bs, 2H)
IR (KBr, cm$^{-1}$): 3365, 3061, 3028, 2964, 2926, 2796, 1658, 1502, 1415, 1352
MS (ES): m/z 401 (M$^+$1)

Example 26

Synthesis of (S)-1-(3-cyanophenyl)-N-(3-methyl-1-(pyrrolidin-1-yl)butan-2-yl)cyclopropane carboxamide

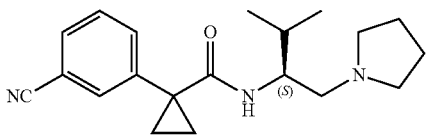

$^1$H NMR (400 MHz, DMSO-$d_6$): δ 7.70 (s, 1H), 7.73 (d, J=7.69 Hz, 1H), 7.68-7.66 (m, 1H), 7.55-7.51 (m, 1H), 6.70 (d, J=7.6 Hz, 1H), 3.72 (bs, 1H), 2.67-2.33 (m, 7H), 1.74-1.67 (m, 4H), 1.33 (bs, 2H), 1.08 (bs, 2H), 0.79 (d, J=6.6 Hz, 3H), 0.71 (d, J=6.6 Hz, 3H)
IR (KBr, cm$^{-1}$): 3373, 2960, 2873, 2789, 2229, 1660, 1512, 1502, 1298
MS (ES): m/z 326.4 (M$^+$+1)

Example 27

Synthesis of N4(S)-2-(S)-3-hydroxy pyrrolidin-1-yl)-1-phenylethyl)-1-(3-(methylsulfonamido)phenyl) cyclopropane carboxamide

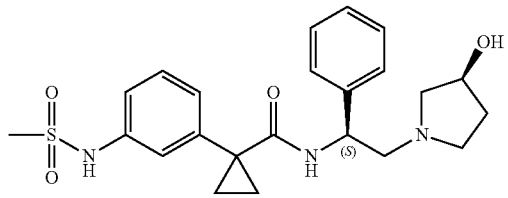

$^1$H NMR (400 MHz, DMSO-d$_6$): δ 9.76 (s, 1H), 7.36-7.15 (m, 9H), 6.97 (d, J=5.8 Hz, 1H), 4.76 (d, J=5.1 Hz, 1H), 4.61 (bs, 1H), 4.06 (bs, 1H), 2.98 (s, 3H), 2.67-2.57 (m, 3H), 2.34-2.28 (m, 2H), 2.11 (s, 1H), 1.81-1.76 (m, 1H), 1.41 (bs, 1H), 1.40-1.23 (m, 2H), 0.99-0.98 (m, 2H)

IR (Neat, cm$^{-1}$): 3412, 3010, 2931, 2810, 1643, 1502, 1327, 1151

MS (ES): m/z 444.5 (M$^+$+1)

Example 28

Synthesis of (S)-4-(1-(1-phenyl-2-(pyrrolidin-1-yl) ethyl carbamoyl)cyclopropyl)phenylmethane sulfonate hydrochloride

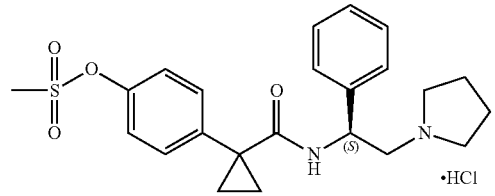

M.P: 102-104° C.

$^1$H NMR (400 MHz, DMSO-d$_6$): δ 7.52-7.50 (m, 2H), 7.35-7.33 (m, 2H), 7.30-7.18 (m, 5H), 7.14 (d, J=6.2 Hz, 1H), 4.78-4.73 (m, 1H), 3.38 (s, 3H), 2.66-2.60 (m, 1H), 2.53 (d, J=5.5 Hz, 1H), 2.31-2.27 (m, 4H), 1.57 (bs, 4H), 1.39-1.35 (m, 1H), 1.29-1.23 (m, 1H), 1.11-1.06 (m, 1H), 1.02-0.98 (m, 1H)

IR (KBr, cm$^{-1}$): 3419, 3010, 2933, 2600, 1658, 1502, 1361, 1151

MS (ES): m/z 429.4 (M$^+$+1)

Example 29

Synthesis of 4-(1-((S)-2-((S)-3-hydroxypyrrolidin-1-yl)-1-phenylethylcarbamoyl)cyclopropyl)phenyl methanesulfonate hydrochloride

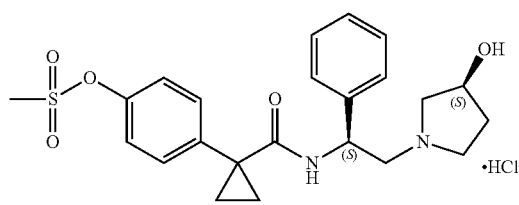

M.P: 60-62° C.

$^1$H NMR (400 MHz, DMSO-d$_6$): δ 7.50 (d, J=8.4 Hz, 2H), 7.34 (d, J=8.4 Hz, 2H) 7.30-7.18 (m, 6H), 4.77 (bs, 1H), 4.63 (bs, 1H), 4.09 (bs, 1H), 3.37 (s, 3H), 2.70-2.64 (m, 2H), 2.45-2.33 (m, 2H), 2.17 (bs, 1H), 1.86-1.80 (m, 1H), 1.47-1.45 (m, 1H), 1.38-1.30 (m, 1H), 1.24 (bs, 2H), 1.09-1.05 (m, 1H), 1.05-0.85 (m, 1H)

IR (KBr, cm$^{-1}$): 3327, 3010, 2926, 1658, 1502, 1442, 1363, 1151

MS (ES): m/z 445.4 (M$^+$+1)

Example 30

Synthesis of (S)—N-(3-methyl-1-(pyrrolidin-1-yl) butan-2-yl)-1-(3-(methyl sulfonamido)phenyl)cyclopropane carboxamide

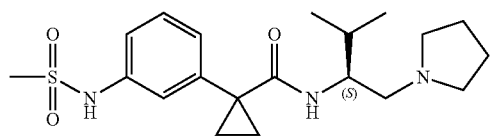

$^1$H NMR (400 MHz, DMSO-d$_6$): δ 9.7 (bs, 1H), 7.32 (t, J=7.7 Hz, 1H), 7.2 (d, J=1.9 Hz, 1H), 7.15 (s, 1H), 7.13 (t, J=6.5 Hz, 1H), 6.1 (d, J=8.4 Hz, 1H), 3.6 (t, J=6.2 Hz, 1H), 2.97 (s, 3H), 2.37 (bs, 6H), 1.79-171 (m, 1H), 1.62 (bs, 4H), 1.36-1.28 (m, 2H), 1.01-0.91 (m, 2H), 0.77 (d, J=7.0 Hz, 3H), 0.67 (d, J=6.6 Hz, 3H)

IR (Neat, cm$^{-1}$): 3421, 3151, 2960, 2792, 1641, 1604, 1587, 1512, 1467, 1402, 1328, 1155

MS (ES): m/z 394.5 (M$^+$+1)

Example 31

Synthesis of 3-(1-((S)-2((S)-3-hydroxypyrrolidin-1-yl)-1-phenylethylcarbamoyl)cyclopropyl)phenyl methane sulfonate

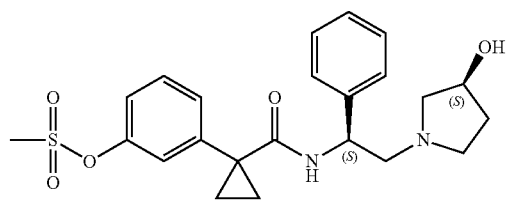

$^1$H NMR (400 MHz, DMSO-d$_6$): δ 7.50-7.46 (m, 1H), 7.43-7.41 (m, 1H), 7.35 (s, 1H), 7.29-7.26 (m, 2H), 7.23-7.19 (m, 5H), 4.81-4.76 (m, 1H), 4.61 (bs, 1H), 4.15-4.08 (m, 1H), 3.37 (s, 3H), 3.16 (d, J=5.2 Hz, 2H), 2.69-2.60 (m, 2H), 2.33 (s, 2H), 2.16 (bs, 1H), 1.83-1.79 (m, 1H), 1.43-1.35 (m, 2H), 1.06 (bs, 2H)

IR (KBr, cm$^{-1}$): 2933, 1656

MS (ES): m/z 445.3 (M$^+$+1)

Example 32

Synthesis of (S)-3-(1-(1-phenyl-2-(pyrrolidin-1-yl)ethyl carbamoyl)cyclopropyl)phenylmethane sulfonate

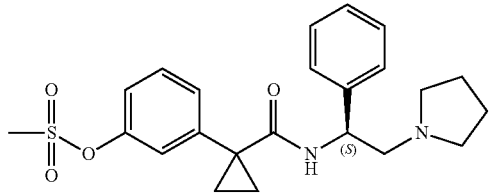

$^1$H NMR (400 MHz, DMSO-d$_6$): δ 7.50-7.10 (m, 10H), 4.79 (bs, 1H), 3.37 (s, 3H), 2.66-2.62 (m, 2H), 2.30-2.28 (m, 4H), 1.56 (bs, 4H), 1.38-1.27 (m, 2H), 1.17-1.02 (m, 2H)

IR (KBr, cm$^{-1}$): 3714, 3348, 3012, 2962, 2933, 2875, 2796, 1664, 1604, 1581, 1492, 1440, 1367, 1300, 1188, 1151, 1099, 1029

MS (ES): m/z 429.3 (M$^+$+1)

Example 33

Synthesis of N—((S)-2-((R)-3-fluoropyrrolidin-1-yl)-1-phenylethyl)-1-(quinolin-3-yl)cyclopropane carboxamide

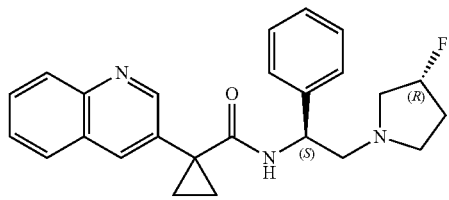

$^1$H NMR (400 MHz, DMSO-d$_6$): δ 8.86 (s, 1H), 8.28 (s, 1H), 8.03 (d, J=8.4 Hz, 1H), 7.95 (d, J=7.7 Hz, 1H), 7.75 (t, J=7.3 Hz, 1H), 7.62 (t, J=7.7 Hz, 1H), 7.45 (d, J=7.7 Hz, 1H), 7.3-7.18 (m, 5H), 5.15 (s, 0.5H), 5.01 (s, 0.5H), 4.99-4.91 (m, 1H), 2.74-2.52 (m, 5H), 2.3 (m, 1H), 2.02-1.71 (m, 2H), 1.5-1.3 (m, 2H), 1.23-1.12 (m, 2H)

IR (KBr, cm$^{-1}$): 3323, 3061, 2953, 2804, 1666, 1602, 1570, 1492, 1452, 1294, 1141, 1089

MS (ES): m/z 404.5 (M$^+$+1)

Example 34

Synthesis of N—((S)-2-((R)-3-hydroxypyrrolidin-1-yl)-1-phenylethyl)-1-(quinolin-3-yl)cyclopropane carboxamide

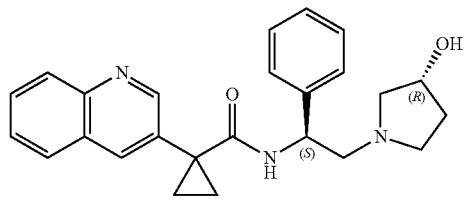

$^1$H NMR (400 MHz, DMSO-d$_6$): δ 8.88 (s, 1H), 8.32 (s, 1H), 8.03 (d, J=8.06 Hz, 1H), 7.98 (d, J=7.7 Hz, 1H), 7.75 (t, J=6.9 Hz, 1H), 7.62 (t, J=7.7 Hz, 1H), 7.38 (d, J=6.9 Hz, 1H), 7.29-7.17 (m, 5H), 4.86 (d, J=5.5 Hz, 1H), 4.64 (bs, 1H), 4.0 (bs, 1H), 2.7-2.4 (m, 6H), 2.2-2.16 (m, 1H), 1.76-1.69 (m, 1H), 1.51-1.37 (m, 2H), 1.24-1.12 (m, 2H)

IR (KBr, cm$^{-1}$): 3338, 2941, 2802, 1658, 1494, 1442, 1298, 1207, 1139, 1095, 1029

MS (ES): m/z 402.2 (M$^+$+1)

Example 35

Synthesis of N—((S)-2-((R)-3-hydroxypyrrolidin-1-yl)-1-phenylethyl)-1-(3-(methylsulfonamido)phenyl)cyclopropane carboxamide

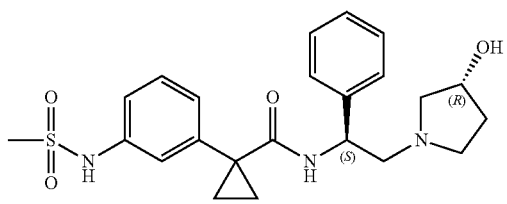

$^1$H NMR (400 MHz, DMSO-d$_6$): δ 9.7 (s, 1H), 7.36-7.15 (m, 9H), 6.98 (d, J=6.6 Hz, 1H), 4.70 (m, 1H), 4.66 (bs, 1H), 4.03 (bs, 1H), 2.98 (s, 3H), 2.67-2.32 (m, 5H), 2.09 (bs, 1H), 1.83-1.78 (m, 1H), 1.46-1.43 (m, 1H), 1.35-1.23 (m, 2H), 0.99 (s, 2H)

IR (KBr, cm$^{-1}$): 3086, 3028, 2945, 2910, 2802, 1649, 1604, 1585, 1502, 1442, 1402, 1327, 1153, 1095

MS (ES): m/z 444.5 (M$^+$+1)

Example 36

Synthesis of N—((S)-2-(S)-3-fluoropyrrolidin-1-yl)-1-phenylethyl)-1-(quinolin-3-yl)cyclopropane carboxamide

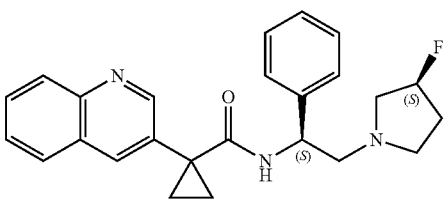

$^1$H NMR (400 MHz, DMSO-d$_6$): δ 8.87 (d, 1H), 8.3 (d, 1H), 8.03 (d, J=8.4 Hz, 1H), 7.96 (d, J=8.06 Hz, 1H), 7.75 (t, J=8.4 Hz, 1H), 7.61 (t, J=7.3 Hz, 1H), 7.43 (d, J=7.7 Hz, 1H), 7.3-7.18 (m, 5H), 5.12 (bs, 0.5H), 4.98 (bs, 0.5H), 4.94-4.89 (m, 1H), 2.73-2.53 (m, 4H), 2.32-2.21 (m, 2H), 1.98-1.64 (m, 2H), 1.51-1.37 (m, 2H), 1.23-1.13 (m, 2H)

IR (Neat, cm$^{-1}$): 3336, 3061, 3005, 2962, 2806, 1664, 1492, 1300, 1247, 1193, 1139, 1089

MS (ES): m/z 404.4 (M$^+$+1)

Example 37

Synthesis of N—((S)-2-((S)-3-hydroxypyrrolidin-1-yl)-1-phenylethyl)-1-(3-isocyanophenyl)cyclopropane carboxamide

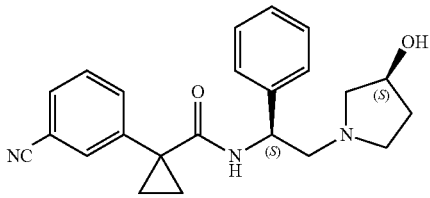

$^1$H NMR (400 MHz, DMSO-d$_6$): δ 7.79-7.71 (m, 3H), 7.56 (t, J=7.7 Hz, 1H), 7.34 (d, J=6.96 Hz, 1H), 7.30-7.18 (m, 5H), 4.82 (q, J=7.08 Hz, 1H), 4.64 (d, J=4.03 Hz, 1H), 4.12 (bs, 1H), 2.75-2.64 (m, 2H), 2.53-2.32 (m, 3H), 2.16 (q, J=4.3 Hz, 1H), 1.98-1.81 (m, 1H), 1.49-1.05 (m, 5H)

IR (KBr, cm$^{-1}$): 3377, 3062, 3028, 3007, 2941, 2808, 2229, 1651, 1579, 1496, 1446, 1417, 1300

MS (ES): m/z 376.3 (M$^+$+1)

Example 38

Synthesis of N—((S)-2-((S)-3-hydroxypyrrolidin-1-yl)-1-phenylethyl)-1-(quinoxalin-2-yl)cyclopropane carboxamide

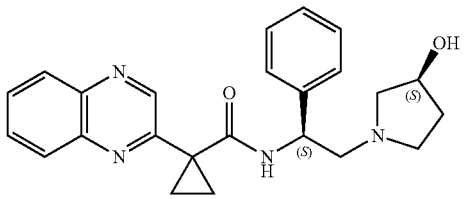

$^1$H NMR (400 MHz, DMSO-d$_6$): δ 8.96 (s, 1H), 8.49 (d, J=8.0 Hz, 1H), 8.10-8.01 (m, 2H), 7.87-7.79 (m, 2H), 7.33-7.20 (m, 51-1), 5.07 (bs, 1H), 4.70 (bs, 1H), 4.18 (bs, 1H), 2.89-2.82 (m, 1H), 2.79-2.67 (m, 1H), 2.67-2.49 (m, 3H), 2.32 (bs, 1H), 2.00-1.92 (m, 1H), 1.55-1.47 (m, 5H)

IR (KBr, cm$^{-1}$): 3292, 3061, 3028, 2941, 2802, 1641, 1535, 1492, 1442, 1431, 1217, 1151, 1099, 1032

MS (ES): m/z 403.3 (M$^+$+1)

Example 39

Synthesis of (S)—N-(1-phenyl-2-(pyrrolidin-1-yl)ethyl)-1-(quinoxalin-2-yl)cyclopropane carboxamide

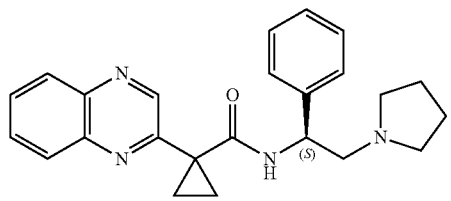

$^1$H NMR (400 MHz, CDCl$_3$): δ 8.78 (s, 1H), 8.65 (bs, 1H), 8.12-8.06 (m, 2H), 7.82-7.74 (m, 2H), 7.33-7.20 (m, 5H), 4.98-4.93 (m, 1H), 2.85 (t, J=11.0 Hz, 1H), 2.64-2.59 (m, 1H), 2.47 (bs, 2H), 2.39 (bs, 2H), 1.92-1.80 (m, 4H), 1.65-1.43 (bs, 4H)

IR (KBr, cm$^{-1}$): 3230, 3007, 2957, 2602, 2478, 1657, 1529, 1492, 1450, 1367, 1215, 1099

MS (ES): m/z 387.3 (M$^+$+1)

Example 40

Synthesis of (S)—N-(1-phenyl-2-(pyrrolidin-1-yl)ethyl)-1-(pyridin-4-yl)cyclopropane carboxamide

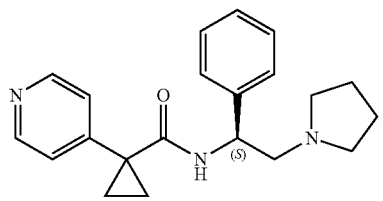

$^1$H NMR (400 MHz, DMSO-d$_6$): δ 8.47 (d, J=5.8 Hz, 2H), 7.68 (d, J=7.3 Hz, 1H), 7.34-7.19 (m, 7H), 4.89 (bs, 1H), 2.78-2.72 (t, J=10.4 Hz, 1H), 2.50-2.28 (m, 5H), 1.63 (s, 4H), 1.41-1.04 (m, 4H)

IR (Neat, cm$^{-1}$): 3329, 3026, 2960, 2792, 1664, 1597, 1492, 1408, 1355, 1296, 1211, 1136, 1068

MS (ES): m/z 336.1 (M$^+$+1)

Example 41

Synthesis of N—((S)-2-((S)-3-hydroxypyrrolidin-1-yl)-1-phenylethyl)-1-(pyridin-4-yl)cyclopropane carboxamide

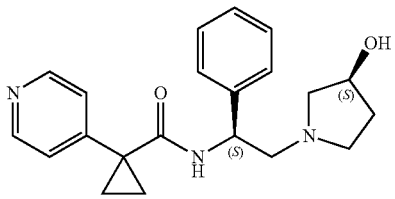

M.P: 112-114° C.

$^1$H NMR (400 MHz, DMSO-d$_6$): δ 8.49 (d, J=5.8 Hz, 2H), 7.7 (d, J=7.6 Hz, 1H), 7.20-7.34 (m, 7H), 4.9 (d, J=4.3 Hz, 1H), 4.68 (bs, 1H), 4.15 (bs, 1H), 2.73-2.67 (m, 2H), 2.58-2.56 (m, 1H), 2.37-2.20 (m, 3H), 1.86-1.95 (m, 1H), 1.07-1.51 (m, 5H)

IR (KBr, cm$^{-1}$): 3425, 3315, 2941, 2810, 1654, 1635, 1600, 1529, 1494, 1440, 1409, 1382, 1334, 1290, 1215, 1155

MS (ES) m/z 352.4 (M$^+$+1)

Example 42

Synthesis of (S)-1-(4-(N,N-dimethylsulfamoyl)phenyl)-N-(1-phenyl-2-(pyrrolidin-1-yl) ethyl)cyclopropane carboxamide

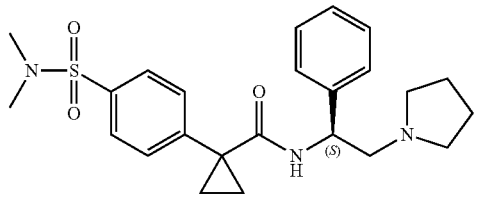

$^1$H NMR (400 MHz, DMSO-d$_6$): δ 7.71 (d, J=8.06 Hz, 2H), 7.63 (d, J=8.06 Hz, 2H), 7.34 (d, J=6.6 Hz, 1H), 7.30-7.18 (m, 5H), 4.84-4.79 (m, 1H), 2.70-2.67 (m, 2H), 2.65 (s, 6I-1), 2.58-2.30 (m, 4H), 1.56-1.50 (m, 4H), 1.44-1.40 (m, 1H), 1.39-1.30 (m, 1H), 1.18-1.13 (m, 1H), 1.08-1.05 (m, 1H)

IR (Neat, cm$^{-1}$): 3332, 2958, 2924, 2800, 1664, 1493, 1342, 1163

MS (ES): m/z 442.4 (M$^+$+1)

Example 43

Synthesis of (S)-1-(4-(methylsulfonamidomethyl)phenyl)-N-(1-phenyl-2-(pyrrolidin-1-yl)ethyl)cyclopropane carboxamide

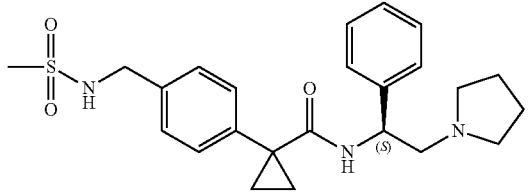

$^1$H NMR (400 MHz, DMSO-d$_6$): δ 7.53 (t, J=6.4 Hz, 1H), 7.40-7.37 (m, 2H), 7.35-7.30 (m, 2H), 7.30-7.24 (m, 2H), 7.20-7.15 (m, 3H), 6.99 (d, J=5.9 Hz, 1H), 4.73 (d, J=8.4 Hz, 1H), 4.15 (d, J=6.2 Hz, 2H), 2.86 (s, 3H), 2.56-2.48 (bs, 1H), 2.36-2.24 (m, 5H), 1.58-1.48 (bs, 4H), 1.36-1.34 (m, 1H), 1.32-1.25 (m, 1H), 1.08-1.00 (m, 1H), 0.98-0.94 (m, 1H)

IR (KBr, cm$^{-1}$): 3203, 2961, 2930, 2873, 2799, 1726, 1649, 1502, 1444, 1411, 1323, 1149, 1068

MS (ES): m/z 442.5 (M$^+$+1)

Example 44

Synthesis of N—((S)-2-(S)-3-hydroxypyrrolidin-1-yl)-1-phenyl ethyl)-1-(4-(methyl sulfonamide methyl)phenyl)cyclopropane carboxamide

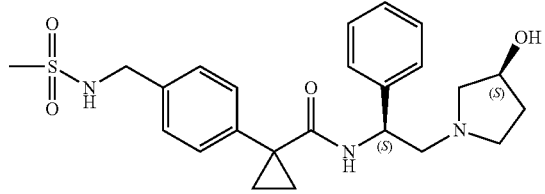

$^1$H NMR (400 MHz, DMSO-d$_6$): δ 7.53 (t, J=6.4 Hz, 1H), 7.40-7.36 (m, 2H), 7.35-7.31 (m, 2H), 7.30-7.24 (m, 2H), 7.20-7.15 (m, 3H), 6.97 (d, J=6.6 Hz, 1H), 4.80-4.72 (m, 1H), 4.60 (d, J=4.4 Hz, 1H), 4.20-4.16 (m, 2H), 4.14-4.04 (m, 1H), 2.86 (s, 3H), 2.68-2.60 (m, 2H), 2.58-2.54 (m, 1H), 2.41-2.35 (m, 1H), 2.32-2.26 (m, 1H), 2.21-2.16 (m, 1H), 1.85-1.76 (m, 1H), 1.48-1.40 (m, 1H), 1.38-1.34 (m, 1H), 1.32-1.24 (m, 1H), 1.08-1.00 (m, 1H), 0.98-0.94 (m, 1H)

IR (KBr, cm$^{-1}$): 3421, 2916, 2849, 2810, 1726, 1641, 1502, 1382, 1323, 1147, 1070

MS (ES): m/z 458.4 (M$^+$+1)

Example 45

Synthesis of (S)-1-(3-(methylsulfonamidomethyl)phenyl)-N-(1-phenyl-2-(pyrrolidin-1-yl)ethyl)cyclopropane carboxamide

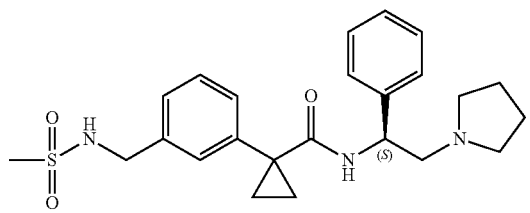

$^1$H NMR (400 MHz, DMSO-d$_6$): δ 7.56 (t, J=6.2 Hz, 1H), 7.39-7.30 (m, 6H), 7.28-7.19 (m, 3H), 6.94 (d, J=6.59 Hz, 1H), 4.74-4.73 (m, 1H), 4.18-4.16 (d, J=5.8 Hz, 2H), 2.84 (s, 3H), 2.61-2.50 (m, 2H), 2.32-2.20 (m, 4H), 1.54 (bs, 4H), 1.37-1.23 (m, 2H), 1.15-1.00 (m, 2H)

IR (KBr, cm$^{-1}$): 3217, 2958, 2926, 2798, 1651, 1502, 1492, 1442, 1323, 1190, 1149, 1066

MS (ES): m/z 442.5 (M$^+$+1)

Example 46

Synthesis of N—((S)-2-((S)-3-hydroxypyrrolidin-1-yl)-1-phenyl ethyl)-1-(3-(methylsulfonamidomethyl)phenyl)cyclopropane carboxamide

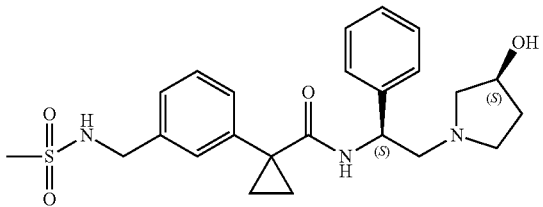

$^1$H NMR (400 MHz, DMSO-d$_6$): δ 7.54 (t, J=6.22 Hz, 1H), 7.38-7.17 (m, 9H), 6.92 (d, J=5.9 Hz, 1H), 4.73 (bs, 1H), 4.62 (bs, 1H), 4.17 (d, J=5.9 Hz, 2H), 4.01 (bs, 1H), 2.97 (s, 3H), 2.66-2.49 (m, 3H), 2.44-2.32 (m, 2H), 2.29-2.12 (m, 1H), 1.82-1.79 (m, 1H), 1.42-1.23 (m, 3H), 1.19-1.00 (m, 2H)

IR (KBr, cm$^{-1}$): 3387, 2929, 2810, 1641, 1502, 1442, 1321, 1147, 1093, 1066

MS (ES): m/z 458.4 (M$^+$+1)

Example 49

Synthesis of N—((S)-2-((S)-3-(dimethylamino)pyrrolidin-1-yl)-1-phenylethyl)-1-(3-(methylsulfonamido)phenyl)cyclopropanecarboxamide

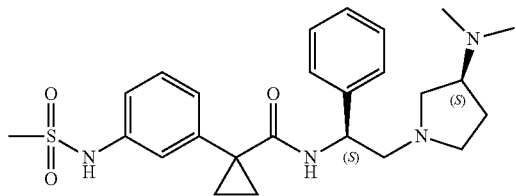

$^1$H NMR (400 MHz, DMSO-d$_6$): δ 7.37-7.33 (m, 1H), 7.27-7.15 (m, 8H), 6.91 (d, J=6.96 Hz, 1H), 4.77 (q, J=6.59 Hz, 1H), 2.99 (s, 3H), 2.69-2.61 (m, 3H), 2.41-2.39 (m, 1H), 2.37-2.26 (m, 1H), 2.14-2.10 (m, 1H), 2.02 (s, 6H), 1.68-1.63 (m, 1H), 1.47-1.23 (m, 5H)

IR (KBr, cm$^{-1}$): 2956, 2924, 2852, 1726, 1641, 1604, 1500, 1469, 1328, 1286, 1273, 1219 1153, 1072

MS (ES): m/z 471.5 (M$^+$+1)

Example 48

Synthesis of N—((S)-2-((S)-3-(dimethylamino)pyrrolidin-1-yl)-1-phenylethyl)-1-(quinolin-2-yl)cyclopropane carboxamide

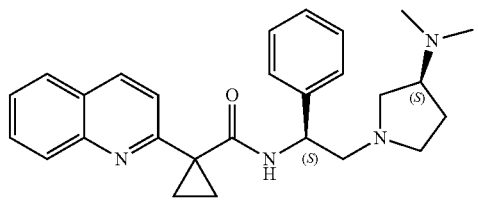

$^1$H NMR (400 MHz, DMSO-d$_6$): δ 8.90 (s, 1H), 8.33 (s, 1H), 8.03 (d, J=8.4 Hz, 1H), 7.98 (d, J=8.06 Hz, 1H), 7.99-7.42 (m, 1H), 7.64-7.61 (m, 1H), 7.31-7.17 (m, 6H), 4.88-4.84 (m, 1H), 2.67-2.11 (m, 6H), 2.05 (s, 6H), 1.56-1.37 (m, 4H), 1.23-1.20 (m, 3H)

IR (KBr, cm$^{-1}$): 3348, 2949, 2926, 2816, 2781, 1664, 1492, 1357, 1300, 1193, 1153, 1093, 1037

MS (ES): m/z 429.4 (M$^+$+1)

Example 49

Synthesis of (S)-1-(4-(methylsulfonyl)phenyl)-N-(1-phenyl-2-(pyrrolidin-1-yl)ethyl)cyclopropane carboxamide

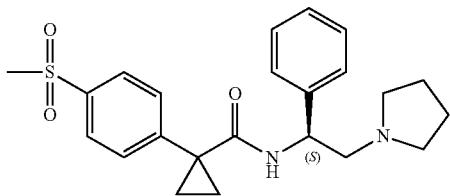

M.P: 150-152° C.

$^1$H NMR (400 MHz, DMSO-d$_6$): δ 7.90 (d, J=8.06 Hz, 2H), 7.66 (d, J=8.06 Hz, 2H), 7.41 (d, J=6.2 Hz, 1H), 7.33-7.23 (m, 5H), 4.83-4.80 (m, 1H), 3.19 (s, 3H), 2.69-2.66 (m, 1H), 2.54-2.40 (m, 1H), 2.34-2.30 (m, 4H), 1.58 (bs, 4H), 1.32-1.43 (m, 2H), 1.23-1.03 (m, 2H)

IR (KBr, cm$^{-1}$): 3364, 2918, 1666, 1483, 1310, 1153, 1101

MS (ES): m/z 411.3 (M$^+$−1)

Example 50

Synthesis of (S)-1-(2-(N,N-dimethyl sulfamoyl)phenyl)-N-(1-phenyl-2-(pyrrolidin-1-yl)ethyl)cyclopropane carboxamide

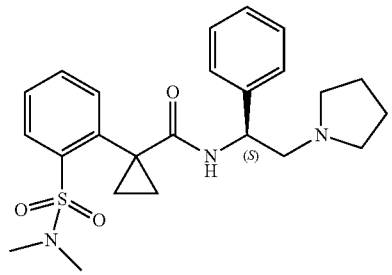

M.P: 80-81° C.

$^1$H NMR (400 MHz, DMSO-d$_6$): δ 7.77 (d, J=7.8 Hz, 1H), 7.70-7.65 (m, 2H), 7.60-7.54 (m, 1H), 7.28-7.24 (m, 4H), 7.18-7.15 (m, 1H), 6.56-6.52 (bs, 1H), 4.62-4.58 (bs, 1H), 2.80 (s, 6H), 2.34-2.25 (bs, 2H), 2.22-2.16 (m, 4H), 1.48-1.42 (bs, 4H), 1.24-1.20 (m, 2H), 1.17-1.13 (m, 2H)

IR (KBr, cm$^{-1}$): 3348, 2960, 2926, 2875, 2801, 1666, 1495, 1331, 1157

MS (ES): m/z 442.4 (M$^+$+1)

Example 51

Synthesis of (S)-1-(3-(methylsulfonyl)phenyl)-N-(1-phenyl-2-(pyrrolidin-1-yl)ethyl)cyclopropane carboxamide hydrochloride

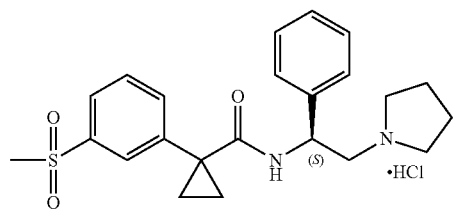

M.P: 68-70° C.

$^1$H NMR (400 MHz, DMSO-d$_6$): δ 9.88 (bs, 1H), 7.91 (s, 1H), 7.71-7.87 (m, 2H), 7.61-7.79 (m, 2H), 7.30-7.37 (m, 5H), 5.33 (t, J=8.0 Hz, 1H), 3.21 (s, 3H), 3.00-3.16 (m, 4H), 1.88-1.97 (m, 4H), 1.50-1.53 (m, 2H), 1.23 (s, 2H), 1.03-1.10 (m, 2H)

IR (KBr, cm$^{-1}$): 2959, 2683, 2478, 1726, 1658, 1452, 1514, 1296, 1150

MS (ES): m/z 413.4 (M$^+$+1)

Example 52

Synthesis of (S)-1-(3-methoxyphenyl)-N-(1-phenyl-2-(pyrrolidin-1-yl)ethyl)cyclopropane carboxamide

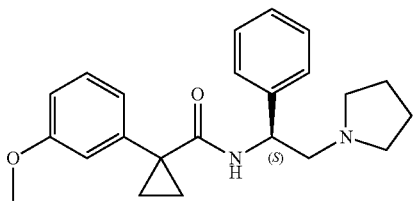

$^1$H NMR (400 MHz, DMSO-d$_6$): δ 7.32-7.17 (m, 6H), 6.88-7.02 (m, 4H), 4.70 (q, J=6.6 Hz, 1H), 3.76 (s, 3H), 2.59-2.55 (m, 2H), 2.27-2.24 (m, 4H), 1.54 (s, 4H), 1.35-1.21 (m, 2H), 1.04-0.98 (m, 2H)

IR (KBr, cm$^{-1}$): 3346, 2928, 2795, 1668, 1600, 1495, 1454, 1284, 1236, 1043

MS (ES): m/z 365.1 (M$^+$+1)

Example 54

Synthesis of (S)-1-(2,2-dioxido-1,3-dihydrobenzo[c]isothiazol-5-yl)-N-(1-phenyl-2-(pyrrolidin-1-yl)ethyl)cyclopropanecarboxamide

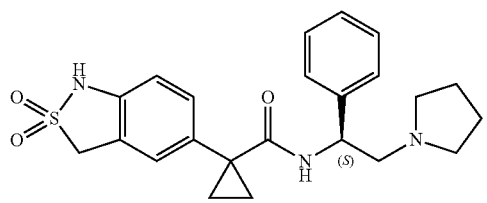

$^1$H NMR (400 MHz, DMSO-d$_6$): δ 10.4 (bs, 1H), 7.30-7.27 (m, 5H), 7.2 (d, J=6.96 Hz, 2H), 7.11 (bs, 1H), 6.82 (d, J=8.0 Hz, 1H), 4.8 (s, 1H), 4.5 (q, J=16.3 Hz, 2H), 2.68 (d, J=11.4 Hz, 2H), 2.36 (s, 4H), 1.61 (s, 4H), 1.30-1.10 (m, 2H), 1.09-0.96 (m, 2H)

IR (KBr, cm$^{-1}$): 3641, 3028, 2960, 2798, 1658, 1492

MS (ES): m/z 426.3 (M$^+$+1)

Example 54

Synthesis of (S)-1-(4-methoxyphenyl)-N-(1-phenyl-2-(pyrrolidin-1-yl)ethyl)cyclopropane carboxamide

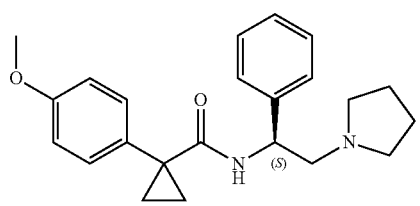

$^1$H NMR (400 MHz, DMSO-d$_6$): δ 7.36-7.16 (m, 7H), 6.95 (q, J=3.0 Hz, 2H), 6.8 (d, J=6.2 Hz, 1H), 4.68 (q, J=6.5 Hz, 1H), 3.75 (s, 3H), 2.56-2.55 (d, J=6.5 Hz, 2H), 2.33-2.20 (m, 4H), 1.53 (bs, 4H), 1.3-1.2 (m, 2H), 1.00-0.89 (m, 2H)

IR (Neat, cm$^{-1}$): 2956, 2927, 2794, 1726, 1666, 1610, 1514, 1494, 1290, 1246, 1029

MS (ES): m/z 365.5 (M$^+$+1)

Example 55

Synthesis of (S)-1-(2-oxo-1,2-dihydroquinolin-6-yl)-N-(1-phenyl-2-(pyrrolidin-1-yl)ethyl)cyclopropane carboxamide

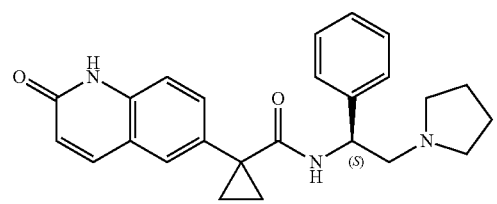

M.P: 171-172° C.

$^1$H NMR (400 MHz, DMSO-d$_6$): δ 11.78 (bs, 1H), 7.91 (d, J=9.8 Hz, 1H), 7.75 (s, 1H), 7.68-7.58 (d, J=8.4 Hz, 1H), 7.39-7.18 (m, 6H), 7.08 (d, J=5.4 Hz, 1H), 6.52 (d, J=9.5 Hz, 1H), 4.71 (d, J=5.4 Hz, 1H), 2.54-2.50 (m, 2H), 2.2 (bs, 4H), 1.41-1.38 (m, 4H), 1.36-1.23 (m, 2H), 1.10-0.97 (m, 2H)

IR (KBr, cm$^{-1}$): 3323, 3163, 2962, 2800, 1664, 1602, 1494, 1429, 1193

MS (ES): m/z 402.3 (M$^+$+1)

Example 56

Synthesis of (S)-1-(4-chlorophenyl)-N-(1-phenyl-2-(pyrrolidin-1-yl)ethyl)cyclopropane carboxamide

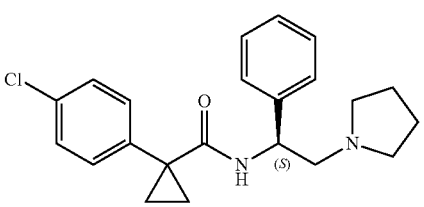

$^1$H NMR (400 MHz, DMSO-d$_6$): δ 7.42 (bs, 4H), 7.30-7.21 (m, 2H), 7.19-7.17 (m, 3H), 7.11 (d, J=6.4 Hz, 1H), 4.75-4.73 (m, 1H), 2.61-2.52 (m, 2H), 2.33-2.26 (m, 4H), 1.56 (bs, 4H), 1.38-1.33 (m, 1H), 1.28-1.23 (m, 1H), 1.07-1.02 (m, 1H), 0.99-0.95 (m, 1H)

IR (Neat, cm$^{-1}$): 3335, 2959, 2926, 2795, 1672, 1493, 1292, 1136

MS (ES): m/z 369.4 (M$^+$+1)

Example 57

Synthesis of (S)-1-(4-chloro-3-(methyl sulfonamido) phenyl)-N-(1-phenyl-2-(pyrrolidin-1-yl)ethyl)cyclopropane carboxamide

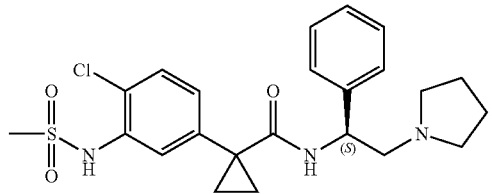

M.P: 280-281° C.
$^1$H NMR (400 MHz, CDCl$_3$): δ 7.76 (bs, 1H), 7.43 (d, J=6.7 Hz, 1H), 7.26-7.19 (m, 7H), 6.80-6.66 (m, 1H), 4.79 (bs, 1H), 3.04 (s, 3H), 2.72 (bs, 1H), 2.58 (bs, 1H), 2.41-2.33 (m, 4H), 1.63-1.41 (m, 4H), 1.26 (bs, 2H), 1.04 (bs, 2H)
IR (Neat, cm$^{-1}$): 3007, 2955, 2922, 2804, 1659, 1571, 1493, 1444, 1329, 1157
MS (ES): m/z 462.5 (M$^+$+1)

Example 58

Synthesis of tert-butyl (S)-1-((S)-2-(1-(3-(methylsulfonamido)phenyl)cyclopropane carboxamido)-2-phenylethyl)pyrrolidin-3-ylcarbamate

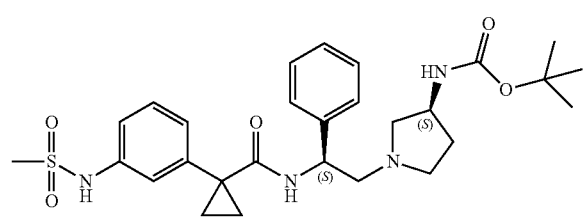

M.P: 66.3-66.5° C.
$^1$H NMR (400 MHz, DMSO-d$_6$): δ 9.70 (s, 1H), 7.40-7.16 (m, 9H), 6.95 (d, J=6.71 Hz, 1H), 6.74 (d, J=6.40 Hz, 1H), 4.76 (q, J=6.91 Hz, 1H), 3.77 (bs, 1H), 2.98 (s, 3H), 2.8-2.6 (m, 1H), 2.64-2.56 (m, 1H), 2.32-2.30 (m, 3H), 2.10 (m, 1H), 1.87-1.82 (m, 2H), 1.45-1.43 (m, 2H), 1.38 (s, 9H), 1.14 (s, 2H)
IR (Neat, cm$^{-1}$): 3429, 2964, 2929, 1710, 1685, 1641, 1550, 1502, 1492, 1462, 1365, 1332, 1155
MS (ES): m/z 543.4 (M$^+$+1)

Example 59

Synthesis of N—((S)-2-((S)-3-(methyl amino)pyrrolidin-1-yl)-1-phenylethyl)-1-(3-(methylsulfonamido)phenyl)cyclopropane carboxamide

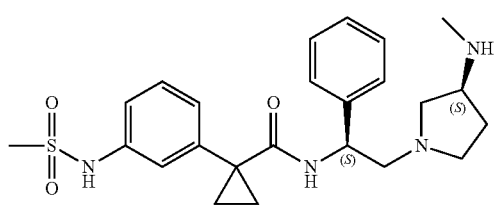

M.P: 80.6-80.8° C.
$^1$H NMR (400 MHz, DMSO-d$_6$): δ 7.36-7.13 (m, 10H), 6.94 (d, J=6.71 Hz, 1H), 4.74 (d, J=6.40 Hz, 1H), 2.97 (s, 3H), 2.70-2.30 (m, 6H), 2.29-2.25 (m, 1H), 2.20 (s, 3H), 2.14-2.11 (m, 1H), 1.80-1.70 (m, 1H), 1.36-1.33 (m, 3H), 1.26-1.24 (m, 2H)
IR (Neat, cm$^{-1}$): 3026, 2953, 2800, 1658, 1585, 1502, 1328, 1219, 1153
MS (ES): m/z 457.5 (M$^+$+1)

Example 60

Synthesis of N—((S)-2-((S)-3-amino pyrrolidin-1-yl)-1-phenyl ethyl)-1-(3-(methyl sulfonamido)phenyl)cyclopropane carboxamide 2,2,2-trifluoroacetate

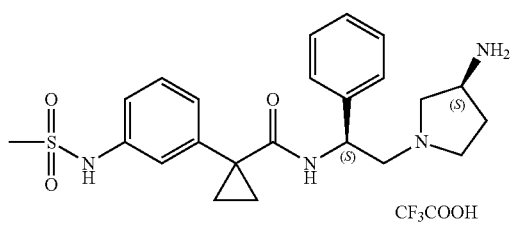

M.P: 119.6-119.8° C.
$^1$H NMR (400 MHz, DMSO-d$_6$): δ 9.76 (s, 1H), 8.2 (bs, 2H), 7.34-7.10 (m, 9H), 5.3 (bs, 1H), 3.60 (bs, 2H), 3.38 (q, J=7.01 Hz, 3H), 2.97 (s, 3H), 2.6-2.3 (m, 3H), 1.97 (bs, 1H), 1.38 (s, 2H), 1.09 (t, J=7.02 Hz, 3H), 0.96 (bs, 1H)
IR (Neat, cm$^{-1}$): 3410, 2958, 2926, 2854, 1726, 1674, 1639, 1504, 1325, 1288, 1201, 1151, 1072
MS (ES): m/z 443.3 (M$^+$+1)

Example 61

Synthesis of 1-(2,2-dioxo-2,3-dihydro-2-benzo[1,2,3]oxathiazol 5-yl)-cyclopropane carboxylic acid (1-phenyl-2-pyrrolidin-1-yl-ethyl)-amide

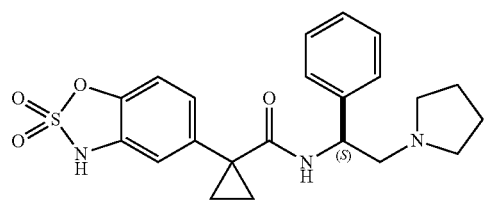

M.P: 239-241° C.
$^1$H NMR (400 MHz, DMSO-d$_6$): δ 9.25 (bs, 1H), 7.38-7.26 (m, 6H), 6.67 (d, J=7.6 Hz, 1H), 6.49 (s, 1H), 6.34 (dd, J=1.8 & 7.6 Hz, 1H), 5.30 (bs, 1H), 3.63-3.61 (m, 1H), 3.48-3.42 (m, 3H), 3.09-2.98 (m, 2H), 1.97-1.83 (m, 4H), 1.29-1.20 (m, 2H), 1.16-1.00 (m, 1H), 0.99-0.86 (m, 1H)
IR (Neat, cm$^{-1}$): 3387, 3360, 3072, 2717, 2632, 2519, 1642, 1598, 1527, 1473, 1429, 1286, 1151
MS (ES): m/z 428.3 (M$^+$+1)

Example 62

Synthesis of 1-(3-dimethylsulfamoyl-phenyl)-cyclopropane carboxylic acid (1-phenyl-2-pyrrolidin-1-yl-ethyl)-amide

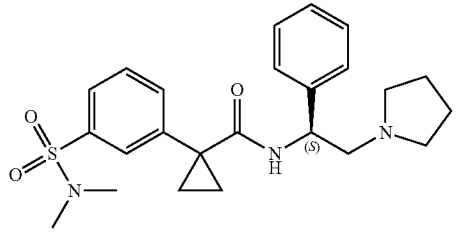

$^1$H NMR (400 MHz, DMSO-d$_6$): δ 7.75 (d, J=1.5 Hz, 1H), 7.74-7.63 (m, 3H), 7.29-7.19 (m, 6H), 4.83-4.78 (q, J$_1$=6.8 Hz, J$_2$=6.7 Hz, 1H), 2.62-2.60 (m, 2H), 2.58 (s, 6H), 2.29 (d, J=8.5 Hz, 4H), 1.55 (s, 4H), 1.41-1.39 (m, 2H), 1.14-1.11 (bs, 2H)

IR (Neat, cm$^{-1}$): 3315, 1649, 1502, 1334, 1165

MS (ES): m/z 442.4 (M$^+$+1)

Example 63

Synthesis of 1-(4-sulfamoyl-phenyl)-cyclopropane carboxylic acid (1-phenyl-2-pyrrolidin-1-yl-ethyl)-amide

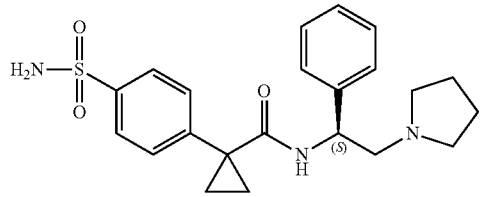

$^1$H NMR (400 MHz, DMSO-d$_6$): δ 7.78 (d, J=8.5 Hz, 2H), 7.56 (d, J=8.2 Hz, 2H), 7.38 (s, 2H), 7.29-7.20 (m, 6H), 4.83-4.80 (q, J=5.18, J$_2$=3.35 Hz, 1H), 2.70-2.67 (t, J=10.17 Hz, 2H), 2.36-2.31 (m, 4H), 1.67 (bs, 4H), 1.39-1.37 (m, 2H), 1.24-1.03 (m, 2H)

IR (Neat, cm$^{-1}$): 3348, 2962, 2800, 1668, 1494, 1344, 1165

MS (ES): m/z 414.3 (M$^+$+1)

Example 64

Synthesis of 1-(3-acetyl-4-hydroxyphenyl)-cyclopropane carboxylic acid (1-phenyl-2-pyrrolidin-1-yl-ethyl)-amide

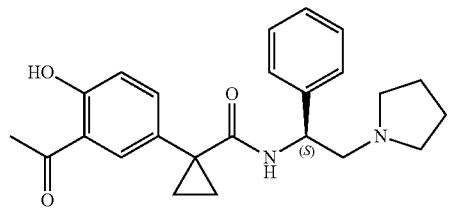

M.P: 101.8-102.2° C.

$^1$H NMR (400 MHz, DMSO-d$_6$): δ 11.8 (s, 1H), 7.8 (d, J=1.8 Hz, 1H), 7.57-7.54 (m, 1H), 7.79-7.29 (m, 4H), 7.0 (d, J=6.4 Hz, 1H), 6.96 (d, J=8.5 Hz, 1H), 4.75 (s, 1H), 2.65 (s, 3H), 2.64 (s, 1H), 2.28 (s, 4H), 1.53 (s, 4H), 1.36-1.23 (m, 4H), 1.07-1.04 (m, 2H)

IR (Neat, cm$^{-1}$): 3410, 2964, 2785, 1659, 1614, 1514

MS (ES): m/z 393.5 (M$^+$+1)

Example 65

Synthesis of 1-(2-oxo-2,3-dihydro-benzooxazol-5-yl)-cyclopropane carboxylic acid (1-phenyl-2-pyrrolidin-1-yl-ethyl)-amide

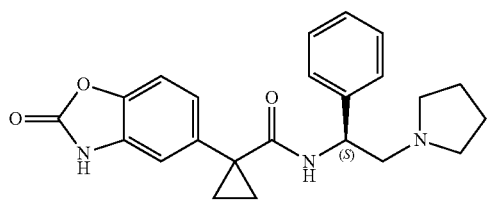

M.P: 142-144° C.

$^1$H NMR (400 MHz, DMSO-d$_6$): δ 11.60 (bs, 1H), 7.30-7.08 (m, 8H), 6.97 (d, J=6.7 Hz, 1H), 4.72 (q, J=6.4 Hz, 1H), 2.58 (bs, 2H), 2.56-2.33 (m, 4H), 1.51 (bs, 4H), 1.38-1.35 (m, 1H), 1.34-1.24 (m, 1H), 1.06-0.96 (m, 2H)

IR (Neat, cm$^{-1}$): 3314, 2775, 1774, 1614, 1518, 1259

MS (ES): m/z 392.3 (M$^+$+1)

Example 66

Synthesis of 1-(3-methanesulfonylamino-phenyl)-cyclopropane carboxylic acid (1-benzyl-2-pyrrolidin-1-yl-ethyl)-amide

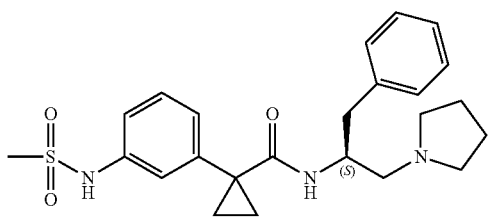

$^1$H NMR (400 MHz, DMSO-d$_6$): δ 9.72 (bs, 1H), 7.3-6.97 (m, 9H), 6.35 (d, J=7.0 MHz, 1H), 4.0 (d, J=6.4 MHz, 1H), 2.95 (s, 3H), 2.76-2.65 (m, 2H), 2.4 (bs, 6H), 1.64 (bs, 4H), 1.2 (q, J=6.7 MHz, 2H), 0.89 (d, J=2.7 MHz, 2H)

IR (Neat, cm$^{-1}$): 3408, 2958, 2793, 1639, 1604, 1585, 1512, 1400, 1329, 1153

MS (ES): m/z 442.4 (M$^+$+1)

Example 67

Synthesis of 1-(3-methanesulfonylamino-phenyl)-cyclopropane carboxylic acid (1-pyridin-3-yl-2-pyrrolidin-1-yl-ethyl)-amide

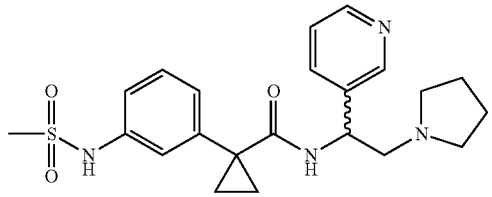 [SMILES: CS(=O)(=O)Nc1cccc(C2(C(=O)NC(CN3CCCC3)c3cccnc3)CC2)c1]

$^1$H NMR (400 MHz, DMSO-d$_6$): δ 9.76 (s, 1H), 8.43-8.40 (m, 2H), 7.6 (d, J=7.9 MHz, 1H), 7.36-7.1 (m, 6H), 4.8 (d, J=6.7 MHz, 1H), 2.98 (s, 3H), 2.62 (bs, 2H), 2.29 (bs, 4H), 1.56 (bs, 4H), 1.35-1.22 (m, 2H), 0.98 (d, J=3.6 MHz, 2H)

IR (Neat, cm$^{-1}$): 2972, 2974, 1662, 1604, 1587, 1500, 1406, 1329, 1153

MS (ES): m/z 429.9 (M$^+$+1)

Example 68

Synthesis of (S)—N-(1-cyclohexyl-2-(pyrrolidin-1-yl)ethyl)-1-(3-(methylsulfonamido)phenyl)cyclopropanecarboxamide

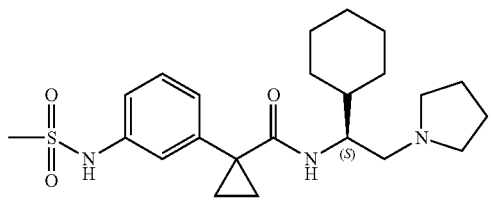

M.pt: 201-202° C.

$^1$H NMR (400 MHz, DMSO-d$_6$): δ 9.8 (s, 1H), 9.77 (s, 1H), 7.34-7.28 (m, 2H), 7.17-7.12 (m, 2H), 6.7 (d, J=9.1 MHz, 1H), 3.94 (bs, 1H), 3.5-3.37 (m, 2H), 3.2 (d, J=5.5 MHz, 2H), 2.99 (s, 3H), 2.92 (d, J=9.5 MHz, 2H), 1.94 (m, 4H), 1.7-1.3 (m, 8H), 1.17-1.0 (m, 4H), 0.93-0.7 (m, 3H)

IR (Neat, cm$^{-1}$): 3414, 3012, 2929, 2848, 2779, 2492, 1654, 1606, 1587, 1517, 1477, 1462, 1323, 1203, 1147

MS (ES): m/z 434.5 (M$^+$+1)

Example 69

Synthesis of (S)—N-(4-methyl-1-(pyrrolidin-1-yl)pentan-2-yl)-1-(3-(methylsulfonamido)phenyl)cyclopropanecarboxamide

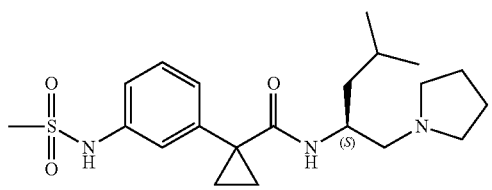

$^1$H NMR (400 MHz, CDCl$_3$+D$_2$O): δ 7.36-7.31 (m, 2H), 7.22-7.20 (m, 2H), 3.95 (brs, 1H), 3.03 (s, 3H), 2.43-2.37 (m, 4H), 1.68 (bs, 4H), 1.59-1.58 (m, 2H), 1.55-1.50 (m, 1H), 1.26 (t, J=7.3 Hz, 4H), 1.02-1.01 (m, 2H), 0.88-0.86 (m, 6H)

IR (Neat, cm$^{-1}$): 3408, 2789, 1753, 1697, 1653, 1641, 1512

MS (ES): m/z 408.4 (M$^+$+1)

Example 70

Synthesis of (R)—N-(1-(3-(benzyloxy)phenyl)-2-(pyrrolidin-1-yl)ethyl)-1-(3-(methyl sulfonamido)phenyl)cyclopropanecarboxamide

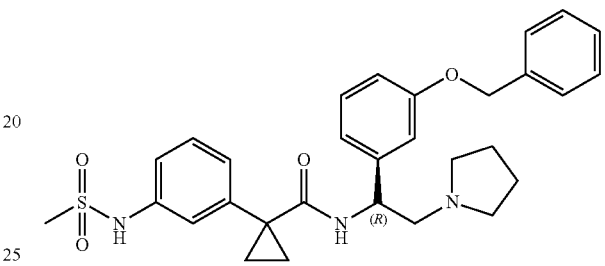

M.P: 70-72° C.

$^1$H NMR (400 MHz, DMSO-d$_6$): δ 9.76 (s, 1H), 7.45-7.32 (m, 7H), 7.25 (s, 1H), 7.21-7.14 (m, 2H), 6.96 (bs, 1H), 6.85 (s, 2H), 6.78 (d, J=7.7 Hz, 1H), 5.06 (s, 2H), 4.72 (bs, 1H), 2.96 (s, 3H), 2.55-2.45 (m, 2H), 2.24 (bs, 4H), 1.54 (bs, 4H), 1.35-1.24 (m, 2H), 0.99 (s, 2H)

IR (KBr, cm$^{-1}$): 2962, 2798, 1643, 1604, 1587, 1502, 1328, 1155

MS (ES): m/z 534.4 (M$^+$+1)

Example 71

Synthesis of (R)—N-(1-(3-hydroxyphenyl)-2-(pyrrolidin-1-yl)ethyl)-1-(3-(methylsulfonamido)phenyl)cyclopropanecarboxamide

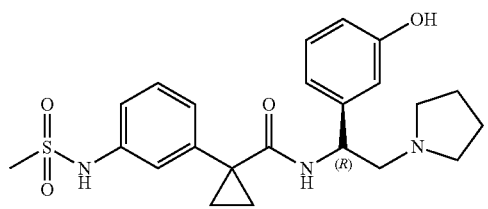

M.P: 103-105° C.

$^1$H NMR (400 MHz, DMSO-d$_6$): δ 9.77 (bs, 1H), 9.28 (s, 1H), 7.35 (t, J=7.7 Hz, 1H), 7.24 (s, 1H), 7.18-7.11 (m, 2H), 7.06 (t, J=8.0 Hz, 1H), 6.91 (bs, 1H), 6.61-6.58 (m, 3H), 4.65 (bs, 1H), 2.98 (s, 3H), 2.67-2.50 (m, 2H), 2.33-2.26 (m, 4H), 1.55 (bs, 4H), 1.36-1.24 (m, 2H), 0.99 (s, 2H)

IR (KBr, cm$^{-1}$): 3215, 2962, 2927, 2804, 2216, 1643, 1589, 1506, 1390, 1327, 1309, 1153

MS (ES): m/z 444.3 (M$^+$+1)

Example 72

Synthesis of (R)—N-(1-(3-methoxyphenyl)-2-(pyrrolidin-1-yl)ethyl)-1-(3-(methylsulfonamido)phenyl)cyclopropanecarboxamide

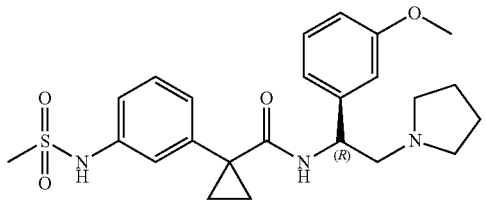

¹H NMR (400 MHz, DMSO-d₆): δ 9.76 (bs, 1H), 7.35 (t, J=7.9 Hz, 1H), 7.25 (s, 1H), 7.21-7.15 (m, 3H), 6.99 (bs, 1H), 6.78-6.76 (m, 3H), 4.74 (bs, 1H), 3.72 (s, 3H), 2.98 (s, 3H), 2.67-2.60 (m, 2H), 2.28 (bs, 4H), 1.56 (bs, 4H), 1.36-1.24 (m, 2H), 0.99 (s, 2H)

IR (Neat, cm⁻¹): 1643, 1604, 1587, 1500, 1400, 1328, 1155, 1043

MS (ES): m/z 458.3 (M⁺+1)

Example 73

Synthesis of 1-(3-methanesulfonylamino-4-methoxyphenyl)-cyclopropane carboxylic acid (1-phenyl-2-pyrrolidin-1-yl-ethyl)-amide

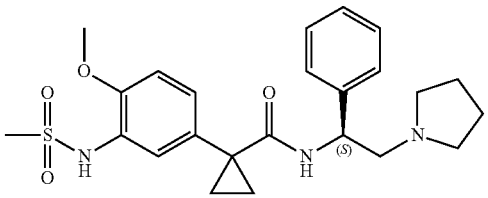

M.P: 103-105° C.

¹H NMR (400 MHz, DMSO-d₆): δ 8.96 (bs, 1H), 7.34 (s, 1H), 7.30-7.19 (m, 6H), 7.08 (d, J=8.21 Hz, 1H), 6.88 (d, J=6.1 Hz, 1H), 4.72 (d, J=5.2 Hz, 1H), 3.83 (s, 3H), 2.95 (s, 3H), 2.57 (bs, 2H), 2.25 (bs, 4H), 1.53 (bs, 4H), 1.33-1.24 (m, 2H), 0.96 (bs, 2H)

IR (Neat, cm⁻¹): Not available

MS (ES): m/z 458.4 (M⁺+1)

Example 74

Synthesis of 1-(3-methyl-benzo[d]isoxazol-5-yl)-cyclopropane carboxylic acid (1-phenyl-2-pyrrolidin-1-yl-ethyl)-amide

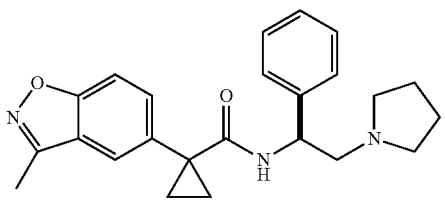 [SMILES: Cc1noc2ccc(C3(C(=O)N[C@H](CN4CCCC4)c4ccccc4)CC3)cc12]

M.P: 158.5-158.8° C.

¹H NMR (400 MHz, DMSO-d₆): δ 7.88 (s, 1H), 7.71-7.66 (m, 2H), 7.29-7.25 (m, 2H), 7.20-7.17 (m, 3H) 7.0 (d, J=6.4 Hz, 1H), 4.76-4.74 (m, 1H), 2.56 (s, 3H), 2.55-2.53 (bs, 2H), 2.23-2.21 (m, 4H), 1.44-1.40 (m, 5H), 1.35-1.13 (m, 1H), 1.12-1.08 (m, 1H), 1.07-1.04 (m, 1H)

IR (Neat, cm⁻¹): 3348, 2963, 2928, 2874, 2795, 1664, 1492

MS (ES): m/z 390.4 (M⁺+1)

Example 75

Synthesis of 1-(6-ethoxy-pyridin-2-yl)-cyclopropane carboxylic acid (1-phenyl-2-pyrrolidin-1-yl-ethyl)-amide

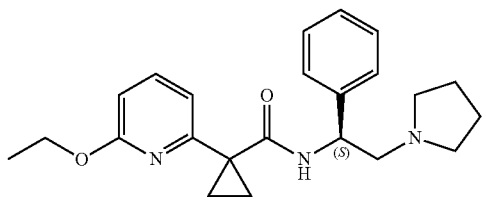

¹H NMR (400 MHz, DMSO-d₆): δ 8.21 (d, J=7.6 Hz, 1H), 7.60 (t, J=7.7 Hz, 1H), 7.34-7.29 (m, 4H), 7.24-7.19 (m, 1H), 7.03 (d, J=7.3 Hz, 1H), 6.64 (d, J=8.3 Hz, 1H), 4.98-4.93 (m, 1H), 4.26 (q, J=7.0 Hz, 2H), 2.81-2.76 (m, 1H), 2.44-2.33 (m, 5H), 1.63 (bs, 4H), 1.30 (t, J=7.0 Hz, 3H), 1.27-1.20 (m, 4H)

IR (Neat, cm⁻¹): 2974, 2792, 1658, 1593, 1571, 1502, 1450, 1332, 1276, 1253

MS (ES): m/z 380.5 (M⁺+1)

Example 76

Synthesis of 1-(4-methanesulfonylamino-3-methyl-phenyl)-cyclopropanecarboxylic acid (1-phenyl-2-pyrrolidin-1-yl-ethyl)-amide

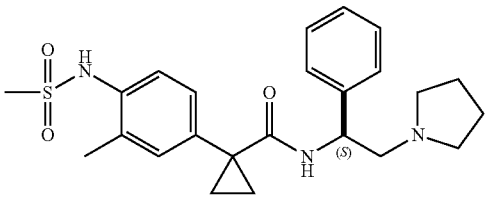

M.P: 92-94° C.

¹H NMR (400 MHz, DMSO-d₆): δ 9.09 (bs, 1H), 7.30-7.26 (m, 4H), 7.24-7.19 (m, 4H), 7.07 (d, J=6.4 Hz, 1H), 4.76-4.71 (m, 1H), 2.97 (s, 3H), 2.53 (bs, 2H), 2.31 (s, 3H), 2.26 (bs, 4H), 1.56 (bs, 4H), 1.35-1.30 (m, 1H), 1.26-1.21 (m, 1H), 1.06-1.01 (m, 2H)

IR (Neat, cm⁻¹): 2924, 1647, 1502, 1331, 1155

MS (ES): m/z 442.24 (M⁺+1)

Example 77

Synthesis of 1-(3-methanesulfonylamino-4-methyl-phenyl)-cyclopropane carboxylic acid (1-phenyl-2-pyrrolidin-1-yl-ethyl)-amide

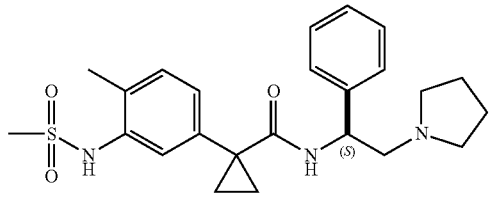

M.P: 92-94° C.
$^1$H NMR (400 MHz, DMSO-$d_6$): δ 9.11 (bs, 1H), 7.32-7.26 (m, 4H), 7.25-7.19 (m, 4H), 6.98 (d, J=6.7 Hz, 1H), 4.76-4.73 (m, 1H), 2.96 (s, 3H), 2.62-2.57 (m, 2H), 2.31 (s, 3H), 2.29-2.24 (m, 4H), 1.52 (bs, 4H), 1.35-1.25 (m, 2H), 1.05-1.00 (m, 2H)
IR (Neat, cm$^{-1}$): 2959, 2928, 2799, 1653, 1502, 1327, 1155
MS (ES): m/z 442.24 (M$^+$+1)

Example 78

Synthesis of 1-(3-formylamino-4-hydroxy-phenyl)-cyclopropanecarboxylic acid (1-phenyl-2-pyrrolidin-1-yl-ethyl)-amide

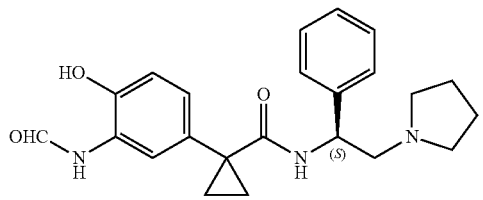

M.P: 175-177° C.
$^1$H NMR (400 MHz, DMSO-$d_6$): δ 10.10 (s, 1H), 9.61 (s, 1H), 8.30 (s, 1H), 8.20 (d, J=1.9 Hz, 1H), 7.29-7.25 (m, 2H), 7.20-7.16 (m, 3H), 6.99-6.97 (m, 1H), 6.88-6.85 (m, 2H), 4.67 (bs, 1H), 2.55-2.50 (bs, 2H), 2.33-2.11 (bs, 4H), 1.50 (bs, 4H), 1.32-1.28 (m, 1H), 1.23-1.20 (m, 1H), 0.96-0.92 (m, 2H)
IR (Neat, cm$^{-1}$): 3269, 2963, 2808, 1663, 1537, 1503, 1433, 1375
MS (ES): m/z 394.4 (M$^+$+1)

Example 79

Synthesis of 1-(4-fluoro-3-methanesulfonylamino-phenyl)-cyclopropane carboxylic acid (1-phenyl-2-pyrrolidin-1-yl-ethyl)-amide

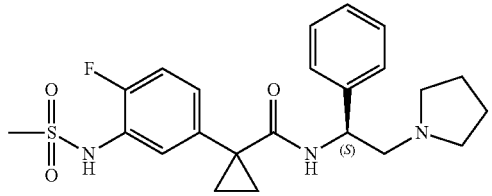

M.P: 67-69° C.
$^1$H NMR (400 MHz, DMSO-$d_6$): δ 9.70 (bs, 1H), 7.43-7.41 (m, 1H), 7.31-7.26 (m, 4H), 7.22-7.17 (m, 3H), 7.05 (d, J=6.6 Hz, 1H), 4.80-4.75 (m, 1H), 3.02 (s, 3H), 2.66-2.54 (m, 2H), 2.30 (bs, 4H), 1.56 (bs, 4H), 1.36-1.24 (m, 2H), 1.04-0.97 (m, 2H)
IR (Neat, cm$^{-1}$): 1651, 1512, 1402, 1333, 1157
MS (ES): m/z 446.3 (M$^+$+1)

Example 80

Synthesis of 1-(2,2-Dioxo-2,3-dihydro-1H-2-benzo[c]isothiazol-6-yl)-cyclopropane carboxylic acid (1-phenyl-2-pyrrolidin-1-yl-ethyl)-amide

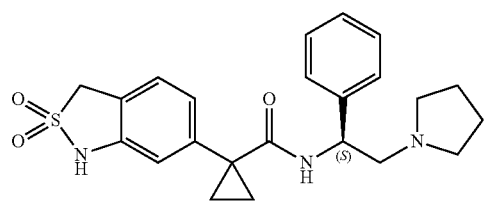

M.P: 138-140° C.
$^1$H NMR (400 MHz, DMSO-$d_6$): δ 10.45 (bs, 1H), 7.30-7.20 (m, 5H), 7.18 (s, 1H), 7.16 (d, J=6.6 Hz, 1H), 7.01 (dd, $J_1$=1.5 Hz, $J_2$=7.7 Hz, 1H), 6.79 (s, 1H), 4.82-4.77 (m, 1H), 4.5 (s, 2H), 2.75-2.62 (m, 2H), 2.40 (bs, 4H), 1.60 (s, 4H), 1.35-1.32 (m, 2H), 1.31-1.27 (m, 2H)
IR (Neat, cm$^{-1}$): 2958, 2927, 2856, 1728, 1658, 1500, 1288, 1265, 1138
MS (ES): m/z 426 (M$^+$+1)

Example 81

Synthesis of 1-Benzooxazol-6-yl-cyclopropanecarboxylic acid (1-phenyl-2-pyrrolidin-1-yl-ethyl)-amide

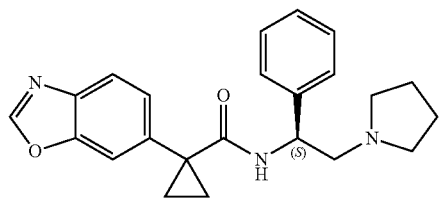

$^1$H NMR (400 MHz, CDCl$_3$): δ 8.14 (s, 1H), 7.80 (d, J=8.0 Hz, 1H), 7.70 (s, 1H), 7.53 (d, J=8.0 Hz, 1H), 7.20-7.13 (m, 5H), 6.57 (bs, 1H), 4.70 (bs, 1H), 2.57-2.51 (m, 2H), 2.49 (bs, 2H), 2.28 (bs, 2H), 1.25 (bs, 4H), 1.20-1.16 (m, 2H), 0.96-0.88 (m, 2H)
MS (ES): m/z 376.2 (M$^+$+1)

Example 82

Synthesis of 3-[1-(1-phenyl-2-pyrrolidin-1-yl-ethyl-carbamoyl)-cyclopropyl]-benzamide

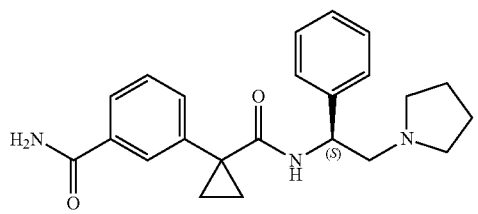

M.P: 120-121° C.
¹H NMR (400 MHz, DMSO-d$_6$): δ 8.01 (s, 1H), 7.92 (s, 1H), 7.83 (d, J=7.33 Hz, 1H), 7.56 (d, J=7.3 Hz, 1H), 7.47-7.43 (m, 3H), 7.38 (s, 1H), 7.28-7.21 (m, 3H), 7.08 (bs, 1H), 4.78 (bs, 1H), 2.67 (s, 2H), 2.32-2.11 (m, 4H), 1.55-1.37 (m, 6H), 1.10-1.09 (m, 2H)
IR (Neat, cm⁻¹): 2794, 1662, 1587, 1500, 1328, 1153
MS (ES): m/z 378.2 (M⁺+1)

Example 83

Synthesis of 1-(2,4-Difluoro-5-methanesulfonylamino-phenyl)-cyclopropane carboxylic acid (1-phenyl-2-pyrrolidin-1-yl-ethyl)-amide

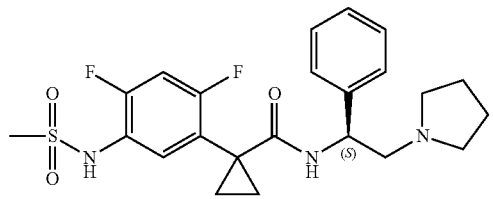

M.P: 81.2-81.4° C.
¹H NMR (400 MHz, DMSO-d$_6$): δ 9.59 (bs, 1H), 7.45-7.39 (m, 2H), 7.30-7.26 (m, 2H), 7.22-7.17 (m, 3H), 7.11 (d, J=6.6 Hz, 1H), 4.81-4.77 (m, 1H), 3.01 (s, 3H), 2.67-2.54 (m, 2H), 2.32 (bs, 4H), 1.58 (bs, 4H), 1.44-1.40 (m, 1H), 1.37-1.33 (m, 1H), 1.01 (d, J=3.3 Hz, 2H)
IR (Neat, cm⁻¹): 3134, 2961, 2801, 1661, 1607, 1506, 1447, 1333
MS (ES): m/z 464.4 (M⁺+1)

Example 84

Synthesis of 1-[4-Hydroxy-3-(1-hydroxyimino-ethyl)-phenyl]-cyclopropane carboxylic acid (1-phenyl-2-pyrrolidin-1-yl-ethyl)-amide

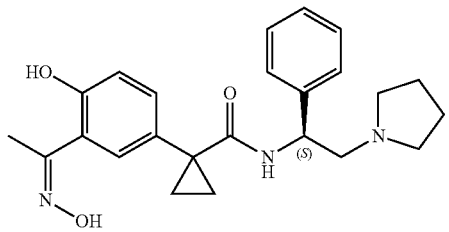

M.P: 158.5-158.8° C.
¹H NMR (400 MHz, DMSO-d$_6$): δ 11.58-11.57 (bs, 2H), 7.47 (d, J=2.2 Hz, 1H), 7.29-7.20 (m, 3H), 7.19-7.17 (m, 3H), 6.95 (d, J=6.5 Hz, 1H), 6.89-6.87 (m, 1H), 4.71 (q, J=6.4 Hz, 1H), 2.56 (bs, 2H), 2.32 (s, 3H), 2.27-2.23 (m, 4H), 1.49 (bs, 4H), 1.39-1.30 (m, 1H), 1.26-1.22 (m, 1H), 1.03-1.00 (bs, 2H)
IR (Neat, cm⁻¹): 3165, 3065, 2964, 2930, 2806, 1639, 1506
MS (ES): 408.4 (M⁺+1)

Example 85

Synthesis of 1-(2-Oxo-2,3-dihydro-1H-benzoimidazol-5-yl)-cyclopropane carboxylic acid (1-phenyl-2-pyrrolidin-1-yl-ethyl)-amide

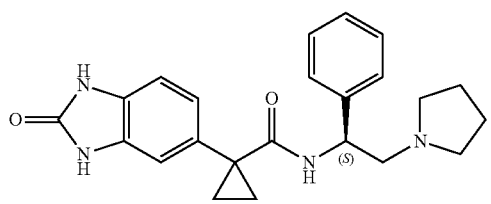

M.P: 207-209° C.
¹H NMR (400 MHz, DMSO-d$_6$): δ 10.64 (d, J=7.4 Hz, 2H), 7.29-7.26 (m, 2H), 7.20-7.15 (m, 3H), 6.99-6.93 (m, 1H), 6.91-6.87 (m, 3H), 4.67 (bs, 1H), 2.50 (bs, 2H), 2.25-2.18 (bs, 4H), 1.46-1.40 (m, 4H), 1.34-1.31 (bs, 1H), 1.30-1.23 (bs, 1H), 1.08-0.96 (m, 2H)
IR (KBr, cm⁻¹): 3092, 3030, 2966, 2812, 1703, 1670, 1655, 1500, 1475

Example 86

Synthesis of 1-(1-Methyl-1H-benzotriazol-5-yl)cyclopropane carboxylic acid (1-phenyl-2-pyrrolidin-1-yl-ethyl)-amide

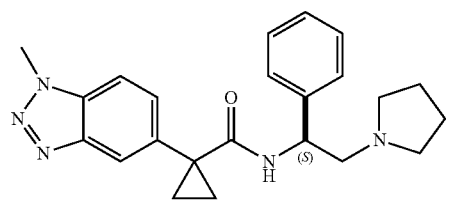

M.P: 78-80° C.
¹H NMR (400 MHz, ¹H DMSO-d$_6$): δ 8.04 (s, 1H), 7.86 (d, J=8.8 Hz, 1H), 7.59 (d, J=8.4 Hz, 1H), 7.29-7.25 (m, 2H), 7.21-7.17 (m, 3H), 7.06 (d, J=6.6 Hz, 1H), 4.78 (bs, 1H), 4.31 (s, 3H), 2.67-2.45 (m, 2H), 2.24-2.20 (m, 4H), 1.43 (bs, 4H), 1.36-1.33 (m, 2H), 1.18-1.09 (m, 2H)
IR (KBr, cm⁻¹): 3008, 2798, 2781, 1755, 1641, 1587, 1502, 1192
MS (ES): m/z 390.4 (M⁺+1)

Example 87

Synthesis of 1-(2-Oxo-1,2-dihydro-quinolin-7-yl)-cyclopropane carboxylic acid (1-phenyl-2-pyrrolidin-1-yl-ethyl)-amide

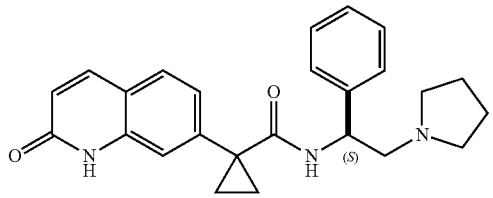

M.P: 101-103° C.
$^1$H NMR (400 MHz, DMSO-d$_6$): δ 11.75 (s, 1H), 7.92 (d, J=9.5 Hz, 1H), 7.66 (d, J=7.7 Hz, 1H), 7.32-7.19 (m, 7H), 7.09 (bs, 1H), 6.49 (d, J=9.5 Hz, 1H), 4.75 (bs, 1H), 2.67-2.42 (m, 2H), 2.23 (bs, 4H), 1.44 (bs, 4H), 1.31-1.24 (m, 2H), 1.09-1.04 (m, 2H)
IR (KBr, cm$^{-1}$): 3415, 2254, 2127, 1651, 1504, 1219, 1047, 1024
MS (ES): m/z 402.3 (M$^+$+1)

Example 88

Synthesis of {3-[1-(1-Phenyl-2-pyrrolidin-1-yl-ethyl-carbamoyl)-cyclopropyl]-phenoxy}-acetic acid

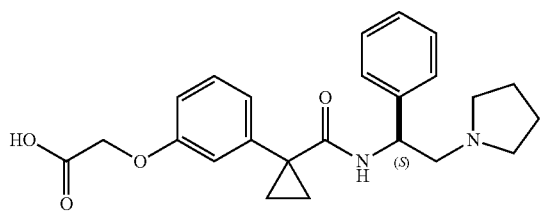

M.P: 124-125° C.
$^1$H NMR (400 MHz, CDCl$_3$): δ 7.30-7.20 (m, 4H), 7.14-7.12 (m, 2H), 6.87-6.82 (m, 3H), 5.02 (bs, 1H), 4.54-4.46 (m, 2H), 3.23-3.17 (m, 1H), 2.88-2.86 (m, 5H), 1.80 (bs, 4H), 1.33-1.30 (m, 1H), 1.24 (bs, 2H), 1.20-1.10 (m, 1H)
IR (KBr, cm$^{-1}$): 3375, 2924, 1653, 1605, 1497, 1215
MS (ES): 409.0 (M$^+$+1)

Example 89

Synthesis of 4-[1-(1-Phenyl-2-pyrrolidin-1-yl-ethyl-carbamoyl)-cyclopropyl]-benzamide

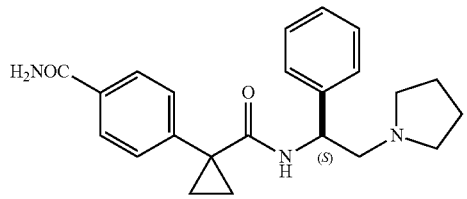

M.P: 201-201° C.
$^1$H NMR (400 MHz, DMSO-d$_6$): δ 7.97 (s, 1H), 7.88 (d, J=8.42 Hz, 2H), 7.46 (d, J=8.42 Hz, 2H), 7.29 (d, J=7.69 Hz, 1H), 7.20 (d, J=7.32 Hz, 2H), 7.17-7.16 (m, 4H), 4.77 (d, J=5.8 Hz, 1H), 2.61 (d, J=8.42 Hz, 2H), 2.30-2.26 (m, 4H), 1.55 (s, 4H), 1.37-1.35 (t, J=3.29 Hz, 2H), 1.03-1.01 (t, J=3.10 Hz, 2H)
IR (KBr, cm$^{-1}$): 3379, 3329, 2962, 1643, 1523, 1413, 1130
MS (ES): 378.3 (M$^+$+1)

Example 90

Synthesis of 1-(2,2-Dioxo-1,2-dihydro-216-benzo[c][1,2]thiazin-7-yl)-cyclopropane carboxylic acid (1-phenyl-2-pyrrolidin-1-yl-ethyl)-amide

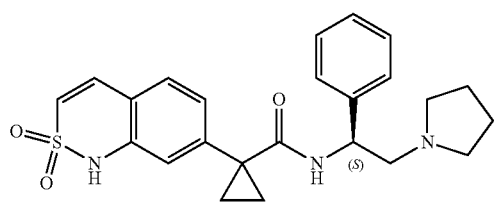

M.P: 148-150° C.
(400 MHz, DMSO-d$_6$): δ 11.5-10.5 (bs, 1H), 7.44 (d, J=8.0 Hz, 1H), 7.38 (d, J=10.3 Hz, 1H), 7.35-7.23 (m, 6H), 6.98 (d, J=7.7 Hz, 1H), 6.95-6.87 (m, 2H), 4.94 (s, 1H), 2.93-2.85 (m, 2H), 2.61 (bs, 4H), 1.66 (bs, 4H), 1.29-1.14 (m, 2H), 1.09-1.03 (m, 2H)
IR (KBr, cm$^{-1}$): 3400, 3030, 2922, 2852, 1658, 1606, 1508, 1448, 1357, 1126
MS (ES): 438 (M$^+$+1)

Example 91

Synthesis of 1-(1H-Benzoimidazol-5-yl)-cyclopropanecarboxylic acid (1-phenyl-2-pyrrolidin-1-yl-ethyl)-amide

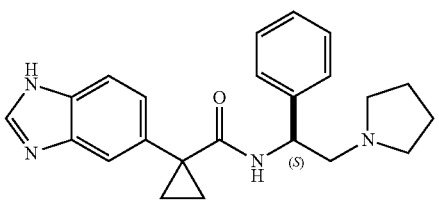

M.P: 127-129° C.
$^1$H NMR (400 MHz, DMSO-d$_6$): δ 12.46 (s, 1H), 8.23 (s, 1H), 7.69-7.63 (m, 1H), 7.59-7.52 (m, 1H), 7.30-7.25 (m, 1H), 7.20-7.15 (m, 5H), 6.86 (s, 1H), 4.68 (s, 1H), 2.50 (bs, 2H), 2.25-2.15 (bs, 4H), 1.37-1.24 (m, 6H), 1.11-1.02 (m, 2H)
IR (KBr, cm$^{-1}$): 3410, 3183, 2965, 2801, 1649, 1499, 1448, 1408
MS (ES): m/z 375.2 (M$^+$+1)

Example 92

Synthesis of 1-(4-Fluoro-3-methanesulfonylamino-phenyl)-cyclopropane carboxylic acid (1-phenyl-2-pyrrolidin-1-yl-ethyl)-amide.hydrochloride

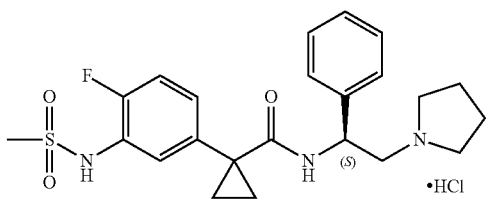

M.P: 130° C.
$^1$H NMR (400 MHz, DMSO-d$_6$): δ 9.90 (bs, 1H), 9.65 (s, 1H), 7.66 (d, J=8.8 Hz, 1H), 7.44 (d, J=7.3 Hz, 1H), 7.37-7.34 (m, 2H), 7.30-7.25 (m, 5H), 5.33-5.28 (m, 1H), 3.57-3.37 (m, 2H), 3.10-3.05 (m, 2H), 3.04 (s, 3H), 3.00-2.96 (m, 2H), 1.97-1.89 (m, 4H), 1.42 (s, 2H), 1.11-1.07 (m, 2H)
IR (Neat, cm$^{-1}$): 3025, 2691, 2609, 2491, 1659, 1512, 1327, 1155
MS (ES): m/z 446.3 (M$^+$+1)

Example 93

Synthesis of 1-(4-Fluoro-3-methanesulfonylamino-phenyl)-cyclopropanecarboxylic acid [2-(3-hydroxy-pyrrolidin-1-yl)-1-phenyl-ethyl]-amide

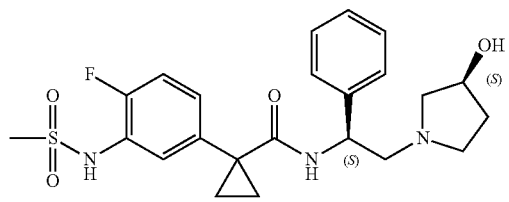

$^1$H NMR (400 MHz, DMSO-d$_6$): δ 9.64 (bs, 1H), 7.40 (d, J=7.7 Hz, 1H), 7.29-7.26 (m, 4H), 7.22-7.18 (m, 3H), 7.07 (d, J=7.4 Hz, 1H), 4.81-4.76 (m, 1H), 4.64 (bs, 1H), 4.09 (bs, 1H), 3.03 (s, 3H), 2.68-2.54 (m, 3H), 2.51-2.39 (m, 1H), 2.35-2.30 (m, 1H), 2.19-2.16 (m, 1H), 1.87-1.78 (m, 1H), 1.47-1.40 (m, 1H), 1.36-1.33 (m, 1H), 1.30-1.26 (m, 1H), 1.03-0.97 (m, 2H)
IR (Neat, cm$^{-1}$): 2922, 2801, 1649, 1512, 1331, 1155
MS (ES): m/z 462.2 (M$^+$+1)

Example 94

Synthesis of {4-[1-(1-Phenyl-2-pyrrolidin-1-yl-ethyl-carbamoyl)-cyclopropyl]-phenoxy}-acetic acid

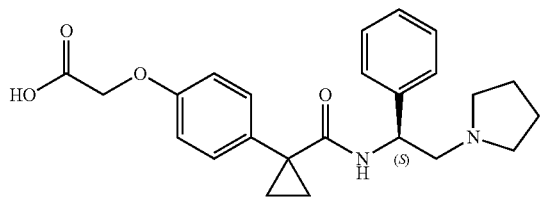

M.P: 94-95° C.
$^1$H NMR (400 MHz, DMSO-d$_6$): δ 13.2-12.4 (bs, 1H), 7.33-7.26 (m, 4H), 7.21-7.17 (m, 3H), 6.99 (d, J=6.6 Hz, 1H), 6.90 (d, J=8.8 Hz, 2H), 4.76-4.74 (m, 1H), 4.60 (s, 2H), 2.78-2.65 (m, 2H), 2.42-2.33 (bs, 4H), 1.58 (bs, 4H), 1.32-1.30 (m, 1H), 1.24-1.21 (m, 1H), 0.98-0.92 (m, 2H)
IR (Neat, cm$^{-1}$): 3373, 2683, 2480, 1645, 1609, 1493, 1223
MS (ES): 409.0 (M$^+$+1)

Example 95

Synthesis of (S)-1-(6-(methylsulfonamido)pyridin-3-yl)-N-(1-phenyl-2-(pyrrolidin-1-yl)ethyl)cyclopropanecarboxamide

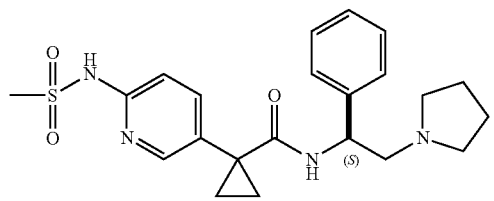

M.P: 182.2-182.4° C.
$^1$H NMR (400 MHz, DMSO-d$_6$): δ 10.08-10.66 (bs, 1H), 8.16 (s, 1H), 7.72 (dd, J$_1$=8.61 Hz, J$_2$=2.3 Hz, 1H), 7.3-7.19 (m, 6H), 6.98 (d, J=8.8 Hz, 1H), 4.85 (s, 1H), 3.26 (s, 3H), 2.76-2.31 (m, 6H), 1.6 (s, 4H), 1.36-1.25 (m, 2H), 1.01-0.98 (m, 2H)
IR (Neat, cm$^{-1}$): 3317, 3105, 2960, 2922, 2902, 1602
MS (ES): 429.2 (M$^+$+1)

Example 96

Synthesis of (S)-1-(2,2-dioxido-1H-benzo[c][1,2]thiazin-6-yl)-N-(1-phenyl-2-(pyrrolidin-1-yl)ethyl)cyclopropanecarboxamide

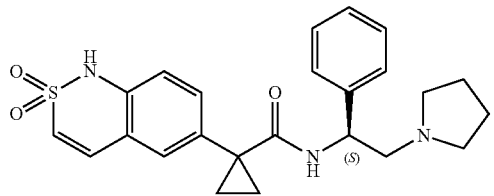

M.P: 163-165° C.
$^1$H NMR (400 MHz, DMSO-d$_6$): δ 11.2-10.8 (bs, 1H), 7.46 (d, J=1.8 Hz, 1H), 7.36 (d, J=4.0 Hz, 1H), 7.34-7.32 (m, 1H), 7.29-7.20 (m, 5H), 7.15 (d, J=6.9 Hz, 1H), 6.94 (d, J=8.4 Hz, 1H), 6.88 (d, J=10.3 Hz, 1H), 4.91-4.86 (m, 1H), 2.86-2.78 (m, 2H), 2.54 (bs, 4H), 1.63 (bs, 4H), 1.35-1.32 (m, 2H), 1.28-1.25 (m, 2H)
IR (Neat, cm$^{-1}$): 3535, 3298, 3037, 1658, 1616, 1587, 1504, 1471, 1357, 1290, 1126
MS (ES): 438 (M$^+$+1)

Example 97

Synthesis of (S)-1-(1H-indazol-5-yl)-N-(1-phenyl-2-(pyrrolidin-1-yl)ethyl)cyclopropane carboxamide

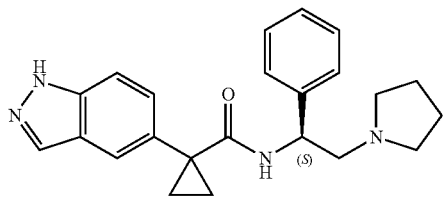

M.P: 82-83° C.
$^1$H NMR (400 MHz, DMSO-$d_6$): δ 13.08 (s, 1H), 8.06 (s, 1H), 7.80 (s, 1H), 7.55 (d, J=8.4 Hz, 1H), 7.40 (d, J=8.8 Hz, 1H), 7.29-7.20 (m, 2H), 7.18-7.16 (m, 3H), 6.89 (d, J=6.2 Hz, 1H), 4.69 (q, J=6.5 Hz, 1H), 2.54-2.45 (m, 2H), 2.17-2.12 (m, 4H), 1.41-1.27 (m, 6H), 1.17-1.07 (m, 1H), 1.07-1.01 (m, 1H)
IR (KBr, cm$^{-1}$): 3302, 2964, 1635, 1500, 1446, 1298, 1180, 1134
MS (ES): m/z 376.2 (M$^+$+1)

Example 98

Synthesis of (S)-1-(benzo[d]isoxazol-5-yl)-N-(1-phenyl-2-(pyrrolidin-1-yl)ethyl)cyclopropane carboxamide

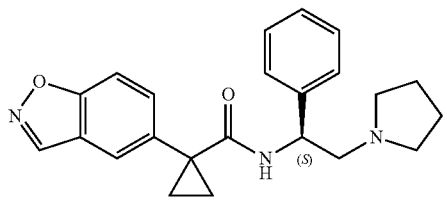

M.P: 129-130° C.
$^1$H NMR (400 MHz, DMSO-$d_6$): δ 11.50-11.00 (bs, 1H), 7.56 (s, 1H), 7.40-7.46 (m, 1H), 7.29-7.25 (m, 2H), 7.21-7.17 (m, 3H), 7.09 (d, J=6.6 Hz, 1H), 6.96 (d, J=8.4 Hz, 1H), 4.76-4.70 (m, 1H), 2.67-2.60 (m, 1H), 2.54-2.51 (m, 1H), 2.30 (bs, 4H), 1.59 (bs, 4H), 1.33-1.28 (m, 1H), 1.21-1.19 (m, 1H), 1.04-0.99 (m, 1H), 0.95-0.90 (m, 1H)
IR (KBr, cm$^{-1}$): 3065, 2797, 1765, 1649, 1535, 1262
MS (ES): 376.0 (M$^+$+1)

Example 99

Synthesis of (S)-3-(1-(1-phenyl-2-(pyrrolidin-1-yl)ethylcarbamoyl)cyclopropyl)benzoic acid

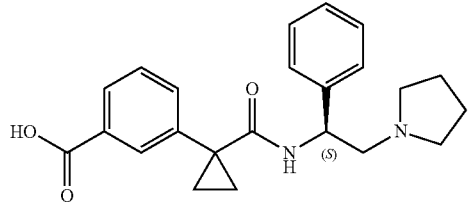

$^1$H NMR (400 MHz, DMSO-$d_6$): δ 13.0 (bs, 1H), 7.90 (s, 1H), 7.88 (d, J=7.69 Hz, 1H), 7.63 (d, J=7.69 Hz, 1H), 7.50 (d, J=7.69 Hz, 1H), 7.29-7.26 (m, 2H), 7.21-7.17 (m, 3H), 7.13 (s, 1H), 4.78-4.73 (q, J$_1$=5.86 Hz, J$_2$=6.22 Hz, 1H), 2.64 (d, J=8.79 Hz, 2H), 2.29-2.26 (t, J=5.86 Hz, 4H), 1.535 (s, 4H), 1.39 (d, J=3.29 Hz, 2H), 1.09-1.09 (d, J=3.29 Hz, 2H)
IR (KBr, cm$^{-1}$): 3263, 2883, 2206, 1647, 1489, 1375, 1184
MS (ES): 379.0 (M$^+$+1)

Example 100

Synthesis of (S)—N-(1-(3-methoxyphenyl)-2-(pyrrolidin-1-yl)ethyl)-1-(2-oxo-2,3-dihydrobenzo[d]oxazol-5-yl)cyclopropanecarboxamide

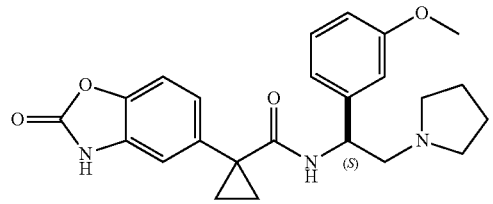

M.P: 92-94° C.
$^1$H NMR (400 MHz, DMSO-$d_6$): δ 11.66 (bs, 1H), 7.29 (d, J=8.4 Hz, 1H), 7.20-7.13 (m, 2H), 7.07 (d, J=1.5 Hz, 1H), 6.95 (d, J=6.6 Hz, 1H), 6.77-6.74 (m, 3H), 4.70 (q, J=6.7 Hz, 1H), 3.71 (s, 3H), 2.59-2.56 (m, 2H), 2.26 (bs, 4H), 1.51 (bs, 4H), 1.37-1.33 (m, 1H), 1.29-1.24 (m, 1H), 1.04-0.99 (m, 2H)
IR (KBr, cm$^{-1}$): 3093, 2960, 2833, 1776, 1655, 1585, 1492, 1465, 1492, 1465, 1255
MS (ES): m/z 422.3 (M$^+$+1)

Example 101

Synthesis of N—((S)-2-((S)-3-hydroxypyrrolidin-1-yl)-1-phenylethyl)-1-(2-oxo-2,3-dihydrobenzo[d]oxazol-5-yl)cyclopropanecarboxamide

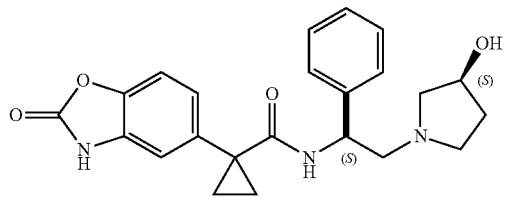

M.P: 142-144° C.
$^1$H NMR (400 MHz, DMSO-$d_6$): δ 11.20 (bs, 1H), 7.29-7.25 (m, 2H), 7.20-7.18 (m, 2H), 7.15-7.09 (m, 3H), 7.02 (d, J=6.9 Hz, 1H), 4.77-4.72 (m, 1H), 4.08-4.03 (m, 1H), 2.63-2.53 (m, 3H), 2.45-2.39 (m, 1H), 2.33-2.23 (m, 1H), 2.17-2.13 (m, 1H), 1.80-1.71 (m, 1H), 1.44-1.34 (m, 2H), 1.28-1.23 (m, 1H), 1.07-1.03 (m, 1H), 0.99-0.95 (m, 1H)
IR (KBr, cm$^{-1}$): 3057, 2810, 1776, 1653, 1501, 1350, 1256
MS (ES): m/z 408.1 (M$^+$+1)

Example 102

Synthesis of (S)-tert-butyl 2-(2-oxo-5-(1-(1-phenyl-2-(pyrrolidin-1-yl)ethylcarbamoyl)cyclopropyl)benzo[d]oxazol-3(2H)-yl)acetate

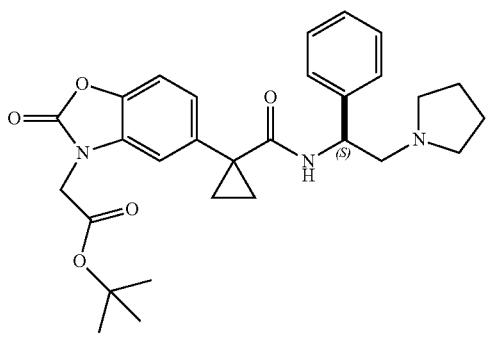

$^1$H NMR (400 MHz, DMSO-d$_6$): δ 7.29-7.15 (m, 6H), 7.04 (s, 1H), 6.91 (s, 1H), 6.10 (bs, 1H), 4.97 (bs, 1H), 4.50 (s, 2H), 3.01 (bs, 1H), 2.63 (bs, 5H), 1.75 (bs, 4H), 1.26 (bs, 9H), 1.20 (bs, 1H), 1.10-1.08 (m, 1H), 0.99-0.97 (m, 1H), 0.88-0.86 (m, 1H)
MS (ES): m/z 506.1 (M$^+$+1)

Example 103

Synthesis of (S)-2-(2-oxo-5-(1-(1-phenyl-2-(pyrrolidin-1-yl)ethylcarbamoyl)cyclopropyl)benzo[d]oxazol-3 (2H)-yl)acetic acid hydrochloride

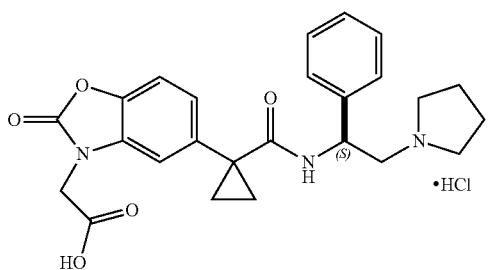

M.P: 166-168° C.
$^1$H NMR (400 MHz, DMSO-d$_6$): δ 13.40 (bs, 1H), 10.10 (bs, 1H), 7.60 (d, J=8.8 Hz, 1H), 7.47 (s, 1H), 7.37-7.33 (m, 3H), 7.29-7.27 (m, 3H), 7.18 (d, J=8.0 Hz, 1H), 5.36-5.34 (m, 1H), 4.68 (d, J=4.0 Hz, 2H), 3.57 (s, 4H), 3.41-3.36 (m, 2H), 1.93 (bs, 4H), 1.41 (bs, 2H), 1.11-1.01 (m, 2H)
IR (Neat, cm$^{-1}$): 2957, 2694, 2596, 2486, 1782, 1659, 1495, 1242
MS (ES): m/z 450.2 (M$^+$+1)

Example 104

Synthesis of (S)—N-(1-cyclohexyl-2-(pyrrolidin-1-yl)ethyl)-1-(2-oxo-2,3-dihydrobenzo[d]oxazol-5-yl)cyclopropanecarboxamide

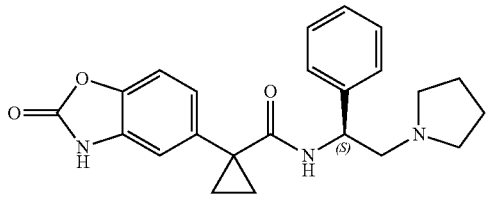

$^1$H NMR (400 MHz, DMSO-d$_6$): δ 11.5 (bs, 1H), 7.25 (d, J=8.1 Hz, 1H), 7.08 (d, J=8.1 Hz, 1H), 7.02 (s, 1H), 6.18 (d, J=8.4 Hz, 1H), 3.68-3.65 (m, 1H) 2.43-2.33 (m, 6H), 1.62-1.48 (m, 9H), 1.37-1.23 (m, 3H), 1.13-0.70 (m, 7H)
IR (Neat, cm$^{-1}$): 3352, 2926, 2850, 1774, 1656, 1512, 1467, 1346, 1288
MS (ES): m/z 398.0 (M$^+$+1)

Example 105

Synthesis of (S)-1-(3-methyl-1H-indazol-5-yl)-N-(1-phenyl-2-(pyrrolidin-1-yl)ethyl)cyclopropane carboxamide

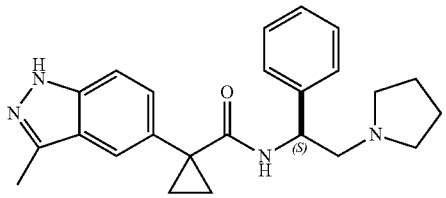

$^1$H NMR (400 MHz, DMSO-d$_6$): δ 12.63 (s, 1H), 7.73 (s, 1H), 7.47-7.42 (m, 1H), 7.38-7.35 (m, 1H), 7.30-7.25 (m, 2H), 7.20-7.16 (m, 3H), 6.87 (d, J=5.5 Hz, 1H), 4.70 (d, J=6.3 Hz, 1H), 2.55 (bs, 2H), 2.51 (s, 3H), 2.25-2.10 (bs, 4H), 1.37-1.23 (m, 6H), 1.10-1.03 (m, 2H)
IR (KBr, cm$^{-1}$): 3246, 2928, 2801, 1651, 1504, 1445, 1304
MS (ES): m/z 389.3 (M$^+$+1)

Example 106

Synthesis of (S)—N-(1-(3-methoxyphenyl)-2-(pyrrolidin-1-yl)ethyl)-1-(3-methyl-1H-indazol-5-yl)cyclopropanecarboxamide

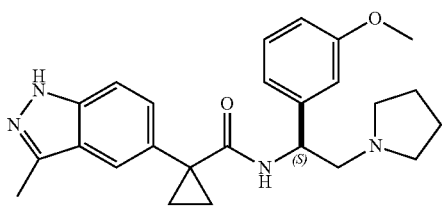

$^1$H NMR (400 MHz, DMSO-d$_6$): δ 12.63 (s, 1H), 7.73 (s, 1H), 7.47-7.44 (m, 1H), 7.38-7.35 (m, 1H), 7.20-7.16 (m, 1H), 6.86 (d, J=6.2 Hz, 1H), 6.76-6.72 (m, 3H), 4.68 (d, J=6.6 Hz, 1H), 3.70 (s, 3H), 2.55 (bs, 2H), 2.50 (bs, 3H), 2.25-2.10 (bs, 4H), 1.41-1.24 (m, 6H), 1.10-1.02 (m, 2H)
IR (KBr, cm$^{-1}$): 3246, 2961, 2932, 2803, 1647, 1506, 1437, 1283
MS (ES): m/z 419.2 (M$^+$+1)

Example 107

Synthesis of (S)-4-(1-(1-phenyl-2-(pyrrolidin-1-yl) ethyl carbamoyl)cyclopropyl)benzoic acid

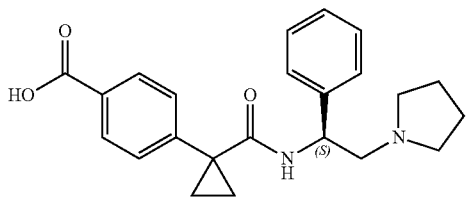

M.P: 134-136° C.
$^1$H NMR (400 MHz, DMSO-$d_6$): δ 13.0 (bs, 1H), 7.91 (d, J=8.0 Hz, 1H), 7.50 (d, J=8.0 Hz, 1H), 7.30-7.20 (m, 8H), 4.75 (d, J=5.5 Hz, 1H), 2.65 (d, J=9.5 Hz, 2H), 2.34-2.30 (m, 4H), 1.56 (bs, 4H), 1.39-1.29 (m, 2H), 1.10-1.09 (m, 2H)
IR (KBr, cm$^{-1}$): 3001, 1656, 1587, 1500, 1382, 1298
MS (ES): m/z 379.3 (M$^+$+1)

Example 108

Synthesis of (S)-1-(3-methyl-2-oxo-2,3-dihydrobenzo[d]oxazol-5-yl)-N-(1-phenyl-2-(pyrrolidin-1-yl)ethyl)cyclopropanecarboxamide

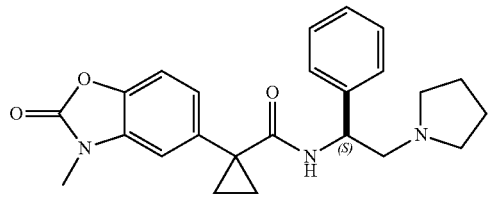

M.P: 96-98° C.
$^1$H NMR (400 MHz, CDCl$_3$): δ 8.78 (s, 1H), 8.65 (bs, 1H), 8.12-8.06 (m, 2H), 7.82-7.74 (m, 2H), 7.33-7.20 (m, 5H), 4.98-4.93 (m, 1H), 2.85 (t, J=11.0 Hz, 1H), 2.64-2.59 (m, 1H), 2.47 (bs, 2H), 2.39 (bs, 2H), 1.92-1.80 (m, 4H), 1.65-1.43 (bs, 4H)
IR (KBr, cm$^{-1}$): 3230, 3007, 2957, 2602, 2478, 1657, 1529, 1492, 1450, 1367, 1215
MS (ES): m/z 387.3 (M$^+$+1)

Example 109

Synthesis of N—((S)-1-cyclohexyl-2-((S)-3-hydroxypyrrolidin-1-yl)ethyl)-1-(2-oxo-2,3-dihydro benzo[d]oxazol-5-yl)cyclopropanecarboxamide

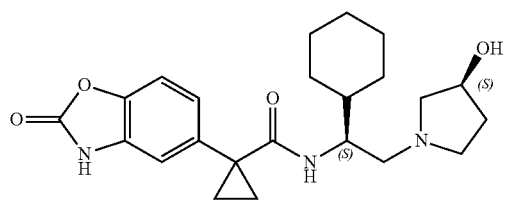

$^1$H NMR (400 MHz, CDCl$_3$): δ 7.24 (d, J=7.7 Hz, 1H), 7.07-7.05 (m, 2H), 6.19 (d, J=8.8 Hz, 1H), 4.14-4.09 (m, 1H), 3.67-3.62 (m, 1H), 2.6 (dd, J$_1$=9.5 Hz, J$_2$=6.2 Hz, 1H), 2.52-2.47 (m, 1H), 2.37-2.25 (m, 3H), 2.2 (dd, J=9.5 Hz, J$_2$=3.7 Hz, 1H), 1.92-1.84 (m, 1H), 1.64-1.23 (m, 9H), 1.16-0.62 (m, 7H)
IR (Neat, cm$^{-1}$): 3342, 1776, 1641, 1514, 1384, 1199, 1097
MS (ES): m/z 414.3 (M$^+$+1)

Example 110

Synthesis of (S)—N-(1-(3-cyanophenyl)-2-(pyrrolidin-1-yl)ethyl)-1-(2-oxo-2,3-dihydrobenzo[d]oxazol-5-yl)cyclopropanecarboxamide

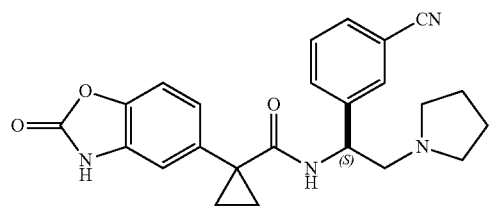

M.P: 106-108° C.
$^1$H NMR (400 MHz, DMSO-$d_6$): δ 11.76 (bs, 1H), 7.68 (d, J=8.4 Hz, 2H), 7.56-7.48 (m, 2H), 7.29 (d, J=8.4 Hz, 1H), 7.15-7.13 (m, 1H), 7.09-7.08 (m, 2H), 4.76 (d, J=6.6 Hz, 1H), 2.58 (d, J=7.3 Hz, 2H), 2.28 (s, 4H), 1.53 (bs, 4H), 1.38-1.34 (m, 1H), 1.28-1.24 (m, 1H), 1.11-1.04 (m, 1H), 0.99-0.96 (m, 1H)
IR (KBr, cm$^{-1}$): 3077, 2974, 2808, 2228, 1776, 1659, 1501, 1288, 1256
MS (CI): m/z 416.47 (M$^+$+1)

Example 111

Synthesis of (S)-3-(1-(1-(2-oxo-2,3-dihydrobenzo[d]oxazol-5-yl)cyclopropanecarboxamido)-2-(pyrrolidin-1-yl)ethyl)benzamide

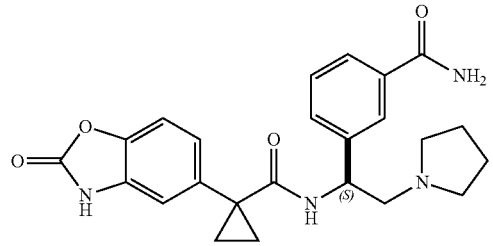

M.P: 139-141° C.
$^1$H NMR (400 MHz, $^1$H DMSO-$d_6$): δ 11.50 (bs, 1H), 7.92 (s, 1H), 7.72-7.68 (m, 2H), 7.37-7.32 (m, 3H), 7.24 (d, J=8.4 Hz, 1H), 7.11-7.06 (m, 2H), 7.00 (d, J=6.3 Hz, 1H), 4.76-4.71 (m, 1H), 2.59-2.54 (m, 2H), 2.28-2.25 (m, 4H), 1.52 (bs, 4H), 1.35 (d, J=6.6 Hz, 1H), 1.24 (d, J=4.4 Hz, 1H), 1.04 (d, J=6.6 Hz, 1H), 0.97 (d, J=8.4 Hz, 1H)
IR (KBr, cm$^{-1}$): 3315, 3192, 2808, 1776, 1658, 1581, 1500, 1408, 1350, 1257
MS (ES): m/z 435(M$^+$+1)

Example 112

Synthesis of (S)-2-(3-(1-(1-(3-(methylsulfonamido)phenyl)cyclopropanecarboxamido)-2-(pyrrolidin-1-yl)ethyl)phenoxy)acetic acid

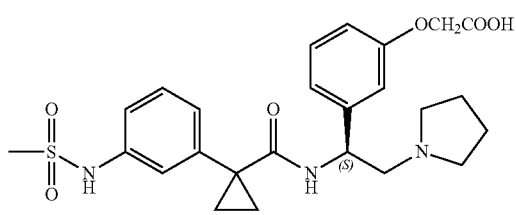

M.P: 160-162° C.

$^1$H NMR (400 MHz, DMSO-d$_6$): δ 12.00 (bs, 1H), 11.50 (bs, 1H), 7.69 (s, 1H), 7.48 (d, J=8.8 Hz, 1H), 7.37 (t, J=7.7 Hz, 1H), 7.22 (d, J=7.7 Hz, 1H), 7.01 (t, J=7.8 Hz, 1H), 6.70 (s, 1H), 6.52-6.48 (m, 3H), 4.79 (bs, 1H), 4.19 (s, 2H), 3.17 (s, 3H), 2.67 (bs, 2H), 2.50 (bs, 4H), 1.59 (bs, 4H), 1.34-1.27 (m, 2H), 1.14-0.85 (m, 2H)

IR (KBr, cm$^{-1}$): 3010, 2920, 2854, 1726, 1658, 1585, 1492, 1452, 1390, 1330, 1282

MS (ES): m/z 502.4 (M$^+$+1)

Example 113

Synthesis of (S)—N-(1-(3-(benzyloxy)phenyl)-2-(pyrrolidin-1-yl)ethyl)-1-(2-oxo-2,3-dihydrobenzo[d]oxazol-5-yl)cyclopropanecarboxamide

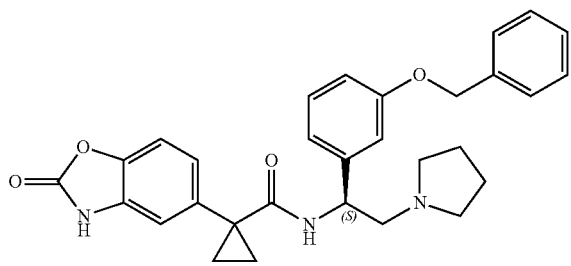

M.P: 94-96° C.

$^1$H NMR (400 MHz, DMSO-d$_6$): δ 11.8-11.6 (bs, 1H), 7.44-7.31 (m, 5H), 7.27 (d, J=8.06 Hz, 1H), 7.18-7.07 (m, 3H), 6.95 (d, J=6.59 Hz, 1H), 6.84-6.82 (m, 2H), 6.76 (d, J=7.69 Hz, 1H), 5.05 (s, 2H), 4.72-4.67 (m, 1H), 2.56-2.54 (m, 2H), 2.24 (bs, 4H), 1.49 (bs, 4H), 1.38-1.25 (m, 2H), 1.24-0.97 (m, 2H)

IR (KBr, cm$^{-1}$): 3064, 2958, 2808, 1774, 1656, 1585, 1500, 1255

MS (ES): m/z 498 (M$^+$+1)

Example 114

Synthesis of (S)—N-(1-(3-hydroxyphenyl)-2-(pyrrolidin-1-yl)ethyl)-1-(2-oxo-2,3-dihydrobenzo[d]oxazol-5-yl)cyclopropanecarboxamide

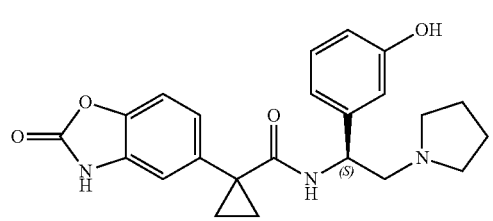

M.P: 132-134° C.

$^1$H NMR (400 MHz, DMSO-d$_6$): δ 11.8-11.6 (bs, 1H), 9.28 (bs, 1H), 7.28 (d, J=8.06 Hz, 1H), 7.15 (d, J=1.46 Hz, 1H), 7.13-7.03 (m, 2H), 6.88 (d, J=6.59 Hz, 1H), 6.60-6.57 (m, 3H), 4.64-4.59 (m, 1H), 2.54-2.53 (m, 2H), 2.21 (bs, 4H), 1.49 (bs, 4H), 1.36-1.27 (m, 2H), 1.03-0.96 (m, 2H)

IR (KBr, cm$^{-1}$): 3086, 2964, 2814, 1776, 1658, 1589, 1500, 1257

MS (ES): m/z 408 (M$^+$+1)

Example 115

Synthesis of (S)-1-(4-cyanophenyl)-N-(1-phenyl-2-(pyrrolidin-1-yl)ethyl)cyclopropane carboxamide

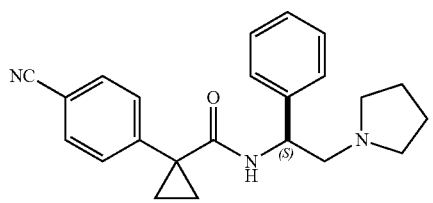

$^1$H NMR (400 MHz, DMSO-d$_6$): δ 7.82 (d, J=8.06 Hz, 2H), 7.56 (d, J=8.42 Hz, 2H), 7.23 (d, J=8.06 Hz, 1H), 7.18 (m, 5H), 4.88-4.80 (q, J$_1$=6.9 Hz, J$_2$=6.6 Hz, 1H), 2.66 (d, J=8.42 Hz, 2H), 2.35-2.30 (t, J=6.75 Hz, 4H), 1.59 (s, 4H), 1.42-1.41 (m, 1H), 1.39-1.38 (m, 1H), 1.08-1.06 (m, 1H), 1.05-1.03 (m, 1H)

IR (KBr, cm$^{-1}$): 3336, 2796, 2227, 1666, 1500, 1294, 1136

MS (ES): m/z 360.1 (M$^+$+1)

Example 116

Synthesis of (S)-3-(1-(1-(2-oxo-2,3-dihydrobenzo[d]oxazol-5-yl)cyclopropanecarboxamido)-2-(pyrrolidin-1-yl)ethyl)phenyl methanesulfonate 2,2,2-trifluoroacetate

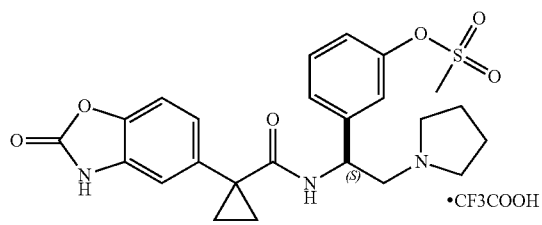

M.P: 101-103° C.

$^1$H NMR (400 MHz, DMSO-d$_6$): δ 7.41-7.37 (m, 1H), 7.23-7.10 (m, 4H), 7.07-7.02 (m, 3H), 4.77-4.73 (m, 1H), 3.34 (s, 3H), 2.56 (m, 2H), 2.25 (bs, 4H), 1.50 (bs, 4H), 1.33-1.23 (m, 2H), 1.04-0.97 (m, 2H)

IR (KBr, cm$^{-1}$): 3026, 2808, 1776, 1768, 1651, 1504, 1359, 1178

MS (ES): m/z 486 (M$^+$+1)

Example 117

Synthesis of (S)—N-(1-(3-(2H-tetrazol-5-yl)phenyl)-2-(pyrrolidin-1-yl)ethyl)-1-(2-oxo-2,3-dihydrobenzo[d]oxazol-5-yl)cyclopropanecarboxamide

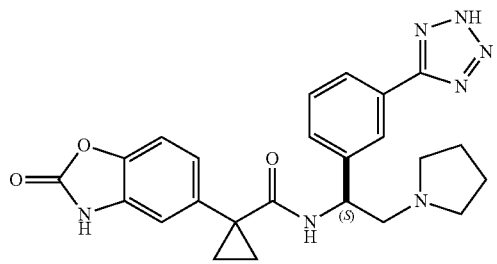

M.P: 107-109° C.

$^1$H NMR (400 MHz, DMSO-d$_6$): δ 13.56 (bs, 1H), 11.73 (bs, 1H), 8.06 (s, 1H), 7.93 (d, J=7.7 Hz, 1H), 7.66 (d, J=8.4 Hz, 1H), 7.57 (t, J=7.1 Hz, 1H), 7.45 (d, J=6.9 Hz, 1H), 7.27 (d, J=8.1 Hz, 1H), 7.13-7.10 (m, 2H), 5.39 (bs, 1H), 3.62-3.17 (m, 6H), 1.92 (bs, 4H), 1.41 (bs, 2H), 1.24-1.11 (m, 1H), 1.04-0.99 (m, 1H)

IR (KBr, cm$^{-1}$): 3340, 3062, 2958, 2927, 2858, 2733, 1766, 1737, 1651, 1512, 1462

MS (ES): m/z 460 (M$^+$+1)

Example 118

Synthesis of N—((S)-2-((S)-3-hydroxypyrrolidin-1-yl)-1-(3-methoxyphenyl)ethyl)-1-(2-oxo-2,3-dihydrobenzo[d]oxazol-5-yl)cyclopropanecarboxamide

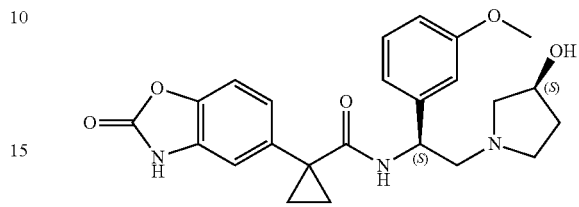

M.P: 125-127° C.

$^1$H NMR (400 MHz, $^1$H DMSO-d$_6$): δ 12.0 (bs, 1H), 7.27 (d, J=8.4 Hz, 1H), 7.18 (t, J=7.7 Hz, 1H), 7.14-7.08 (m, 2H), 7.02-6.95 (m, 1H), 6.77-6.74 (m, 3H), 4.75-4.69 (m, 1H), 4.50 (bs, 1H), 4.05-4.00 (m, 1H), 3.71 (s, 3H), 2.62-2.54 (m, 2H), 2.44-2.33 (m, 2H), 2.26 (q, J=6.9 Hz, 1H), 2.17-2.05 (m, 1H), 1.78-1.72 (m, 1H), 1.44-1.33 (m, 2H), 1.28-1.24 (m, 1H), 1.04-0.96 (m, 2H)

IR (Neat, cm$^{-1}$): 3340, 3008, 2953, 1768, 1639, 1585, 1512, 1346, 1257, 1199, 1155

MS (ES): m/z 438.0 (M$^+$+1)

Example 119

Synthesis of (S)-methyl 4-((5-(1-(1-(3-hydroxyphenyl)-2-(pyrrolidin-1-yl)ethylcarbamoyl)cyclopropyl)-2-oxobenzo[d]oxazol-3(2H)-yl)methyl)benzoate

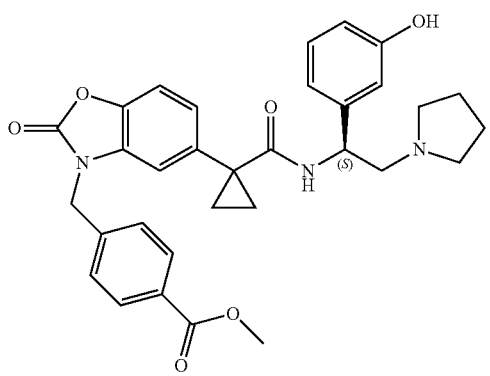

M.P: 119-120° C.

$^1$H NMR (400 MHz, $^1$H DMSO-d$_6$): δ 9.30 (s, 1H), 7.93 (d, J=8.0 Hz, 2H), 7.55 (d, J=8.8 Hz, 2H), 7.38 (s, 2H), 7.22 (d, J=8.0 Hz, 1H), 7.02 (t, J=7.7 Hz, 1H), 6.84 (s, 1H), 6.60-6.50 (m, 3H), 5.17 (s, 2H), 4.63 (bs, 1H), 3.81 (s, 3H), 2.50 (bs, 2H), 2.18 (bs, 4H), 1.40 (bs, 4H), 1.30-1.23 (m, 2H), 1.00 (bs, 2H)

IR (Neat, cm$^{-1}$): 2953, 1778, 1720, 1678, 1493, 1282, 1022

MS (ES): m/z 556 (W$^+$+1)

Example 120

Synthesis of (S)-methyl 3-((5-(1-(1-(3-hydroxyphenyl)-2-(pyrrolidin-1-yl)ethylcarbamoyl)cyclopropyl)-2-oxobenzo[d]oxazol-3(2H)-yl)methyl)benzoate

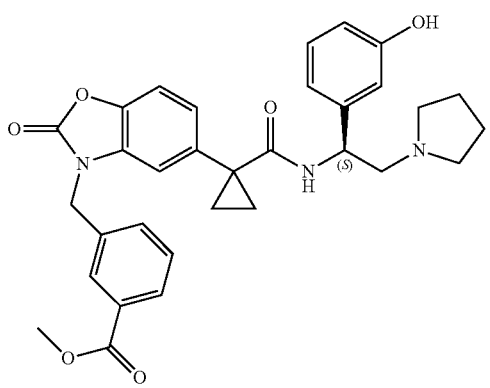

M.P: 112-113° C.

$^1$H NMR (400 MHz, $^1$H DMSO-d$_6$): δ 9.30 (bs, 1H), 8.05 (s, 1H), 7.90 (d, J=7.8 Hz, 1H), 7.10 (d, J=7.3 Hz, 1H), 7.52 (t, J=7.8 Hz, 1H), 7.42-7.37 (m, 2H), 7.23 (d, J=8.0 Hz, 1H), 7.02 (t, J=7.7 Hz, 1H), 6.84 (d, J=6.6 Hz, 1H), 6.59-6.53 (m, 3H), 5.17 (s, 2H), 4.58 (d, J=6.6 Hz, 1H), 3.83 (s, 3H), 2.48-2.42 (m, 2H), 2.09 (bs, 4H), 1.35 (bs, 4H), 1.28-1.23 (m, 2H), 1.01 (s, 2H)

IR (Neat, cm$^{-1}$): 2974, 1780, 1659, 1493, 1288

MS (ES): m/z 556.0 (M$^+$+1)

Example 121

Synthesis of N—((S)-1-(3-hydroxyphenyl)-2-(S)-3-hydroxypyrrolidin-1-yl)ethyl)-1-(2-oxo-2,3-dihydrobenzo[d]oxazol-5-yl)cyclopropanecarboxamide

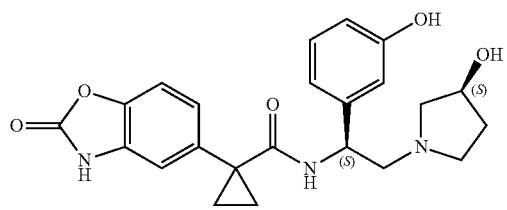

M.P: 112-114° C.

$^1$H NMR (400 MHz, DMSO-d$_6$): δ 9.25 (bs, 1H), 7.26 (d, J=8.1 Hz, 1H), 7.14-7.03 (m, 3H), 6.92 (d, J=7.20 Hz, 1H), 6.87 (d, J=7.2 Hz, 1H), 6.60-6.56 (m, 3H), 4.66-4.59 (m, 1H), 4.07-3.97 (m, 1H), 3.17 (s, 1H), 2.67-2.49 (m, 2H), 2.41-2.21 (m, 2H), 2.14-2.02 (m, 1H), 1.77-1.70 (m, 1H), 1.45-1.35 (m, 2H), 1.30-1.23 (m, 2H), 1.09-0.94 (m, 2H)

IR (KBr, cm$^{-1}$): 3161, 2960, 2821, 1766, 1641, 1589, 1502, 1460, 1344, 1284, 1257

MS (CI): m/z 423.4 (M$^+$+1)

Example 122

Synthesis of N—((S)-2-((S)-3-hydroxypyrrolidin-1-yl)-1-(3-nitrophenyl)ethyl)-1-(2-oxo-2,3-dihydrobenzo[d]oxazol-5-yl)cyclopropanecarboxamide

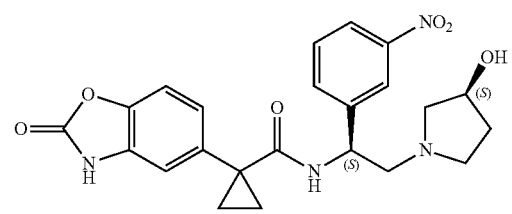

M.P: 224-226° C.

$^1$H NMR (400 MHz, DMSO-d$_6$): δ 11.71 (bs, 1H), 8.08 (d, J=7.8 Hz, 2H), 7.69 (d, J=7.8 Hz, 1H), 7.60-7.57 (m, 1H), 7.29 (d, J=8.3 Hz, 1H), 7.20 (d, J=6.3 Hz, 1H), 7.15-7.13 (m, 1H), 7.12-7.07 (m, 1H), 4.87 (q, J=6.8 Hz, 1H), 2.67-2.54 (m, 2H), 2.30 (bs, 4H), 1.53 (bs, 4H), 1.38-1.34 (m, 1H), 1.28-1.24 (m, 1H), 1.10-0.97 (m, 2H)

IR (KBr, cm$^{-1}$): 3394, 3055, 1780, 1654, 1531, 1502, 1477, 1467, 1350, 1311, 1257

Example 123

Synthesis of (S)—N-(1-(3-aminophenyl)-2-(pyrrolidin-1-yl)ethyl)-1-(2-oxo-2,3-dihydrobenzo[d]oxazol-5-yl)cyclopropanecarboxamide

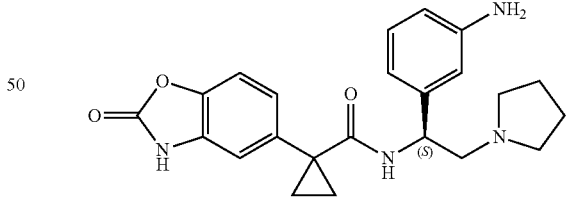

M.P: 95-97° C.

$^1$H NMR (400 MHz, DMSO-d$_6$): δ 11.73 (bs, 1H), 7.28 (d, J=8.3 Hz, 1H), 7.14 (d, J=8.3 Hz, 1H), 7.07 (s, 1H), 6.89 (t, J=7.5 Hz, 1H), 6.78 (d, J=6.8 Hz, 1H), 6.38-6.30 (m, 3H), 4.95 (bs, 2H), 4.55 (d, J=6.4 Hz, 1H), 2.50 (bs, 2H), 2.23 (d, J=7.3 Hz, 4H), 1.50 (s, 4H), 1.36-1.23 (m, 2H), 1.11-0.97 (m, 2H)

IR (KBr, cm$^{-1}$): 3342, 2972, 2808, 1776, 1658, 1604, 1502, 1467, 1352, 1294, 1257

MS (CI): m/z 406.5 (M$^+$+1)

Example 124

Synthesis of (S)-1-(2-oxoindolin-6-yl)-N-(1-phenyl-2-(pyrrolidin-1-yl)ethyl)cyclopropane carboxamide

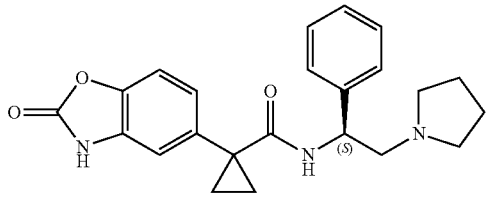

M.P: 115-118° C.
$^1$H NMR (400 MHz, DMSO-d$_6$): δ 10.44 (s, 1H), 7.30-7.26 (m, 2H), 7.22-7.17 (m, 4H), 6.99 (d, J=6.4 Hz, 2H), 6.82 (s, 1H), 4.71 (d, J=6.4 Hz, 1H), 3.46 (s, 2H), 2.60-2.56 (m, 2H), 2.32-2.24 (bs, 4H), 1.52 (bs, 4H), 1.36-1.32 (m, 2H), 1.00-0.94 (m, 2H)
IR (KBr, cm$^{-1}$): 3177, 2804, 1703, 1630, 1501, 1352, 1254, 1219
MS (ES): m/z 390.3 (M$^+$+1)

Example 125

Synthesis of (S)—N-(1-(3-(3-cyanobenzyloxy)phenyl)-2-(pyrrolidin-1-yl)ethyl)-1-(2-oxo-2,3-dihydrobenzo[d]oxazol-5-yl)cyclopropanecarboxamide

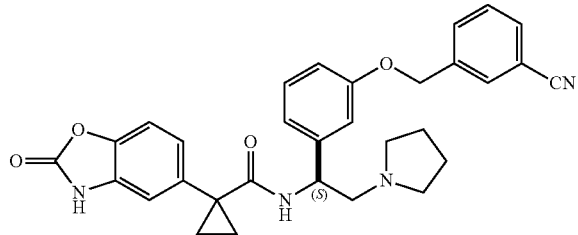

M.P: 129-130° C.
$^1$H NMR (400 MHz, DMSO-d$_6$): δ 11.63 (bs, 1H), 7.90 (s, 1H), 7.82 (d, J=7.6 Hz, 2H), 7.78 (d, J=8.0 Hz, 1H), 7.62 (t, J=7.6 Hz, 1H), 7.25-7.20 (m, 2H), 7.05-7.02 (m, 2H), 6.93 (dd, J$_1$=2.3 Hz, J$_2$=8.2 Hz, 1H), 6.82-6.80 (m, 2H), 5.72-5.70 (m, 1H), 5.12 (s, 2H), 2.68-2.60 (m, 1H), 2.59-2.54 (m, 1H), 2.36 (bs, 4H), 1.59 (bs, 4H), 1.50 (s, 2H), 1.23 (s, 2H)
IR (KBr, cm$^{-1}$): 3065, 2797, 1765, 1649, 1535, 1262
MS (ES): m/z 524.0 (M$^+$+1)

Example 126

Synthesis of (S)—N-(1-(3-(4-cyanobenzyloxy)phenyl)-2-(pyrrolidin-1-yl)ethyl)-1-(2-oxo-2,3-dihydrobenzo[d]oxazol-5-yl)cyclopropanecarboxamide

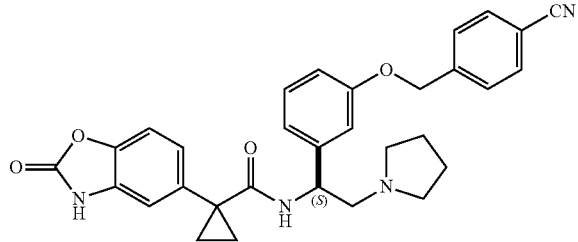

M.P: 88-89° C.
$^1$H NMR (400 MHz, DMSO-d$_6$): δ 11.60 (bs, 1H), 7.87 (d, J=7.9 Hz, 2H), 7.62 (d, J=7.8 Hz, 2H), 7.26-7.20 (m, 3H), 7.12-7.01 (m, 2H), 6.91 (d, J=7.8 Hz, 1H), 6.80 (s, 2H), 5.70 (bs, 1H), 5.18 (s, 2H), 2.68-2.58 (m, 2H), 2.37 (bs, 4H), 1.58 (bs, 4H), 1.48 (bs, 2H), 1.22 (bs, 2H)
IR (KBr, cm$^{-1}$): 3065, 2797, 1765, 1649, 1535, 1262
MS (ES): m/z 524.0 (M$^+$+1)

Example 127

Synthesis of 1-(2-oxo-2,3-dihydrobenzo[d]oxazol-5-yl)-N-(2-(pyrrolidin-1-yl)-1-(tetrahydro-2H-pyran-4-yl)ethyl)cyclopropanecarboxamide

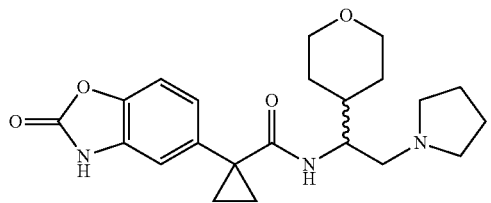 [SMILES: O=C(NC(CN1CCCC1)C1CCOCC1)C1(c2ccc3oc(=O)[nH]c3c2)CC1]

$^1$H NMR (400 MHz, DMSO-d$_6$): δ 7.24 (d, J=8.3 Hz, 1H), 7.07 (dd, J$_1$=8.3 Hz, J$_2$=1.5 Hz, 1H), 7.01 (s, 1H), 6.27-6.22 (m, 1H), 3.80-3.78 (m, 2H) 3.68-3.63 (m, 1H), 3.20-3.13 (m, 2H), 2.42-2.32 (m, 6H), 1.6 (bs, 4H), 1.45 (d, J=12.7 Hz, 1H), 1.37-0.97 (m, 8H)
MS (ES): m/z 400.3 (M$^+$+1)

Example 128

Synthesis of N-(1-(1-benzyl-1H-pyrazol-4-yl)-2-(pyrrolidin-1-yl)ethyl)-1-(2-oxo-2,3-dihydrobenzo[d]oxazol-5-yl)cyclopropanecarboxamide

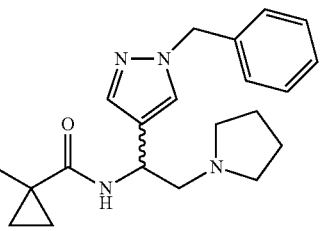

$^1$H NMR (400 MHz, DMSO-d$_6$): δ 11.60 (bs, 1H), 7.56 (s, 1H), 7.30-7.18 (m, 7H), 7.09-7.03 (m, 2H), 6.81 (d, J=7.33 Hz, 1H), 5.23 (s, 2H), 4.80 (q, J=7.33 Hz, 1H), 2.60 (d, J=6.72 Hz, 2H), 2.33 (s, 4H), 1.56 (s, 4H), 1.30 (d, J=3.0 Hz, 2H), 0.98 (d, J=4.3 Hz, 2H)
IR (KBr, cm$^{-1}$): 3068, 2966, 1776, 1651, 1502, 1257
MS (ES): m/z 472.2 (M$^+$+1)

Example 129

Synthesis of (S)-methyl 3-(2-oxo-5-(1-(1-phenyl-2-(pyrrolidin-1-yl)ethylcarbamoyl)cyclopropyl)benzo[d]oxazol-3 (2H)-yl)methyl)benzoate

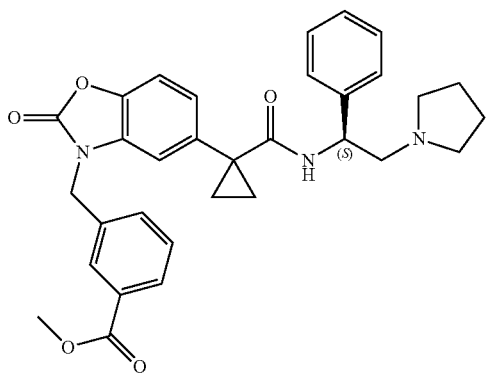

$^1$H NMR (400 MHz, DMSO-d$_6$): δ 8.06 (s, 1H), 7.9 (d, J=8.06 Hz, 1H), 7.71 (d, J=8.06 Hz, 1H), 7.52 (t, J=8.06 Hz, 1H) 7.44 (s, 1H), 7.39 (d, J=8.06 Hz, 1H), 7.26-7.11 (m, 6H), 6.87 (d, J=5.37 Hz, 1H), 5.17 (s, 2H), 4.67 (d, J=5.9 Hz, 1H), 3.83 (s, 3H), 2.5-2.45 (m, 2H), 2.11 (s, 4H), 1.38 (s, 4H), 1.28-1.23 (m, 2H), 1.01 (s, 2H)

IR (KBr, cm$^{-1}$): 3361, 2953, 2796, 1782, 1722, 1666, 1494, 1462, 1286, 1201, 1107

MS (ES): m/z 540.1 (M$^+$+1)

Example 130

Synthesis of (S)—N-(1-(3-(methylsulfonamido)phenyl)-2-(pyrrolidin-1-yl)ethyl)-1-(2-oxo-2,3-dihydrobenzo[d]oxazol-5-yl)cyclopropanecarboxamide

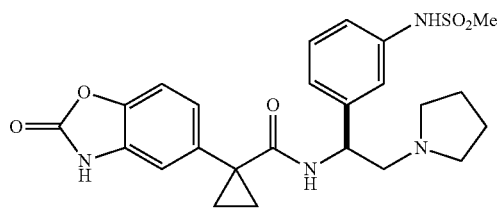

M.P: 114-116° C.

$^1$H NMR (400 MHz, DMSO-d$_6$): δ 12.0 (bs, 1H), 11.6 (bs, 1H), 9.81 (bs, 1H), 7.29 (t, J=7.8 Hz, 1H), 7.22 (d, J=8.6 Hz, 1H), 7.10-7.05 (m, 4H), 6.95 (d, J=7.5 Hz, 1H), 5.71 (bs, 1H), 2.98 (s, 3H), 2.67-2.60 (m, 1H), 2.50 (bs, 2H), 2.40 (bs, 3H), 1.61 (bs, 2H), 1.58-1.49 (m, 2H), 1.30-1.22 (m, 2H), 1.11-1.07 (m, 2H)

IR (KBr, cm$^{-1}$): 3572, 3080, 2958, 1764, 1591, 1500, 1467, 1362, 1328, 1286, 1257

MS (CI): m/z 484.5 (M$^+$+1)

Example 131

Synthesis of (S)—N-methyl-1-phenyl-N-(1-phenyl-2-(pyrrolidin-1-yl)ethyl]cyclobutane carboxamide hydrochloride

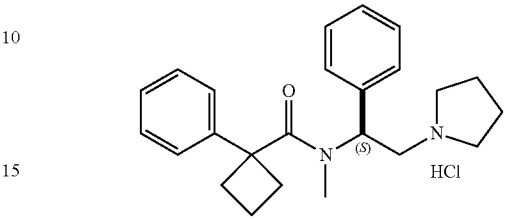

M.P: 234-235° C.

$^1$H NMR (400 MHz, DMSO-d$_6$): δ 10.1 (s, 1H), 7.36-7.29 (m, 8H), 7.2-7.1 (m, 2H), 6.1 (m, 1H), 3.97-3.90 (m, 1H), 3.73-3.70 (m, 1H), 3.69-3.54 (m, 2H), 3.39-3.37 (m, 1H), 3.18-3.06 (m, 4H), 2.59-2.54 (m, 1H), 2.25 (s, 3H), 2.0-1.7 (m, 6H)

IR (Neat, cm$^{-1}$): 3057, 2993, 2953, 2814, 2569, 2465, 1957, 1886, 1816, 1653, 1444, 1381, 1309, 1095

MS (ES): m/z 363.4 (M$^+$+1)

Example 132

In Vitro Assay to Evaluate Potency of KOR Agonists of Formula (I) Using IP-One Assay The potency of the test compounds to the human KOR receptor was determined by performing dose-response experiments in COS-7 cells transiently transfected with the human KOR receptor cDNA using IP-One HTRF assay.

IP-One assay: One day following transfection cells were seeded in ½-area 96 well plates (Corning Costar, #675083) with 40,000 cells/well in DMEM medium supplemented with 10% fetal calf serum, 2 mM glutamine and 0.01 mg/ml gentamicin. The following day, media was aspirated and 50 μl Stimulation buffer (10 mM HEPES, 1 mMCaCl2, 0.5 mM MgCl2, 4.2 mM KCl, 146 mM NaCl, 5.5 mM glucose, 50 mM LiCl, 0.1% BSA, pH7.4) were added to each well. Test compounds were dissolved in DMSO in various concentrations and 1 μl was added to each well to stimulate cells. Following an incubation of about 60 minutes at 37° C., 10 μL IP1-d2 (Cisbio) and 10 μl anti IP1-Cryptate (Cisbio) were added to each well. Plates were incubated at about 20-35° C. for a minimum of 60 minutes and counted on HTRF compatible Alpha-Fusion (Packard). Determinations were made in duplicates. EC$_{50}$ values were calculated using AssayExplorer 3.2 (Symyx), a standard pharmacological data handling software.

Using this protocol, various compounds as described herein were found to exhibit binding affinity towards KOR. For example, certain of the compounds as described herein exhibited a KOR agonistic binding in-vitro EC$_{50}$ values of less than or equal to 100 nM; certain of other compounds as described herein exhibited a KOR agonistic binding in-vitro EC$_{50}$ values between 100 nM-1 μM; and certain of other compounds as described herein exhibited a KOR agonistic binding in-vitro EC$_{50}$ values greater than or equal to 1 μM.

Although the invention has been illustrated by certain of the preceding examples, it is not to be construed as being limited thereby; but rather, the invention encompasses the generic area as hereinbefore disclosed. Various modifications and embodiments can be made without departing from the spirit and scope thereof.

What is claimed is:

1. A compound of formula (I) or a stereoisomer thereof or a pharmaceutically acceptable salt thereof:

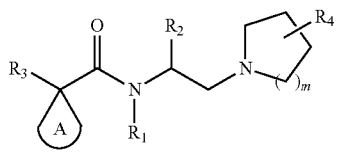

wherein
A represents a 3-7 membered cycloalkyl ring;
$R_1$ represents H or methyl, ethyl, propyl, butyl, or tert-butyl;
$R_2$ represents an optionally substituted group selected from isopropyl, isobutyl, benzyl, phenyl, pyridinyl, cyclohexyl, tetrahydro-2H-pyran-4-yl and pyrazol-4-yl, wherein the $R_2$ is optionally substituted one or more times independently with group selected from —CN, hydroxyl, —NO$_2$, —NR$_a$R$_b$, —OR$_c$, methyl, ethyl, benzyl, tetrazolyl, —(CH$_2$)$_n$—COOR$_d$ and —(CH$_2$)$_n$CON(R$_1$)$_2$;
$R_3$ represents an optionally substituted group selected from

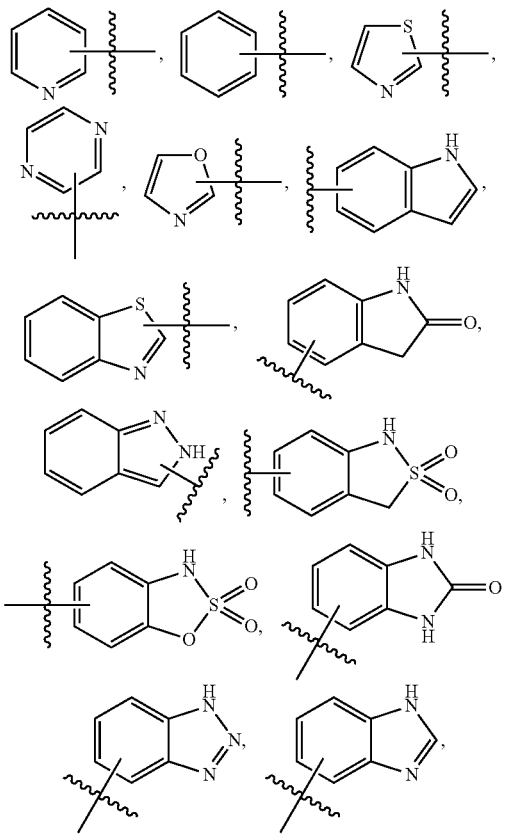

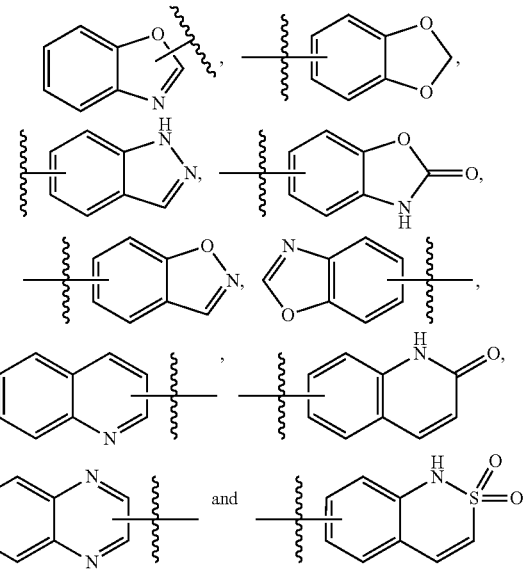

wherein
$R_3$ is optionally substituted one or more times independently with a group selected from —CN, hydroxyl, halogen, methyl, ethyl, propyl, phenyl, benzyl, tetrazolyl, —(CH$_2$)$_n$NR$_a$R$_b$, —OR$_c$, —SO$_2$R$_e$, —SO$_2$N(R$_1$)$_2$, —COR$_5$, —C(R$_e$)=N—OH, (CH$_2$)$_q$COOR$_d$ and

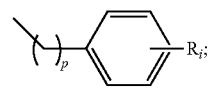

$R_4$ represents hydrogen, hydroxyl, halogen, CH$_2$OH, —N(R$_1$)$_2$ or —NHCOOR$_e$;
$R_a$, in each occurrence, independently selected from hydrogen and methyl;
$R_b$, in each occurrence, independently selected from hydrogen, methyl, —COOR$_1$, —CO—R$_1$ and —SO$_2$—R$_e$;
$R_e$, in each occurrence, independently selected from methyl, ethyl, propyl, butyl and tert-butyl;
$R_c$, in each occurrence, independently selected from hydrogen, methyl, ethyl, propyl, —SO$_2$—R$_e$, —(CH$_2$)$_p$COOR$_d$ and

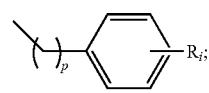

$R_i$, in each occurrence, independently selected from hydrogen, methyl, ethyl, —CN, halogen, and —COOR$_d$;
$R_d$, in each occurrence, independently selected from hydrogen, methyl and ethyl;
$R_5$ represents methyl, ethyl or —N(R$_1$)$_2$;
m represents 0 or 1; and
n, p and q, in each occurrence, independently selected from 0 or 1.

2. The compound according to claim 1 having the formula (Ia):

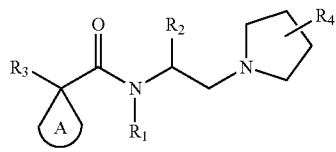

wherein $R_3$ is selected from optionally substituted:

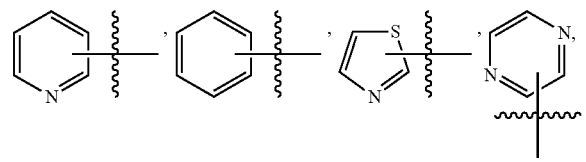
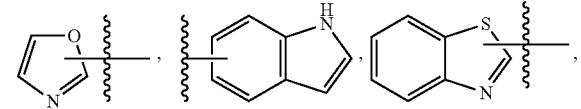
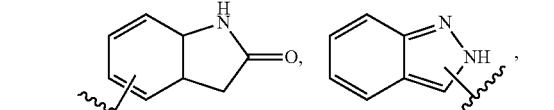
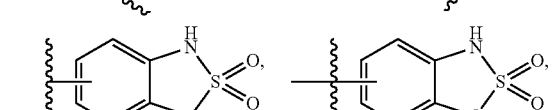
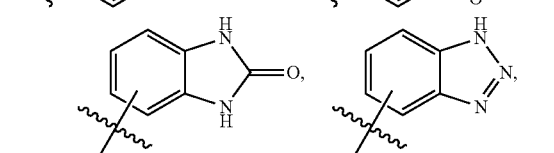
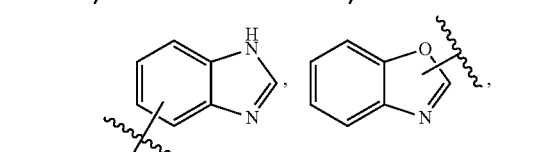
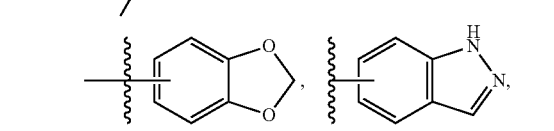
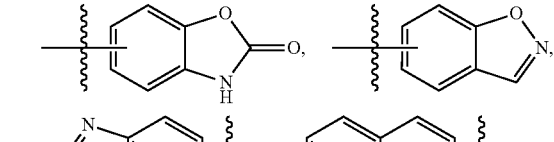
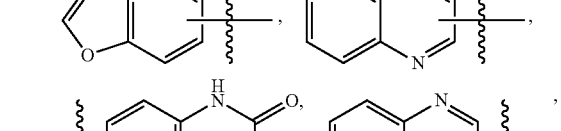
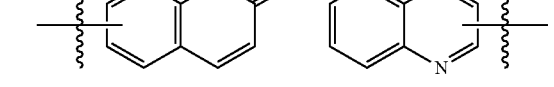
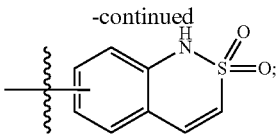

and wherein $R_3$ is optionally substituted with one or more substituents selected independently from —CN, hydroxyl, halogen, methyl, ethyl, propyl, phenyl, benzyl, tetrazolyl, —(CH$_2$)$_n$NR$_a$R$_b$, —OR$_c$, —SO$_2$R$_e$, —SO$_2$N(R$_1$)$_2$, —COR$_5$, —C(R$_e$)=N—OH, —(CH$_2$)$_q$COOR$_d$ and

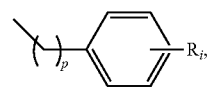

wherein A, $R_a$, $R_b$, $R_c$, $R_d$, $R_e$, $R_1$, $R_1$, $R_2$, $R_4$, $R_5$, n, p and q are as defined in claim 1.

3. The compound according to claim 1 having the formula (Ib):

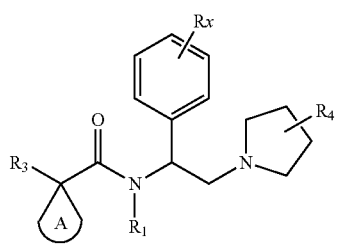

wherein $R_x$ represents —CN, hydroxyl, —NO$_2$, —NR$_a$R$_b$, —OR, methyl, ethyl, benzyl, tetrazolyl, —(CH$_2$)—COOR$_d$ or —(CH$_2$)—CON(R$_1$)$_2$, wherein $R_a$ represents hydrogen or methyl;

$R_b$ represents hydrogen, methyl, —COOR$_1$, —CO—R$_1$ or —SO$_2$—R$_e$, wherein $R_1$ is as defined in claim 1; and $R_e$ represents methyl, ethyl, propyl, butyl or tert-butyl;

$R_c$ represents hydrogen, methyl, ethyl, propyl, —SO$_2$—R$_e$, —(CH$_2$)$_p$COOR$_d$, or

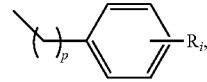

wherein $R_i$ is selected from hydrogen, —CN, halogen, methyl, ethyl and —COOR$_d$, and wherein $R_d$ represents hydrogen, methyl or ethyl;

n, p and q independently represents 0 or 1;

$R_3$ is selected from optionally substituted:

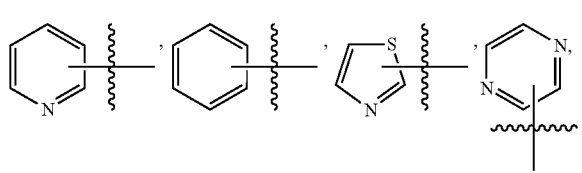

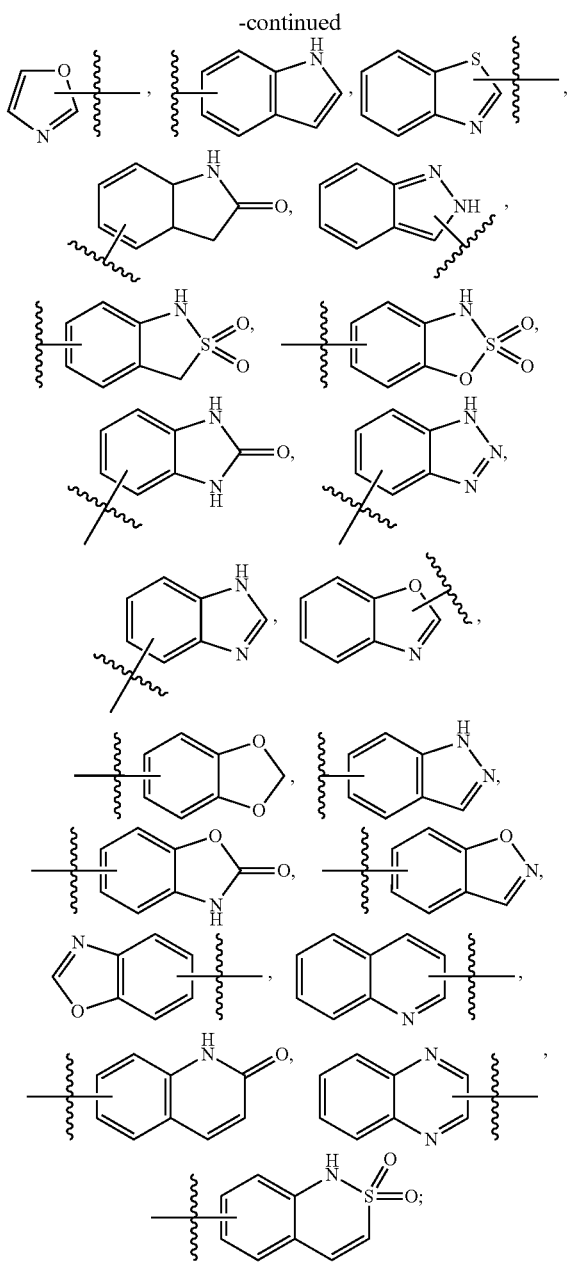

and wherein $R_3$ is optionally substituted with one or more substituents selected independently from —CN, hydroxyl, halogen, methyl, ethyl, propyl, phenyl, benzyl, tetrazolyl, —CH$_2$)$_n$NR$_a$R$_b$, —OR$_c$, —SO$_2$R$_e$, —SO$_2$N(R$_1$)$_2$, —COR$_5$, —C(R$_e$)=N—OH, —(CH$_2$)$_q$COOR$_d$; and

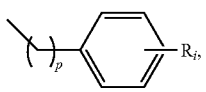

and
wherein A, $R_a$, $R_b$, $R_c$, $R_d$, $R_e$, $R_4$, and q are as defined in claim 1.

4. The compound according to claim 3, wherein $R_4$ represents hydrogen or hydroxyl.

5. A compound selected from the group consisting of:
(S)-1-phenyl-N-(1-phenyl-2-(pyrrolidin-1-yl)ethyl)cyclopropanecarboxamide hydrochloride;
(S)—N-methyl-1-phenyl-N-(1-phenyl-2-(pyrrolidin-yl] ethyl]cyclopentanecarboxamide hydrochloride;
(S)—N-methyl-1-phenyl-N-(1-phenyl-2-(pyrrolidin-1-yl] ethyl]cyclohexane carboxamide hydrochloride;
(S)—N-methyl-1-phenyl-N-(1-phenyl-2-(pyrrolidin-1 yl]ethyl]cyclopropane carboxamide hydrochloride;
(S)—N-methyl-N-(1-phenyl-2-(pyrrolidin-1-yl)ethyl)-1-(quinolin-3-yl)cyclopropane carboxamide hydrochloride;
(S)-1-phenyl-N-(1-phenyl-2-(pyrrolidin-1-yl)ethyl)cyclohexane carboxamide hydrochloride;
(S)—N-(1-phenyl-2-(pyrrolidin-1-yl)ethyl)-1-(pyridin-3-yl)cyclopropane carboxamide hydrochloride;
(S)—N-(1-phenyl-2-(pyrrolidin-1-yl)ethyl)-1-(quinolin-3-yl)cyclopropane carboxamide hydrochloride;
(S)—N-(1-phenyl-2-(pyrrolidin-1-yl)ethyl)-1-(pyridin-2-yl)cyclopropane carboxamide hydrochloride;
N—((S)-2-((S)-3-hydroxypyrrolidin-1-yl)-1-phenylethyl)-1-(quinolin-3-yl)cyclopropane carboxamide hydrochloride;
(S)—N-(3-methyl-1-(pyrrolidin-1-yl) butan-2-yl)-1-(quinolin-3-yl)cyclopropane carboxamide hydrochloride;
(S)-1-(benzo[d]oxazol-2-yl)-N-(1-phenyl-2-(pyrrolidin-1-yl)ethyl)cyclopropane carboxamide;
(S)—N-(1-phenyl-2-(pyrrolidin-1-yl)ethyl)-1-(4-phenylthiazol-2-yl)cyclopropane carboxamide;
(S)-1-(benzo[d][1,3]dioxol-5-yl)-N-(1-phenyl-2-(pyrrolidin-1-yl)ethyl)cyclopropane carboxamide;
(S)-1-(benzo[d]thiazol-2-yl)-N-(1-phenyl-2-(pyrrolidin-1-yl)ethyl)cyclopropane carboxamide;
(S)-1-(3-cyanophenyl)-N-(1-phenyl-2-(pyrrolidin-1-yl) ethyl)cyclopropane carboxamide;
(S)—N-(2-(3-(hydroxymethyl) azetidin-1-yl)-1-phenylethyl)-1-(quinolin-3-yl)cyclopropane carboxamide;
(S)-1-(4-(methylsulfonamido)phenyl)-N-(1-phenyl-2-(pyrrolidin-1-yl)ethyl)cyclopropane carboxamide;
(S)-1-(3-(methylsulfonamido)phenyl)-N-(1-phenyl-2-(pyrrolidin-1-yl)ethyl)cyclopropane carboxamide;
(S)-1-(2-benzyl-2H-indazol-3-yl)-N-(1-phenyl-2-(pyrrolidin-1-yl)ethyl)cyclopropane carboxamide;
(S)—N-(1-phenyl-2-(pyrrolidin-1-yl)ethyl)-1-m-tolyl cyclopropane carboxamide hydrochloride;
(S)-1-(3-hydroxyphenyl)-N-(1-phenyl-2-(pyrrolidin-1-yl) ethyl)cyclopropane carboxamide hydrochloride;
(S)-1-(3-(benzyloxy) phenyl)-N-(1-phenyl-2-(pyrrolidin-1-yl)ethyl)cyclopropane carboxamide hydrochloride;
(S)—N-(2-(3-hydroxyazetidin-1-yl)-1-phenylethyl)-1-(quinolin-3-yl)cyclopropane carboxamide;
(S)-1-(3-(1H-tetrazol-5-yl) phenyl)-N-(1-phenyl-2-(pyrrolidin-1-yl)ethyl)cyclopropane carboxamide;
(S)-1-(3-cyanophenyl)-N-(3-methyl-1-(pyrrolidin-1-yl) butan-2-yl)cyclopropane carboxamide;
N—((S)-2-((S)-3-hydroxy pyrrolidin-1-yl)-1-phenyl ethyl)-1-(3-(methyl sulfonamido)phenyl)cyclopropane carboxamide;
(S)-4-(1-(1-phenyl-2-(pyrrolidin-1-yl)ethyl carbamoyl) cyclopropyl)phenyl methane sulfonate hydrochloride;
4-(1-((S)-2-((S)-3-hydroxypyrrolidin-1-yl)-1-phenylethylcarbamoyl)cyclopropyl)phenyl methanesulfonate hydrochloride;
(S)—N-(3-methyl-1-(pyrrolidin-1-yl) butan-2-yl)-1-(3-(methyl sulfonamido)phenyl)cyclopropane carboxamide;

3-(1-((S)-2-((S)-3-hydroxypyrrolidin-1-yl)-1-phenylethylcarbamoyl)cyclopropyl)phenyl methane sulfonate;

(S)-3-(1-(1-phenyl-2-(pyrrolidin-1-yl)ethyl carbamoyl)cyclopropyl)phenyl methane sulfonate;

N—((S)-2-((R)-3-fluoropyrrolidin-1-yl)-1-phenylethyl)-1-(quinolin-3-yl)cyclopropane carboxamide;

N—((S)-2-((R)-3-hydroxypyrrolidin-1-yl)-1-phenylethyl)-1-(quinolin-3-yl)cyclopropane carboxamide;

N—((S)-2-((R)-3-hydroxypyrrolidin-1-yl)-1-phenylethyl)-1-(3-(methyl sulfonamido)phenyl)cyclopropane carboxamide;

N—((S)-2-((S)-3-fluoro pyrrolidin-1-yl)-1-phenylethyl)-1-(quinolin-3-yl)cyclopropane carboxamide;

N—((S)-2-((S)-3-hydroxypyrrolidin-1-yl)-1-phenylethyl)-1-(3-isocyanophenyl)cyclopropane carboxamide;

N—((S)-2-((S)-3-hydroxy pyrrolidin-1-yl)-1-phenylethyl)-1-(quinoxalin-2-yl)cyclopropane carboxamide;

(S)—N-(1-phenyl-2-(pyrrolidin-1-yl)ethyl)-1-(quinoxalin-2-yl)cyclopropane carboxamide;

(S)—N-(1-phenyl-2-(pyrrolidin-1-yl)ethyl)-1-(pyridin-4-yl)cyclopropane carboxamide;

N—((S)-2-((S)-3-hydroxypyrrolidin-1-yl)-1-phenylethyl)-1-(pyridin-4-yl)cyclopropane carboxamide;

(S)-1-(4-(N,N-dimethylsulfamoyl)phenyl)-N-(1-phenyl-2-(pyrrolidin-1-yl)ethyl)cyclopropane carboxamide;

(S)-1-(4-(methylsulfonamidomethyl)phenyl)-N-(1-phenyl-2-(pyrrolidin-1-yl)ethyl)cyclopropane carboxamide;

N—((S)-2-((S)-3-hydroxypyrrolidin-1-yl)-1-phenyl ethyl)-1-(4-(methyl sulfonamide methyl)phenyl)cyclopropane carboxamide;

(S)-1-(3-(methylsulfonamidomethyl)phenyl)-N-(1-phenyl-2-(pyrrolidin-1-yl)ethyl)cyclopropane carboxamide;

N—((S)-2-((S)-3-hydroxypyrrolidin-1-yl)-1-phenyl ethyl)-1-(3-(methylsulfonamidomethyl)phenyl)cyclopropane carboxamide;

N—((S)-2-((S)-3-(dimethylamino) pyrrolidin-1-yl)-1-phenylethyl)-1-(3-(methylsulfonamido)phenyl)cyclopropanecarboxamide;

N—((S)-2-((S)-3-(dimethylamino) pyrrolidin-1-yl)-1-phenylethyl)-1-(quinolin-2-yl)cyclopropane carboxamide;

(S)-1-(4-(methylsulfonyl)phenyl)-N-(1-phenyl-2-(pyrrolidin-1-yl)ethyl)cyclopropane carboxamide;

(S)-1-(2-(N, N-dimethyl sulfamoyl)phenyl)-N-(1-phenyl-2-(pyrrolidin-1-yl)ethyl)cyclopropane carboxamide;

(S)-1-(3-(methylsulfonyl)phenyl)-N-(1-phenyl-2-(pyrrolidin-1-yl)ethyl)cyclopropane carboxamide hydrochloride;

(S)-1-(3-methoxyphenyl)-N-(1-phenyl-2-(pyrrolidin-1-yl)ethyl)cyclopropane carboxamide;

(S)-1-(2,2-dioxido-1,3-dihydrobenzo[c]isothiazol-5-yl)-N-(1-phenyl-2-(pyrrolidin-1-yl)ethyl)cyclopropane carboxamide;

(S)-1-(4-methoxyphenyl)-N-(1-phenyl-2-(pyrrolidin-1-yl)ethyl)cyclopropane carboxamide;

(S)-1-(2-oxo-1,2-dihydroquinolin-6-yl)-N-(1-phenyl-2-(pyrrolidin-1-yl)ethyl)cyclopropane carboxamide;

(S)-1-(4-chlorophenyl)-N-(1-phenyl-2-(pyrrolidin-1-yl)ethyl)cyclopropane carboxamide; (S)-1-(4-chloro-3-(methyl sulfonamido)phenyl)-N-(1-phenyl-2-(pyrrolidin-1-yl)ethyl)cyclopropane carboxamide;

tert-butyl (S)-1-((S)-2-(1-(3-(methylsulfonamido)phenyl) cyclopropane carboxamido)-2-phenylethyl) pyrrolidin-3-ylcarbamate;

N—((S)-2-((S)-3-(methyl amino) pyrrolidin-1-yl)-1-phenylethyl)-1-(3-(methylsulfonamido)phenyl)cyclopropane carboxamide;

N—((S)-2-((S)-3-amino pyrrolidin-1-yl)-1-phenyl ethyl)-1-(3-(methyl sulfonamido)phenyl)cyclopropane carboxamide 2,2,2-trifluoroacetate;

1-(2,2-Dioxo-2,3-dihydro-2-benzo[1,2,3]oxathiazol 5-yl)-cyclopropane carboxylic acid (1-phenyl-2-pyrrolidin-1-yl-ethyl)-amide;

1-(3-Dimethylsulfamoyl-phenyl)-cyclopropane carboxylic acid (1-phenyl-2-pyrrolidin-1-yl-ethyl)-amide;

1-(4-Sulfamoyl-phenyl)-cyclopropane carboxylic acid (1-phenyl-2-pyrrolidin-1-yl-ethyl)-amide;

1-(3-Acetyl-4-hydroxyphenyl)-cyclopropane carboxylic acid (1-phenyl-2-pyrrolidin-1-yl-ethyl)-amide;

1-(2-Oxo-2,3-dihydro-benzooxazol-5-yl)-cyclopropane carboxylic acid (1-phenyl-2-pyrrolidin-1-yl-ethyl)-amide;

1-(3-Methanesulfonylamino-phenyl)-cyclopropane carboxylic acid (1-benzyl-2-pyrrolidin-1-yl-ethyl)-amide;

1-(3-Methanesulfonylamino-phenyl)-cyclopropane carboxylic acid (1-pyridin-3-yl-2-pyrrolidin-1-yl-ethyl)-amide;

(S)—N-(1-cyclohexyl-2-(pyrrolidin-1-yl)ethyl)-1-(3-(methylsulfonamido)phenyl)cyclopropane carboxamide;

(S)—N-(4-methyl-1-(pyrrolidin-1-yl)pentan-2-yl)-1-(3-(methylsulfonamido)phenyl)cyclopropanecarboxamide;

(R)—N-(1-(3-(benzyloxy)phenyl)-2-(pyrrolidin-1-yl)ethyl)-1-(3-(methyl sulfonamido)phenyl)cyclopropanecarboxamide;

(R)—N-(1-(3-hydroxyphenyl)-2-(pyrrolidin-1-yl)ethyl)-1-(3-(methylsulfonamido)phenyl)cyclopropanecarboxamide;

(R)—N-(1-(3-methoxyphenyl)-2-(pyrrolidin-1-yl)ethyl)-1-(3-(methylsulfonamido)phenyl)cyclopropanecarboxamide;

1-(3-Methanesulfonylamino-4-methoxy-phenyl)-cyclopropane carboxylic acid (1-phenyl-2-pyrrolidin-1-yl-ethyl)-amide;

1-(3-Methyl-benzo[d]isoxazol-5-yl)-cyclopropane carboxylic acid (1-phenyl-2-pyrrolidin-1-yl-ethyl)-amide;

1-(6-Ethoxy-pyridin-2-yl)-cyclopropane carboxylic acid (1-phenyl-2-pyrrolidin-1-yl-ethyl)-amide;

1-(4-Methanesulfonylamino-3-methyl-phenyl)-cyclopropane carboxylic acid (1-phenyl-2-pyrrolidin-1-yl-ethyl)-amide;

1-(3-Methanesulfonylamino-4-methyl-phenyl)-cyclopropane carboxylic acid (1-phenyl-2-pyrrolidin-1-yl-ethyl)-amide;

1-(3-Formylamino-4-hydroxy-phenyl)-cyclopropanecarboxylic acid (1-phenyl-2-pyrrolidin-1-yl-ethyl)-amide;

1-(4-Fluoro-3-methanesulfonylamino-phenyl)-cyclopropane carboxylic acid (1-phenyl-2-pyrrolidin-1-yl-ethyl)-amide;

1-(2,2-Dioxo-2,3-dihydro-1H-2-benzo[c]isothiazol-6-yl)-cyclopropane carboxylic acid (1-phenyl-2-pyrrolidin-1-yl-ethyl)-amide;

1-Benzooxazol-6-yl-cyclopropanecarboxylic acid (1-phenyl-2-pyrrolidin-1-yl-ethyl)-amide;

3-[1-(1-Phenyl-2-pyrrolidin-1-yl-ethylcarbamoyl)-cyclopropyl]-benzamide;

1-(2,4-Difluoro-5-methanesulfonylamino-phenyl)-cyclopropane carboxylic acid (1-phenyl-2-pyrrolidin-1-yl-ethyl)-amide;

1-[4-Hydroxy-3-(1-hydroxyimino-ethyl)-phenyl]-cyclopropane carboxylic acid (1-phenyl-2-pyrrolidin-1-yl-ethyl)-amide;
1-(2-Oxo-2,3-dihydro-1H-benzoimidazol-5-yl)-cyclopropane carboxylic acid (1-phenyl-2-pyrrolidin-1-yl-ethyl)-amide;
1-(1-Methyl-1H-benzotriazol-5-yl)cyclopropane carboxylic acid (1-phenyl-2-pyrrolidin-1-yl-ethyl)-amide;
1-(2-Oxo-1,2-dihydro-quinolin-7-yl)-cyclopropane carboxylic acid (1-phenyl-2-pyrrolidin-1-yl-ethyl)-amide;
{3-[1-(1-Phenyl-2-pyrrolidin-1-yl-ethylcarbamoyl)-cyclopropyl]-phenoxy}-acetic acid;
4-[1-(1-Phenyl-2-pyrrolidin-1-yl-ethylcarbamoyl)-cyclopropyl]-benzamide;
1-(2,2-Dioxo-1,2-dihydro-2l6-benzo[c][1,2]thiazin-7-yl)-cyclopropane carboxylic acid (1-phenyl-2-pyrrolidin-1-yl-ethyl)-amide;
1-(1H-Benzoimidazol-5-yl)-cyclopropane carboxylic acid (1-phenyl-2-pyrrolidin-1-yl-ethyl)-amide;
1-(4-Fluoro-3-methanesulfonylamino-phenyl)-cyclopropane carboxylic acid (1-phenyl-2-pyrrolidin-1-yl-ethyl)-amide hydrochloride;
1-(4-Fluoro-3-methanesulfonylamino-phenyl)-cyclopropanecarboxylic acid [2-(3-hydroxy-pyrrolidin-1-yl)-1-phenyl-ethyl]-amide;
{4-[1-(1-Phenyl-2-pyrrolidin-1-yl-ethylcarbamoyl)-cyclopropyl]-phenoxy}-acetic acid;
(S)-1-(6-(methylsulfonamido)pyridin-3-yl)-N-(1-phenyl-2-(pyrrolidin-1-yl)ethyl)cyclopropanecarboxamide;
(S)-1-(2,2-dioxido-1H-benzo[c][1,2]thiazin-6-yl)-N-(1-phenyl-2-(pyrrolidin-1-yl)ethyl)cyclopropanecarboxamide;
(S)-1-(1H-indazol-5-yl)-N-(1-phenyl-2-(pyrrolidin-1-yl)ethyl)cyclopropanecarboxamide;
(S)-1-(benzo[d]isoxazol-5-yl)-N-(1-phenyl-2-(pyrrolidin-1-yl)ethyl)cyclopropane carboxamide;
(S)-3-(1-(1-phenyl-2-(pyrrolidin-1-yl)ethylcarbamoyl)cyclopropyl)benzoic acid;
(S)—N-(1-(3-methoxyphenyl)-2-(pyrrolidin-1-yl)ethyl)-1-(2-oxo-2,3-dihydrobenzo[d]oxazol-5-yl)cyclopropanecarboxamide;
N—((S)-2-((S)-3-hydroxypyrrolidin-1-yl)-1-phenyl-ethyl)-1-(2-oxo-2,3-dihydrobenzo[d]oxazol-5-yl)cyclopropanecarboxamide;
(S)-tert-butyl 2-(2-oxo-5-(1-(1-phenyl-2-(pyrrolidin-1-yl)ethylcarbamoyl)cyclopropyl)benzo[d]oxazol-3(2H)-yl)acetate;
(S)-2-(2-oxo-5-(1-(1-phenyl-2-(pyrrolidin-1-yl)ethylcarbamoyl)cyclopropyl)benzo[d]oxazol-3(2H)-yl)acetic acid hydrochloride;
(S)—N-(1-cyclohexyl-2-(pyrrolidin-1-yl)ethyl)-1-(2-oxo-2,3-dihydrobenzo[d]oxazol-5-yl)cyclopropanecarboxamide;
(S)-1-(3-methyl-1H-indazol-5-yl)-N-(1-phenyl-2-(pyrrolidin-1-yl)ethyl)cyclopropane carboxamide;
(S)—N-(1-(3-methoxyphenyl)-2-(pyrrolidin-1-yl)ethyl)-1-(3-methyl-1H-indazol-5-yl)cyclopropanecarboxamide;
(S)-4-(1-(1-phenyl-2-(pyrrolidin-1-yl)ethyl carbamoyl) cyclopropyl)benzoic acid;
(S)-1-(3-methyl-2-oxo-2,3-dihydrobenzo[d]oxazol-5-yl)-N-(1-phenyl-2-(pyrrolidin-1-yl)ethyl)cyclopropanecarboxamide;
N—((S)-1-cyclohexyl-2-((S)-3-hydroxypyrrolidin-1-yl)ethyl)-1-(2-oxo-2,3-dihydrobenzo[d]oxazol-5-yl)cyclopropanecarboxamide;
(S)—N-(1-(3-cyanophenyl)-2-(pyrrolidin-1-yl)ethyl)-1-(2-oxo-2,3-dihydrobenzo[d]oxazol-5-yl)cyclopropanecarboxamide;
(S)-3-(1-(1-(2-oxo-2,3-dihydrobenzo[d]oxazol-5-yl)cyclopropanecarboxamido)-2-(pyrrolidin-1-yl)ethyl)benzamide;
(S)-2-(3-(1-(1-(3-(methylsulfonamido)phenyl)cyclopropanecarboxamido)-2-(pyrrolidin-1-yl)ethyl)phenoxy)acetic acid;
(S)—N-(1-(3-(benzyloxy)phenyl)-2-(pyrrolidin-1-yl)ethyl)-1-(2-oxo-2,3-dihydrobenzo[d]oxazol-5-yl)cyclopropanecarboxamide;
(S)—N-(1-(3-hydroxyphenyl)-2-(pyrrolidin-1-yl)ethyl)-1-(2-oxo-2,3-dihydrobenzo[d]oxazol-5-yl)cyclopropanecarboxamide;
(S)-1-(4-cyanophenyl)-N-(1-phenyl-2-(pyrrolidin-1-yl)ethyl)cyclopropanecarboxamide;
(S)-3-(1-(1-(2-oxo-2,3-dihydrobenzo[d]oxazol-5-yl)cyclopropanecarboxamido)-2-(pyrrolidin-1-yl)ethyl)phenyl methanesulfonate 2,2,2-trifluoroacetate;
(S)—N-(1-(3-(2H-tetrazol-5-yl)phenyl)-2-(pyrrolidin-1-yl)ethyl)-1-(2-oxo-2,3-dihydro benzo[d]oxazol-5-yl)cyclopropanecarboxamide;
N—((S)-2-((S)-3-hydroxypyrrolidin-1-yl)-1-(3-methoxyphenyl)ethyl)-1-(2-oxo-2,3-dihydro benzo[d]oxazol-5-yl)cyclopropanecarboxamide;
(S)-methyl 4-((5-(1-(1-(3-hydroxyphenyl)-2-(pyrrolidin-1-yl)ethylcarbamoyl)cyclopropyl)-2-oxobenzo[d]oxazol-3(2H)-yl)methyl)benzoate;
(S)-methyl 3-((5-(1-(1-(3-hydroxyphenyl)-2-(pyrrolidin-1-yl)ethylcarbamoyl)cyclopropyl)-2-oxobenzo[d]oxazol-3(2H)-yl)methyl)benzoate;
N—((S)-1-(3-hydroxyphenyl)-2-((S)-3-hydroxypyrrolidin-1-yl)ethyl)-1-(2-oxo-2,3-dihydro benzo[d]oxazol-5-yl)cyclopropanecarboxamide;
N—((S)-1-(3-hydroxyphenyl)-2-((S)-3-hydroxypyrrolidin-1-yl)ethyl)-1-(2-oxo-2,3-dihydro benzo[d]oxazol-5-yl)cyclopropanecarboxamide;
(S)—N-(1-(3-aminophenyl)-2-(pyrrolidin-1-yl)ethyl)-1-(2-oxo-2,3-dihydrobenzo[d]oxazol-5-yl)cyclopropanecarboxamide;
(S)-1-(2-oxoindolin-6-yl)-N-(1-phenyl-2-(pyrrolidin-1-yl)ethyl)cyclopropanecarboxamide;
(S)—N-(1-(3-(3-cyanobenzyloxy)phenyl)-2-(pyrrolidin-1-yl)ethyl)-1-(2-oxo-2,3-dihydrobenzo[d]oxazol-5-yl)cyclopropanecarboxamide;
(S)—N-(1-(3-(4-cyanobenzyloxy)phenyl)-2-(pyrrolidin-1-yl)ethyl)-1-(2-oxo-2,3-dihydrobenzo[d]oxazol-5-yl)cyclopropanecarboxamide;
1-(2-Oxo-2,3-dihydrobenzo[d]oxazol-5-yl)-N-(2-(pyrrolidin-1-yl)-1-(tetrahydro-2H-pyran-4-yl)ethyl)cyclopropanecarboxamide;
N-(1-(1-benzyl-1H-pyrazol-4-yl)-2-(pyrrolidin-1-yl)ethyl)-1-(2-oxo-2,3-dihydrobenzo[d]oxazol-5-yl)cyclopropane carboxamide;
(S)-methyl-3-(2-oxo-5-(1-(1-phenyl-2-(pyrrolidin-1-yl)ethylcarbamoyl)cyclopropyl)benzo[d]oxazol-3 (2H)-yl)methyl)benzoate;
(S)—N-(1-(3-(methylsulfonamido)phenyl)-2-(pyrrolidin-1-yl)ethyl)-1-(2-oxo-2,3-dihydrobenzo[d]oxazol-5-yl)cyclopropanecarboxamide; and
(S)—N-methyl-1-phenyl-N-(1-phenyl-2-(pyrrolidin-1-yl]ethyl]cyclobutane carboxamide hydrochloride;
or a stereoisomer tereof or a pharmaceutically acceptable salt thereof.

6. A pharmaceutical composition comprising one or more compounds according to claim 1 or a stereoisomer thereof or a pharmaceutically acceptable salt thereof and at least one pharmaceutically acceptable carrier.

7. A pharmaceutical composition comprising one or more compounds according to claim 5 or a stereoisomer thereof or a pharmaceutically acceptable salt thereof and at least one pharmaceutically acceptable carrier.

8. The compound according to claim 1, which is kappa (κ) opioid receptor (KOR) agonist.

9. The compound according to claim 5, which is kappa (κ) opioid receptor (KOR) agonist.

10. A method of binding an opioid receptor in a patient, comprising administering to the patient a therapeutically effective amount of a compound according to claim 1, or a stereoisomer thereof or a pharmaceutically acceptable salt thereof.

11. The method according to claim 10, wherein the compound binds κ opioid receptor site.

12. The method according to claim 11, wherein the κ opioid receptor site is located in the central nervous system.

13. The method according to claim 12, wherein the κ opioid receptor site is located peripherally to the central nervous system.

14. A method of treating gastrointestinal dysfunction in a patient comprising administering to the patient a therapeutically effective amount of a compound according to claim 1 or a stereoisomer thereof or a pharmaceutically acceptable salt thereof.

15. A method of treating ileus in a patient comprising administering to the patient a therapeutically effective amount of a compound according to claim 1 or a stereoisomer thereof or a pharmaceutically acceptable salt thereof.

16. A method of treating pain in a patient comprising administering to the patient a therapeutically effective amount of a compound according to claim 1 or a stereoisomer thereof or a pharmaceutically acceptable salt thereof.

17. The method according to claim 16, wherein the pain is selected from the group consisting of acute pain and chronic pain.

18. The method according to claim 16, wherein the pain is selected from the group consisting of nociceptive pain, inflammatory pain, visceral pain, somatic pain, neuralgia, neuropathic pain, pain caused by autoimmune diseases (AIDS), pain caused by cancer, phantom pain, psychogenic pain, pain resulting from hyperalgesia, pain caused by rheumatoid arthritis, migraine and allodynia.

19. A method of binding an opioid receptor in a patient, comprising administering to the patient a therapeutically effective amount of a compound according to claim 5, or a stereoisomer thereof or a pharmaceutically acceptable salt thereof.

20. The method according to claim 1, wherein the compound binds κ opioid receptor site.

21. The method according to claim 20, wherein the κ opioid receptor site is located in the central nervous system.

22. The method according to claim 21, wherein the κ opioid receptor site is located peripherally to the central nervous system.

23. A method of treating gastrointestinal dysfunction in a patient comprising administering to the patient a therapeutically effective amount of a compound according to claim 5 or a stereoisomer thereof or a pharmaceutically acceptable salt thereof.

24. A method of treating ileus in a patient comprising administering to the patient a therapeutically effective amount of a compound according to claim 5 or a stereoisomer thereof or a pharmaceutically acceptable salt thereof.

25. A method of treating pain in a patient comprising administering to the patient a therapeutically effective amount of a compound according to claim 5 or a stereoisomer thereof or a pharmaceutically acceptable salt thereof.

26. The method according to claim 25, wherein the pain is selected from the group consisting of acute pain and chronic pain.

27. The method according to claim 25, wherein the pain is selected from the group consisting of nociceptive pain, inflammatory pain, visceral pain, somatic pain, neuralgia, neuropathic pain, pain caused by autoimmune diseases (AIDS), pain caused by cancer, phantom pain, psychogenic pain, pain resulting from hyperalgesia, pain caused by rheumatoid arthritis, migraine and allodynia.

* * * * *